US012791517B2

(12) United States Patent
Xu et al.

(10) Patent No.: US 12,791,517 B2
(45) Date of Patent: Nov. 10, 2026

(54) THREE-DIMENSIONAL TRANSISTOR ARRAYS FOR INTRA- AND INTER-CELLULAR RECORDING

(71) Applicant: THE REGENTS OF THE UNIVERSITY OF CALIFORNIA, Oakland, CA (US)

(72) Inventors: Sheng Xu, La Jolla, CA (US); Yue Gu, La Jolla, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 108 days.

(21) Appl. No.: 18/566,451

(22) PCT Filed: Jun. 6, 2022

(86) PCT No.: PCT/US2022/032331
§ 371 (c)(1),
(2) Date: Dec. 1, 2023

(87) PCT Pub. No.: WO2022/260992
PCT Pub. Date: Dec. 15, 2022

(65) Prior Publication Data
US 2024/0255464 A1 Aug. 1, 2024

Related U.S. Application Data

(60) Provisional application No. 63/208,181, filed on Jun. 8, 2021.

(51) Int. Cl.
*G01N 27/414* (2006.01)
*G01N 33/50* (2006.01)

(52) U.S. Cl.
CPC ..... *G01N 27/4148* (2013.01); *G01N 27/4145* (2013.01); *G01N 33/5061* (2013.01)

(58) Field of Classification Search
None
See application file for complete search history.

(56) References Cited

U.S. PATENT DOCUMENTS

| | | | |
|---|---|---|---|
| 7,335,942 | B2 | 2/2008 | Edinger |
| 8,263,964 | B2 | 9/2012 | Yu |
| 2012/0032286 | A1 | 2/2012 | Trusov et al. |
| 2016/0027846 | A1 | 1/2016 | Lieber et al. |
| 2016/0381789 | A1 | 12/2016 | Rogers et al. |
| 2017/0069858 | A1 | 3/2017 | Lieber et al. |

*Primary Examiner* — J. Christopher Ball
(74) *Attorney, Agent, or Firm* — Kaplan Breyer Schwarz LLP

(57) ABSTRACT

A method for fabricating a three-dimensional (3D) FET sensor array includes fabricating a two-dimensional (2D) precursor field-effect transistor (FET) sensor array having a plurality of nanoscale or microscale FETs using any suitable microfabrication techniques. Each of the nanoscale or microscale FETs have a kink at which a FET channel is located. The 2D nanoscale or microscale precursor FET sensor array is caused to buckle or fold into a third dimension, also using any suitable technique.

14 Claims, 82 Drawing Sheets

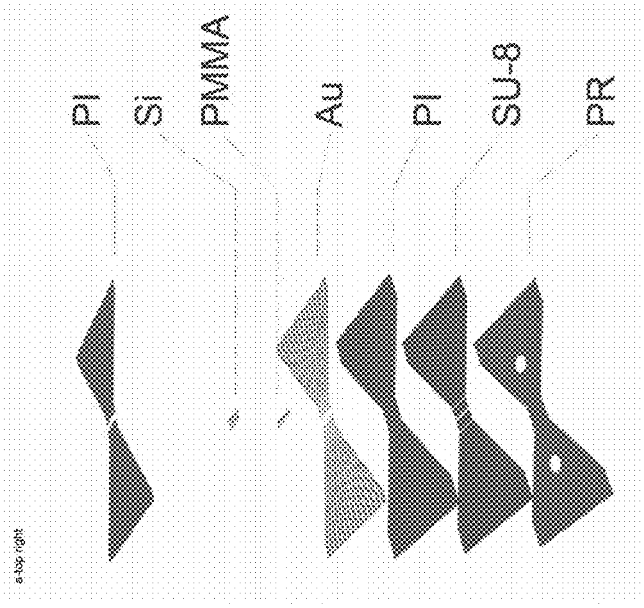
FIG. 1A
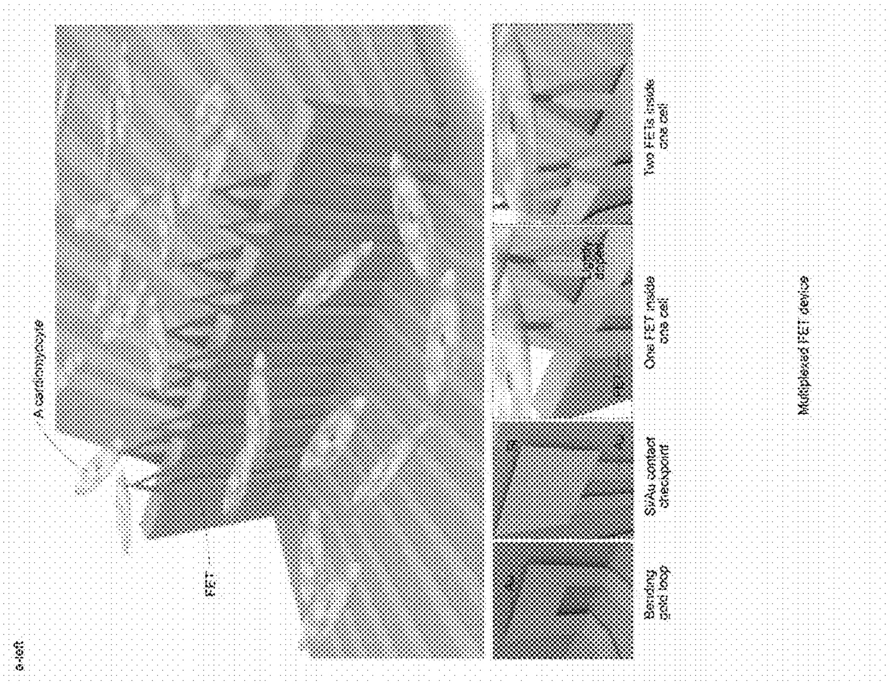

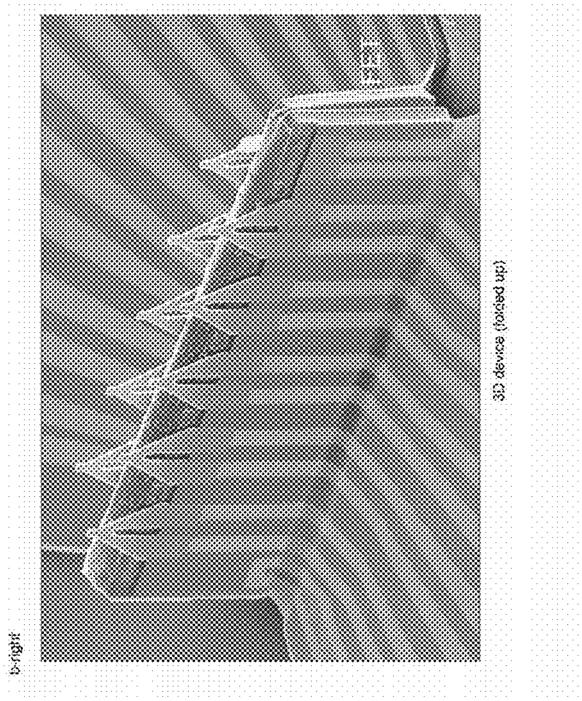
FIG. 1B
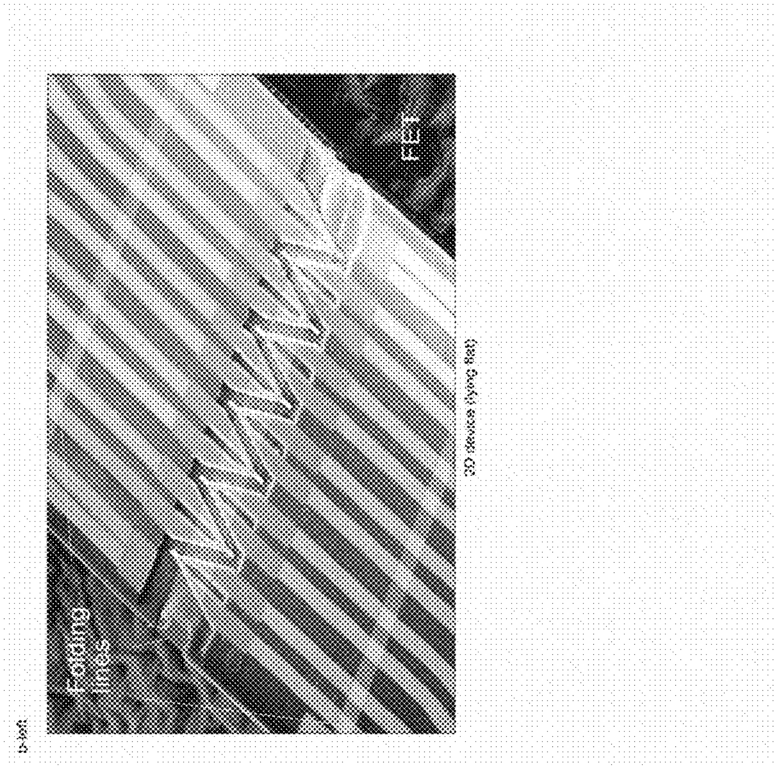

Si FETs left on the PI substrate

Etched PI (first/upper layer)

Defined metal connection

Defined PMMA protection

Defined PI protection (second/lower layer)

Defined SU-8 structure

Defined photoresist sacrificial layer

Device picked up by a PDMS stamp

GUI

THREE-DIMENSIONAL TRANSISTOR ARRAYS FOR INTRA- AND INTER-CELLULAR RECORDING

GOVERNMENT FUNDING

This invention was made with government support under GM138250 awarded by the National Institutes of Health. The government has certain rights in the invention.

BACKGROUND

Electrophysiological approaches have been used to elucidate and modulate the activities of electrogenic cells. Transmembrane potentials associated with ionic fluxes between the cytosol and interstitium underlie the macroscopic electrophysiological characteristics of tissues and organs. Research in this field is largely driven by the use of well-established tools for high-fidelity transmembrane potential recording in single cells or multicellular networks. Ideally, the recording needs to be highly accurate and scalable over a large area. Sensors' contact with the cytoplasm is needed for direct intracellular sensing. Patch clamping, in its various forms, has been the gold standard for recording transmembrane potentials. However, it is challenging to perform on multiple cells simultaneously. Methods based on voltage-sensitive dyes can record multiple cells in parallel but are plagued by cytotoxicity and low temporal resolution. Therefore, a variety of potentially scalable approaches have been explored for intracellular electrical recording, including passive electrodes and active FETs. Passive electrodes have difficulties in picking up subthreshold and low-amplitude cellular signals due to their intrinsically large impedance. Active FET, with minimal access impedance and wide bandwidths, have shown great promise for either intracellular sensing or scalability, but have not yet been demonstrated to meet requirements for both.

SUMMARY

Described herein, in one aspect, is a scalable three-dimensional (3D) FET sensor array that enables accurate recording of transmembrane potentials in electrogenic cells. The sensor array employs a three-dimensional (3D) high-performance field-effect transistor (FET) array for minimally invasive cellular interfacing that produces faithful recordings as validated by the gold standard patch-clamp. Leveraging the high spatial and temporal resolutions of the FETs, the intracellular signal conduction velocity of a cardiomyocyte ($0.182\ m\cdot s^{-1}$) was measured, which is about five times the intercellular velocity. Also demonstrated are intracellular recordings in cardiac muscle tissue constructs that reveal the signal conduction paths. The three-dimensional (3D) FET sensor array can provide new capabilities in probing electrical behaviors of single cells and cellular networks, which carries broad implications for understanding cellular physiology, pathology, and cell-cell interactions.

In another particular aspect, a method is provided for fabricating a three-dimensional (3D) FET sensor array. In accordance with the method, a two-dimensional (2D) precursor field-effect transistor (FET) sensor array having a plurality of nanoscale or microscale FETs is fabricated using any suitable microfabrication techniques. Each of the nanoscale or microscale FETs have a kink at which a FET channel is located. The 2D nanoscale or microscale precursor FET sensor array is caused to buckle or fold into a third dimension, also using any suitable technique.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure.

BRIEF DESCRIPTION OF THE DRAWINGS

FIGS. 1*a*-1*d* show one example of the 3D FET sensor arrays described herein.

DETAILED DESCRIPTION

Described herein, in one aspect, is a scalable 3D FET sensor array for intracellular sensing, as well as for measuring intercellular signal conduction in both two-dimensional (2D) cultures and 3D tissue constructs. The particular embodiment shown in FIG. 1*a* and the figures that follow and described in connection therewith is presented for illustrative purposes only and not as a limitation on the devices, systems and methods described herein. The 3D FET sensor array enables direct measurement of intracellular signal conduction velocity, which is closely related to heart pathology, where its irregularities may be implicative of severe cardiac conditions. It is demonstrated that the intracellular signal conduction velocity in cardiomyocytes is about five times the intercellular conduction velocity reported conventionally. The difference between intracellular and intercellular velocities indicates the coupling efficacy between cells. Also demonstrated are intracellular recordings of cardiomyocytes in cardiac muscle tissue constructs, revealing the signal conduction paths, which paves the way for intracellular electrophysiological studies in vivo.

Fabrication and Characterization of the 3D FET Sensor Arrays

FIG. 1*a* show a schematic diagram of one example of the 3D FET sensor array described herein. In particular, FIG. 1*a* shows a 10-FET array interfacing with a group of cardiomyocytes. An exploded view at the top right illustrates a multilayered design of the illustrative FET array. Inset images at the bottom show, from left to right, an Au loop for checking the electrical conductivity after the device buckles, an Au/Si bilayer for probing the quality of electrical contact after the device is soaked in an acidic solution, one FET recording intracellular signals, and two FETs in the same cell to study intracellular signal conductions. The red area on each FET denotes the lightly doped channel.

Figure 1C:
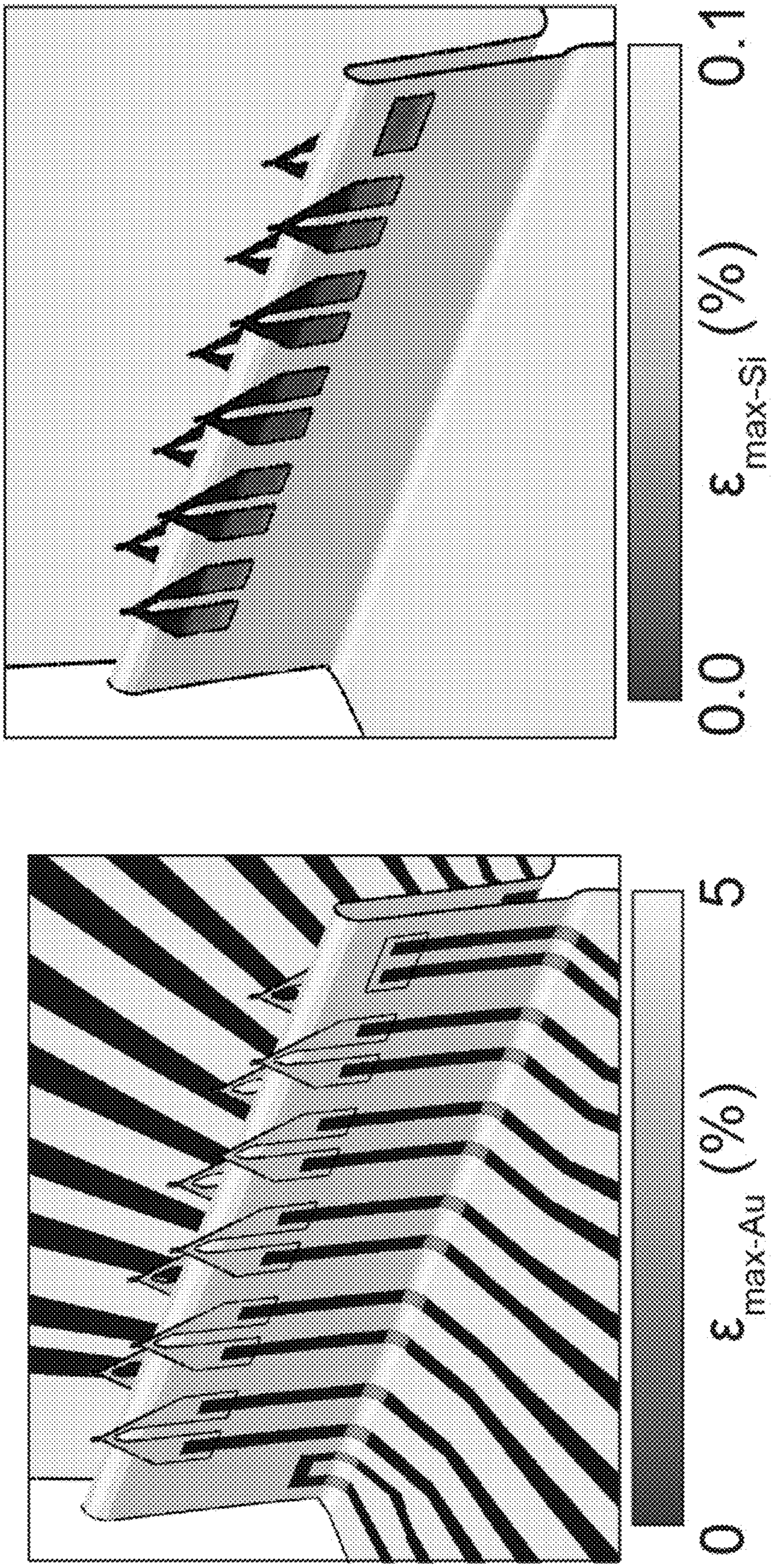
Figure 1D:
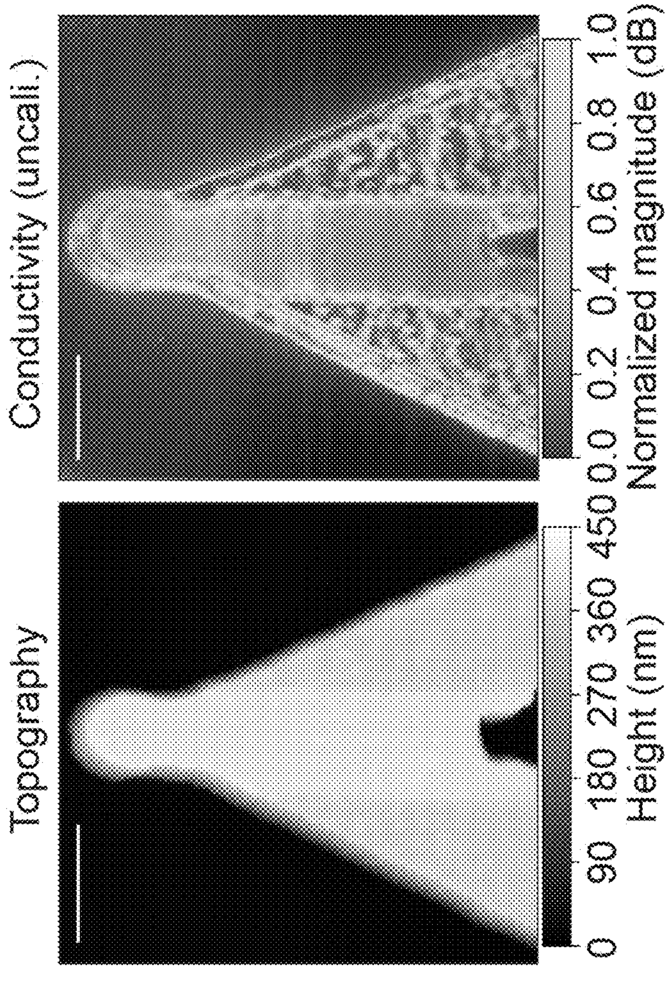

FIG. 1*b* shows SEM images showing the transformation from a 2D precursor (left) to a 3D 10-FET array (right). Each FET in this example has a tapering tip (5 μm long and 1~2 μm wide). The scale bars in FIG. 1*b* are 50 μm. FIG. 1*c* shows a finite element analysis of a 3D 10-FET array. The maximum strains in Au and Si are well below the fracture limit of each material. FIG. 1*d* show images of an FET tip by atomic force microscopy (left) and a scanning microwave microscopy (right). The former operates in the contact mode and maps the surface topography of the FET. The latter maps the uncalibrated conductivity, and thus the admittance distribution, of the FET. A lightly doped region can be clearly distinguished in both images. Because of over-etching of the oxide doping mask, the lightly doped region is slightly thicker than the surrounding heavily doped regions Also, the lightly doped region shows a lower conductivity than the surrounding heavily doped regions. The scale bars in FIG. 1*d* are 2 μm.

The illustrative 3D FET sensor array depicted in FIGS. 1*a*-1*d* was constructed using a compressive buckling technique such as discussed in Xu, S. et al. "Assembly of micro/nanomaterials into complex, three-dimensional architectures by compressive buckling," *Science* 347, 154-159 (2015). First, a multi-layered two-dimensional (2D) precursor was fabricated using standard micro/nanofabrication (see FIG. 1*b* left). The precursor was transferred, and selected regions were bonded onto a prestrained elastomer substrate, after which the prestrain of the elastomer substrate was released. The compression causes the 2D precursor to buckle at predesigned hinge locations to form a 3D shape (see FIG. 1*b* right). To verify the electrical functions of the device before and after the buckling, dummy structures consisting of Au and Si/Au are processed in parallel and used as checkpoints (bottom insets in FIG. 1*a*). The 3D structure is coated with a bilayer of Parylene C and $SiO_2$ for electrical insulation and hydrophilic surface functionalization. The compressive buckling technique enables the fabrication 3D FET sensor arrays at various scales, with different materials, layouts, dimensions, and geometries. Accordingly, those of ordinary skill will recognize that the techniques described herein are not limited to the particular 3D FET sensor array depicted in FIGS. 1*a*-1*d* or the particular fabrication techniques described herein, which are presented for purposes of illustration only. More generally, the principles presented herein are applicable to a wide range of different 3D FET sensor arrays that may be fabricated in accordance with a variety of different techniques.

For instance, the semiconductor material from which the FETs are formed can be, by way of illustration, Si, Ge, III-V materials, perovskites, two-dimensional materials, and/or carbon nanotubes. The electrodes in the sensor array can be formed from materials such as metals, conductive polymers, oxides, and composites. Likewise, the dielectric materials that are used can be polymers, ceramics, and/or composites.

In the various embodiments, the 3D geometry of sensor array allows the FET to penetrate the cell membrane and record low-amplitude sub-threshold signals inside the cell. The small sensor tip (e.g., 1~2 μm) penetrates the cell membrane with minimal invasiveness. As shown in FIG. 1*a*, the device layout is designed to allow interfacing with multiple cells and even having two FETs in the same cell. To make the entire device mechanically robust, we have carried out theoretical and experimental studies to optimize the materials and their dimensions, such as using low molecular weight poly(methyl methacrylate) (PMMA) and thick acid-resistant photoresist as sacrificial layers. As simulated by finite element analysis (see FIG. 1*c*), after the optimization, the maximum strains of the Au and Si in the buckled 3D device are 4% and 0.05%, respectively, which are under their failure strains. The buckling process is reversible. Upon externally applied tensile strain, the 3D device unfolds and recovers to the 2D geometry. The softness of the device reduces the mechanical mismatch between the cell culture and the device. The FET's structure was verified by scanning microwave microscopy in topographic and reflection coefficient mapping modes (see FIG. 1*d* and FIG. 7).

The ability of an FET to accurately capture cellular signals, especially the low-amplitude sub-threshold potentials, depends on its sensitivity and noise level. The sensitivity is determined by the transconductance, which is tunable by the doping profile of the conduction channel. Lower doping concentrations typically yield higher sensitivities. However, noise level also increases with sensitivity, especially in the low-frequency regime. Therefore, we use the sensitivity-to-noise ratio to characterize the FET performance.

Figure 2A:
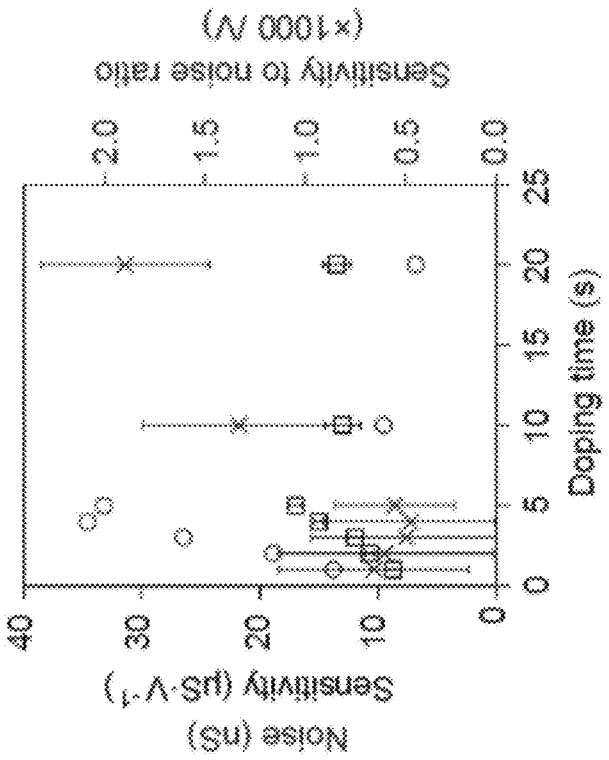
FIGS. 2*a*-2*g* illustrate electrical optimizations and characterizations of the 3D FET sensor arrays.
Figure 2B:
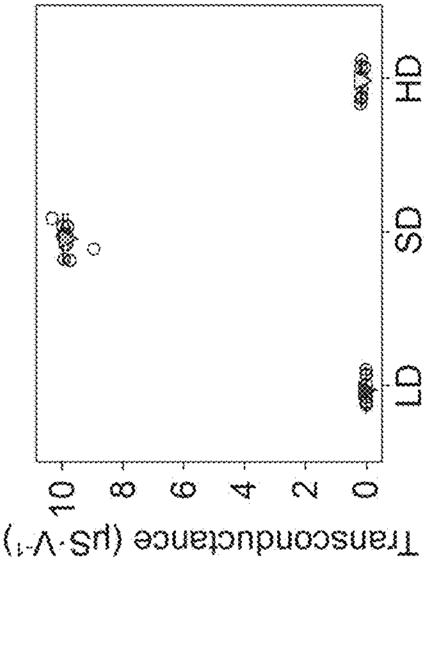
Figure 2C:
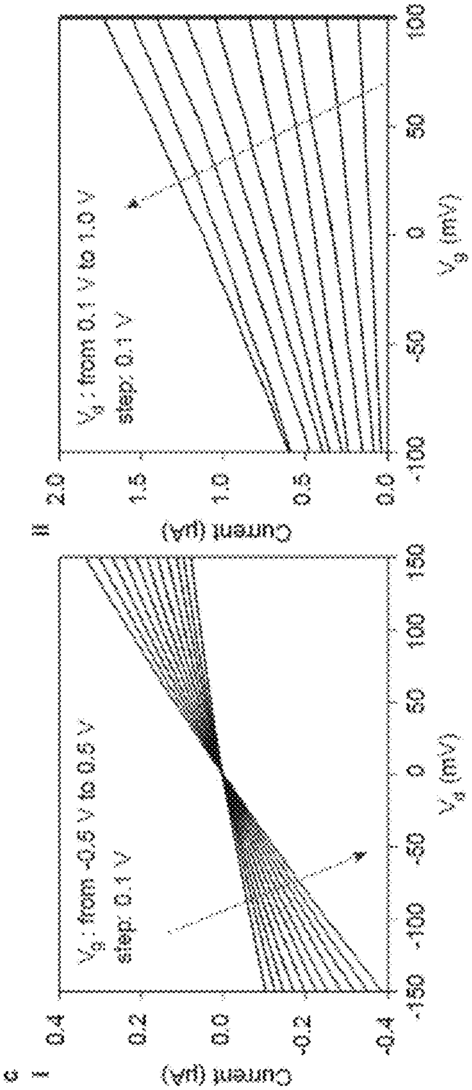
Figure 2D:
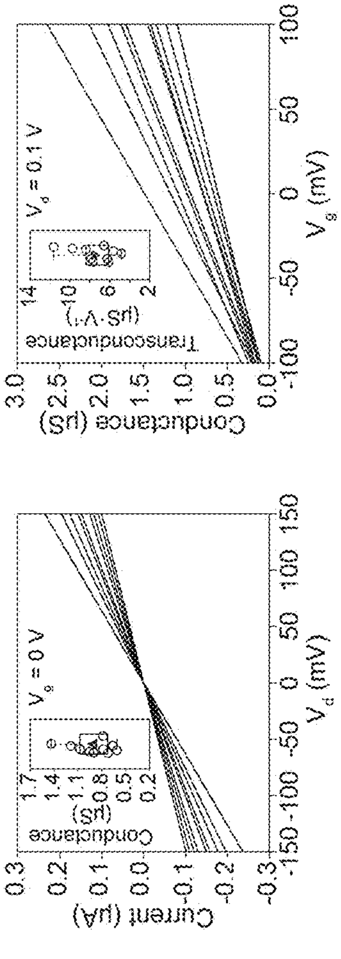
Figure 2F:
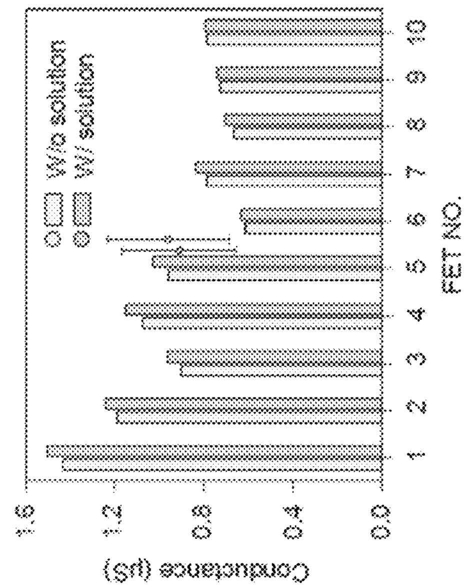
Figure 2E:
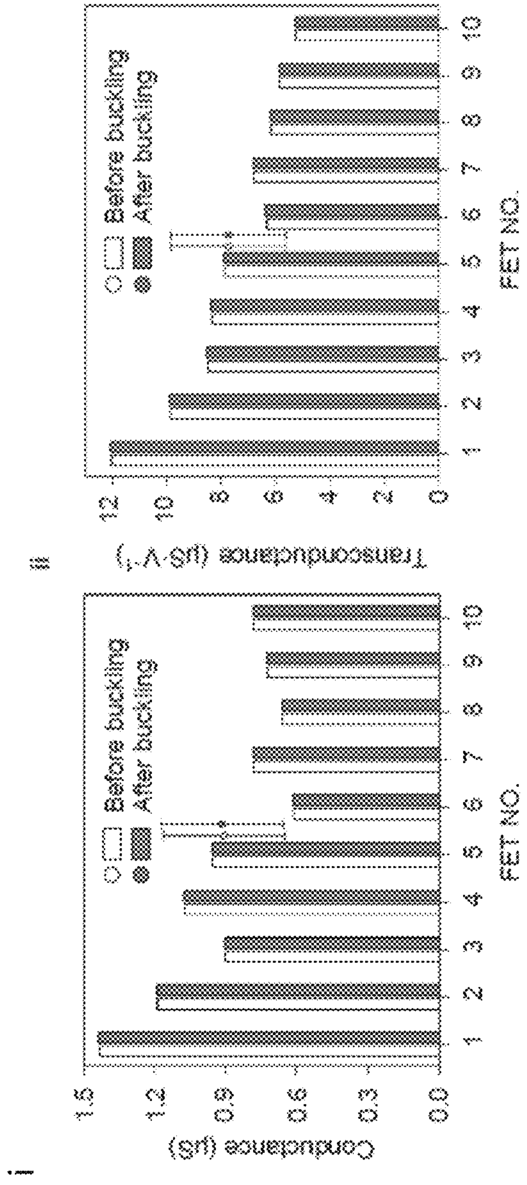
Figure 2G:
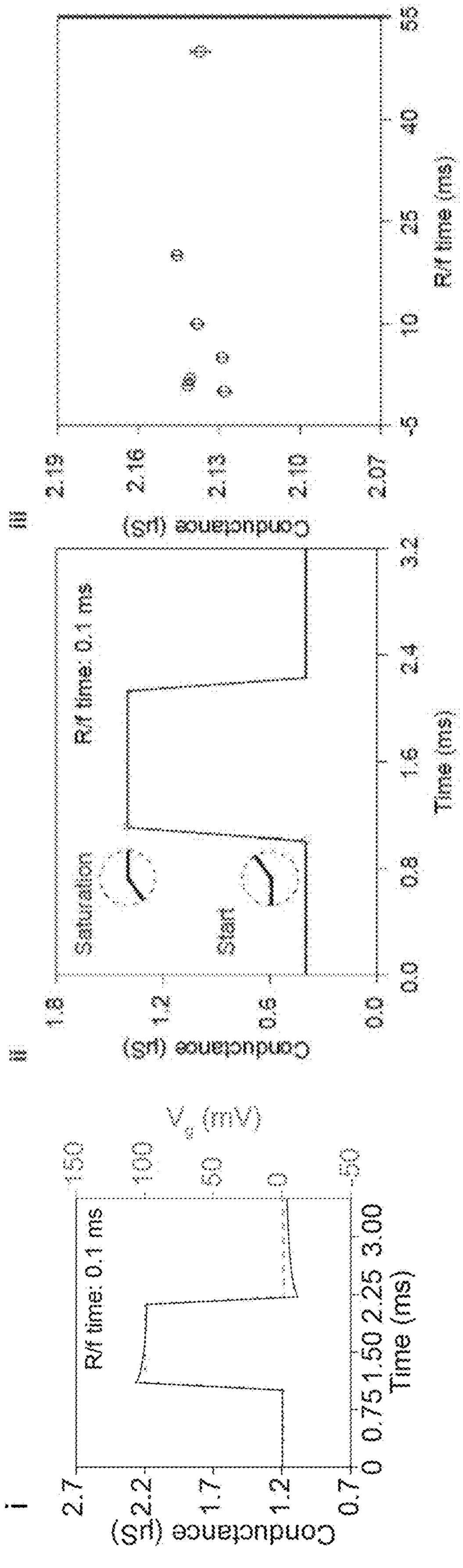

FIGS. 2*a*-2*g* illustrates the electrical optimization and characteristics of the 3D FET sensor array. In particular, FIG. 2*a* shows the FET's sensitivity-to-noise ratio as a function of the doping time in the lightly doped region. A doping time greater than 4 seconds leads to a lower current in the conduction channel. A doping time greater than 4 seconds results in higher noise, because of a larger number of traps generated by the doping-induced defects. FIG. 2*b* shows the calculated transconductances of three devices with different doping profiles (FIG. 8), showing that the FET structure is important for the high sensitivity: shown are low doping (LD, uniform doping at ~10 $\mathrm{Ohm{\cdot}sq^{-1}}$ from the silicon-on-insulator substrate), selective doping (SD, light doping at ~$10^4$ $\mathrm{Ohm{\cdot}sq^{-1}}$ in the gate, and heavy doping in the drain and source), and heavy doping (HD, uniform doping at ~$10^2$ $\mathrm{Ohm{\cdot}sq^{-1}}$). FIG. 2*c* shows: i Output characteristics of the n-channel FET in the linear region under different applied gate voltages; and ii Transfer characteristics of the FET under different drain voltages. The FET is in a depletion-mode, which is "ON" at zero gate voltage. It shows a high transconductance in the −100~100 mV regime. In the figures $V_d$ denotes the drain voltage and $V_g$ denotes the gate voltage. FIG. 2*d* shows: i Output characteristics of each FET in a 10-FET array. The inset shows the distribution of the FETs' conductance; ii, Transfer characteristics of each FET in the array. The inset shows the distribution of the FETs' transconductance. FIG. 2*e* shows comparisons of the 10-FET array's (i) conductance and (ii) transconductance before and after compressive buckling, illustrating that the buckling process has no impact on the FETs' electrical performance. The circles and error bars show the mean and standard deviations of the ten FETs' properties. FIG. 2*f* shows a comparison of the FETs' electrical conductance with and without a saline solution on the gate terminal, showing minimal current leakage of the FETs. The circles and error bars show the mean and standard deviations of the ten FETs' properties. The ionic solutions induce slightly more carriers (due to surface absorbed $H^+$) and thus slightly higher conductance in the conduction channel. FIG. 2*g* shows the temporal response of the FETs to gate signals: i, A 100 mV pulse (rising/falling (R/f) times: 0.1 ms; duration 1 ms) is applied to the gate. The corresponding conductance of the FET (black curve) exhibits changes coincident with the input signal without any noticeable delay; ii, Repeated characterization of the same FET 10 times with an input gate signal at 100 kHz sampling rates (0.01 ms resolution). The FETs show no observable jitter (<0.01 ms) in the data acquisition system and iii, The FET's conductance is reliable and independent from the rising/falling times of the input signals.

As FIG. 2 illustrates, by tailoring the doping time, we can precisely control the sheet resistance and thus doping concentrations in different regions of the FET, leading to a selectively doped $N^+NN^+$ structure. The $N^+NN^+$ structure is important for high sensitivity and operational reliability at zero gate bias because it operates at the "ON" state with zero gate bias, which avoids the irreversible faradaic reactions induced by the high gate voltage during signal recording with other FET structures (FIG. 8). For the FET geometry in FIG. 1*d*, we optimized the doping time to get the highest sensitivity-to-noise ratio (see FIG. 2*a*). The sensitivity-to-noise ratios of the selectively doped FETs are much higher than those of FETs with low uniform doping (i.e., only background doping from the substrate) or high uniform doping (see FIG. 2*b* FIG. 8).

Figure 15A:
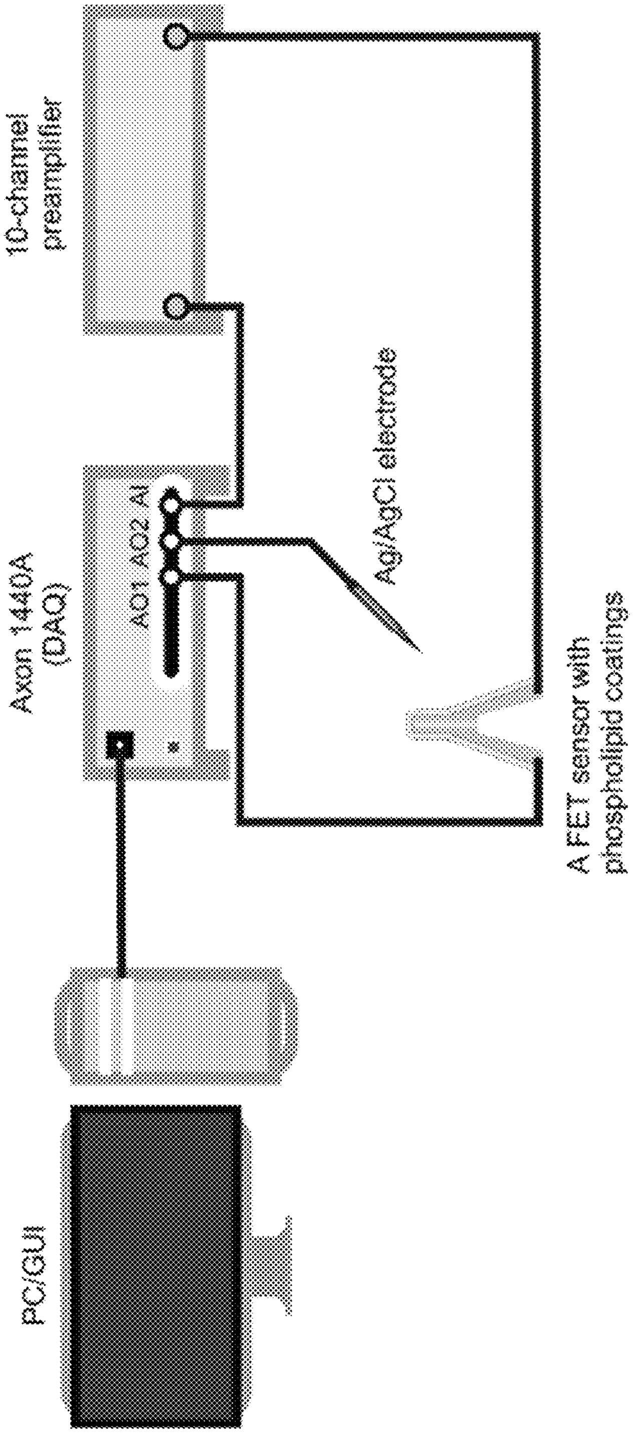
FIG. 15A-15C show an experimental setup for recording cellular electrophysiology by the arrayed FETs.
Figure 15B:
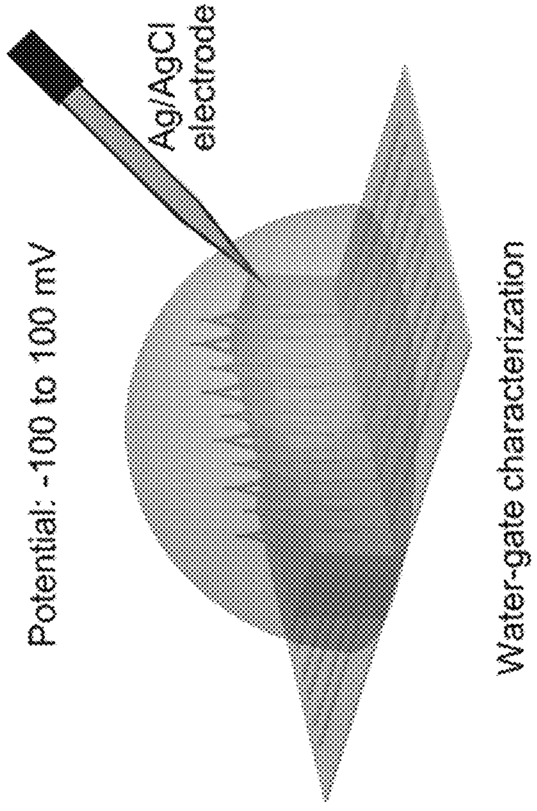
Figure 15C:
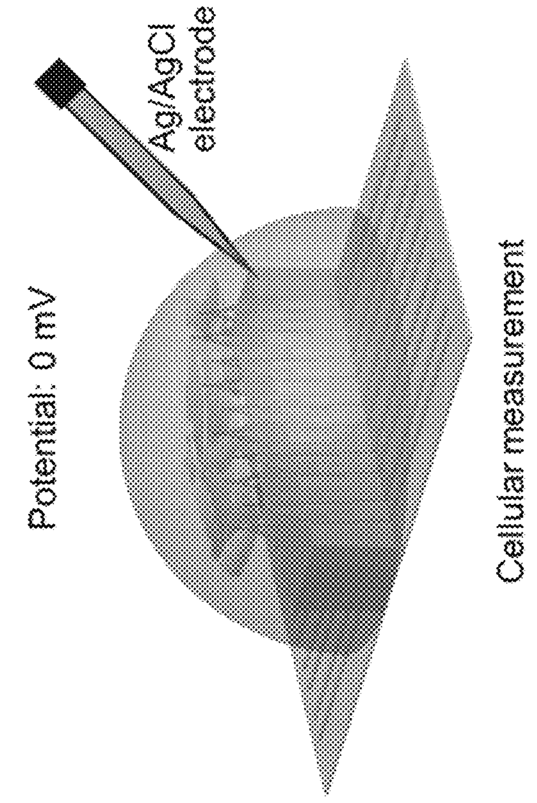

We characterized the transport behavior of a 10-FET array in a water gate configuration (see FIG. 15). The output characteristics of an FET in the array illustrate its typical n-channel properties under various gate biases (FIG. 2*c-i*). The FET exhibits large conductance under various drain potentials at zero gate bias (FIG. 2*c-ii*), which is important for sensing cellular electrophysiological signals. The 10 FETs have an average conductance of 0.9±0.3 μS (FIG. 2*d-i*) and an average transconductance of 7.5±2.0 $\mu S{\cdot}V^{-1}$ (FIG. 2*d-ii*). The transconductance is greater than, and its relative standard deviation (i.e., coefficient of variation) is comparable to those of devices synthesized by bottom-up methods, which can be attributed to the high material quality of the device-grade Si and controllable fabrication process. The high performance allows the FETs to record low-amplitude sub-threshold cellular signals.

Figure 9A:
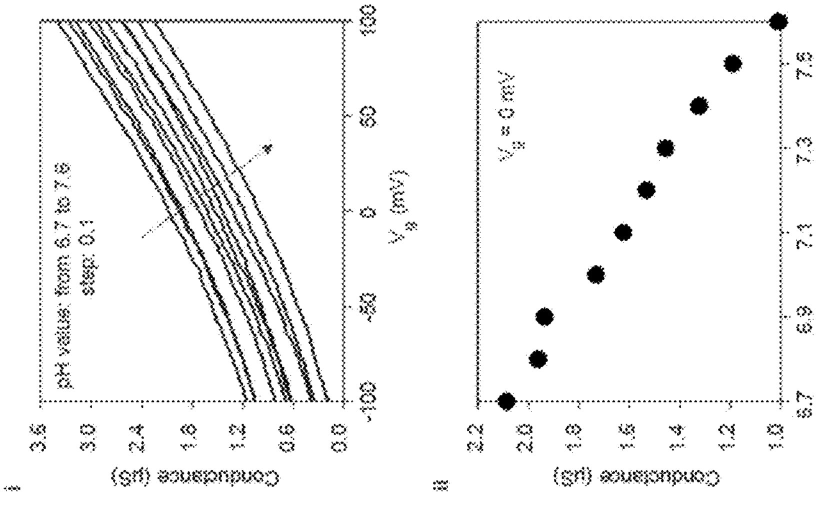
FIG. 9A-9C illustrates the FETs' reliability tests under various conditions.
Figure 9B:
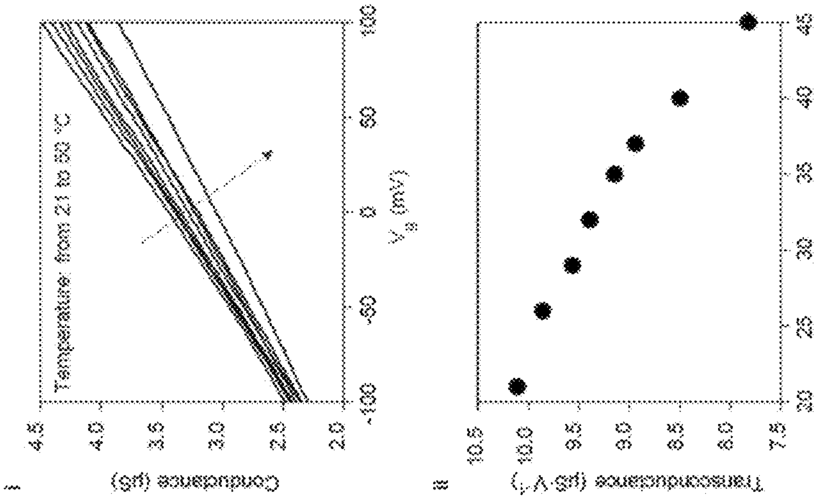
Figure 9C:
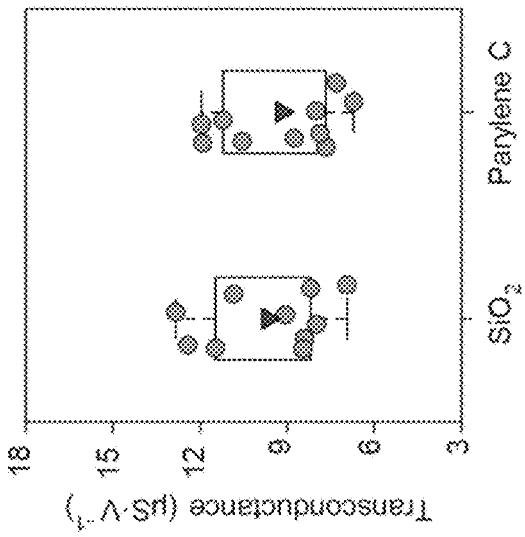

After transforming from 2D to 3D, the 10 FETs showed a <0.2% variation in conductance and a <0.5% variation in transconductance (FIG. 2*e*), which validates the 3D FET's mechanical and electrical robustness. The 10 FETs exhibit comparable conductance before and after immersion in saline solution (FIG. 2*f*), showing neglectable changes in surface charges and minimal current leakage through the insulation layers. Moreover, the FETs exhibit consistently high sensitivities over a range of pH (from 6.7 to 7.6) and temperatures (from 21 to 50° C.), demonstrating their tolerance for chemical and thermal conditions in various cell culture media. The stability of the FETs is primarily attributed to the insulating gate dielectric materials. The type of gate dielectric materials will not affect the FETs' sensitivity (FIG. 9).

To ensure we can record the dynamic and transient ionic signals, we characterized the temporal response of the FETs. Pulse signals with a rise and fall time of 5 ns-50 ms were applied on the gate, and the channel signals of the FETs were recorded. The FET shows a short intrinsic response time to the input gate signals (≤712 ns), which is shorter than previously reported values due to its optimized small gate dielectric thickness. Due to the limit of the sampling rate of the digitizer (100 kHz maximum), the entire recording system has a temporal resolution of 0.01 ms, and thus the recorded channel signal shows a response time of 0.1 ms (FIG. 2*g-i*), which is sufficient to accurately record common ionic activities (typically >1 ms). Note that there is a capacitance-induced overshoot on the rising and falling edges of the response. The capacitance was from the electrode-ionic solution coupling, which could be neglected in cellular measurements because of the localized coupling between the membrane potential and the FET. In repeated measurements, the start and saturation times of the FET's response remain unchanged, showing that it can accurately follow the rapid input signals (FIG. 2*g-ii*). With different rising/falling times (0.1-50 ms) of the input signal, the conductance changes are within ~1.5%, which is typical for FETs (FIG. 2*g-iii*). Additionally, the FETs can faithfully record simulated cellular action potentials resembling those produced by pacemaker and non-pacemaker cardiomyocytes, with frequencies over 1~10 Hz, covering the typical firing frequencies of electrogenic cells. Additional discussions related to the response time of the FET will be presented below.

We coated a phospholipid bilayer on the FETs to facilitate the internalization into the cells and to enable good sealing at the FET-cell interface. Either small unilamellar vesicles of exacted red blood cell membranes or synthetic phospholipid bilayer materials (1,2-dimyristoyl-sn-glycero-3-phosphocholine) were used. Fluorescent images confirm the successful coating of the phospholipids on all FETs before and after buckling. To illustrate the internalization process, when the FET is near the cell, it records the membrane potential extracellularly. The equivalent circuit model reveals an attenuated signal ($V_c$) due to the membrane impedance ($R_m$ and $C_m$) and the shunt via the small spreading resistance ($R_s$). As the FET approaches the cell, the phospholipid coating spontaneously fuses with the cell membrane with minimal invasiveness to the cell, realizing intracellular sensing. The tight interfacial sealing maximizes the spreading resistance $R_s$ (i.e., minimizes leakage current).

Recording Intracellular Action Potentials

Full-amplitude signals contain quantitative information on ionic activities inside the cell. The full amplitude depends on many factors, including the type, culture conditions, and physiological status of the cell. The FET arrays in this work can measure full-amplitude signals comparable to those acquired by the whole-cell patch-clamp.

Cell viability test results proved that neither the construction materials nor the signal recording of the FET showed cytotoxicity towards HL-1 cardiac muscle cells. A $Ca^{2+}$ spark assay confirmed the HL-1 cells' electrophysiological activities. Full-amplitude action potentials were stably recorded by both the FET and a whole-cell patch-clamp.

FIG. 3 shows intracellular recordings and validations on single cardiomyocytes. In particular, FIG. 3*a* shows that periodic spikes can be recorded from different HL-1 cells by different FETs (top panels). The results are validated using the whole-cell patch (lower left panel). Enlarged regions of the recordings by the FET and the patch-clamp represent typical pacemaker action potentials of the HL-1 cells (lower right panels). The mean and standard deviation of the action potentials measured by the FET are 121.4±1.3 mV, which are close to the 122.0±4.0 mV measured by the patch-clamp, showing the FET's capability for recording full-amplitude action potentials. Sub-threshold signals (e.g., cell membrane oscillations of 5~15 mV) are captured in the recordings of cells 3 and 4, as highlighted by the black triangles. FIGS. 3*b* and 3*c* show intracellular recordings from primary cells including neonatal mouse atrial cardiomyocytes (FIG. 3*b*) and adult mouse ventricular cardiomyocytes (FIG. 3*c*). The relatively larger noise in FIG. 3*c* is induced by the contraction of the adult mouse cells during measurements. In some spikes in FIG. 3*c*, an upstroke can be observed during repolarization, as marked by the asterisks, indicating abnormal $Ca^{2+}$ influxes, which is also likely caused by the contraction. FIGS. 3*d* and 3*e* show pathological studies of the HL-1 cells by modulating ionic concentrations in the culture solutions. Both the hyperkalemia (FIG. 3*d*) and the hyponatremia cells (FIG. 3*e*) exhibit a decreased signal amplitude, a shortened action potential duration (APD), and a longer refractory period compared to the normal cells, as recorded by the FET. The recorded action potentials recover when the culture solutions are switched back to the Tyrode's solution. FIGS. 3*f* and 3*g* show the effects of ion channel blocking drugs on (i) action potential morphologies of HL-1 cells recorded by the FET and (ii) corresponding quantitative analysis. Cells exposed to 100 nM nifedipine (FIG. 3*f*) exhibit a lower spike amplitude and shorter APD50 or APD90 (action potential duration at 50% or 90% repolarization, respectively). The cells repolarize very fast because nifedipine is an L-type $Ca^{2+}$ channel blocker, which diminishes the influx of $Ca^{2+}$ into the cells. FIG. 3*g* shows that 10 μM tetrodotoxin acts on the rapid $Na^+$ channels, reducing the spike amplitude and thus shortening the repolarization duration. Error bars are standard deviations of 20 recorded action potentials.

The amplitudes, morphologies, and firing patterns of the acquired potentials by the FET and a whole-cell patch-clamp highly correspond to each other, showing the ideal coupling and faithful recording of the intracellular signals by the FETs. The minor discrepancies are within the standard fluctuations due to differences in cellular physiology and measurement setups. Importantly, the FETs could record sub-threshold signals, due to their high sensitivity-to-noise ratios. Primary cells exhibit natural and primitive electrophysiological characteristics akin to their intrinsic states in live animals. The FET could record action potentials from spontaneously firing neonatal and adult mouse cardiomyocytes with results similar to those by the whole-cell patch (see FIGS. 3*b* and 3*c*). The amplitude of each spike in the same recording fluctuates due to the contractile movements of the cells.

The phospholipid coating on the FETs plays a crucial role in the intracellular recording. Continuous intracellular signal recordings on HL-1 cells could be extended to over 70 seconds (FIG. 24), the longest reported by an intracellular FET sensor. A phospholipid coating could last through three times of cell insertion before re-functionalization was needed to fulfill a stable intracellular recording. Without the phospholipid coating, the FET could still mechanically rupture the cellular membrane and access the cytoplasm sometimes. However, those recordings showed higher noise levels, lower signal amplitudes, and fluctuating signal baselines due to the highly unstable FET/cell interface. Signals recorded without phospholipid gradually transformed from intracellular to extracellular, probably because the ruptured cell membranes fused again and expelled the FET.

Figure 3A:
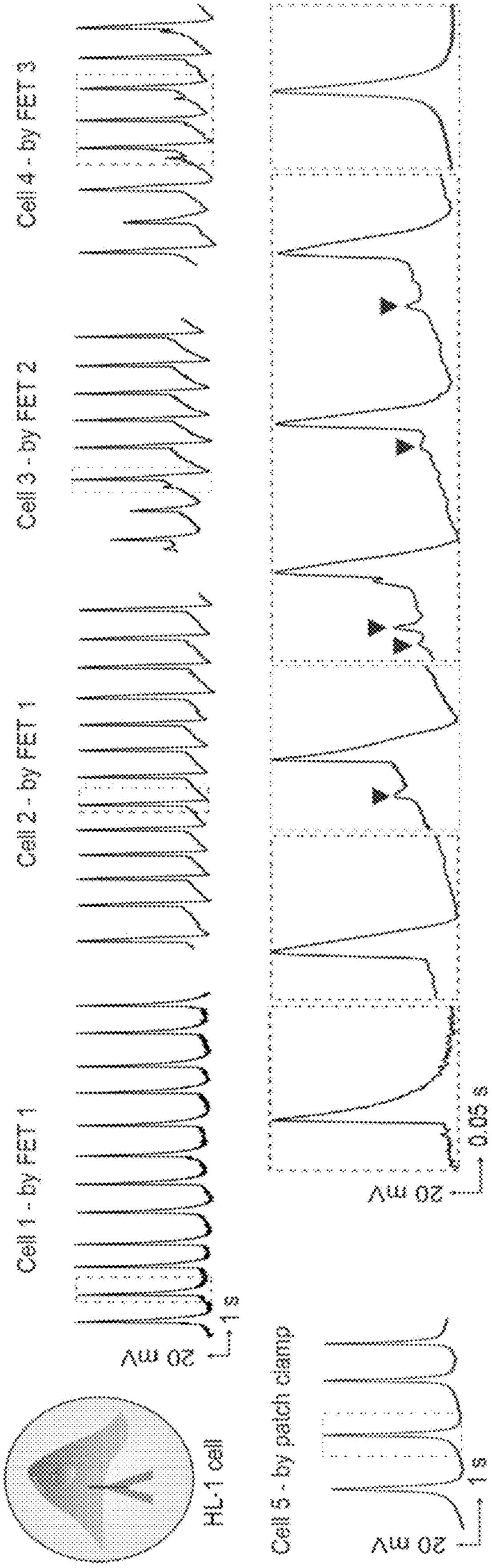
FIGS. 3*a*-3*g* show intracellular recordings and validations on single cardiomyocytes.
Figure 3C:
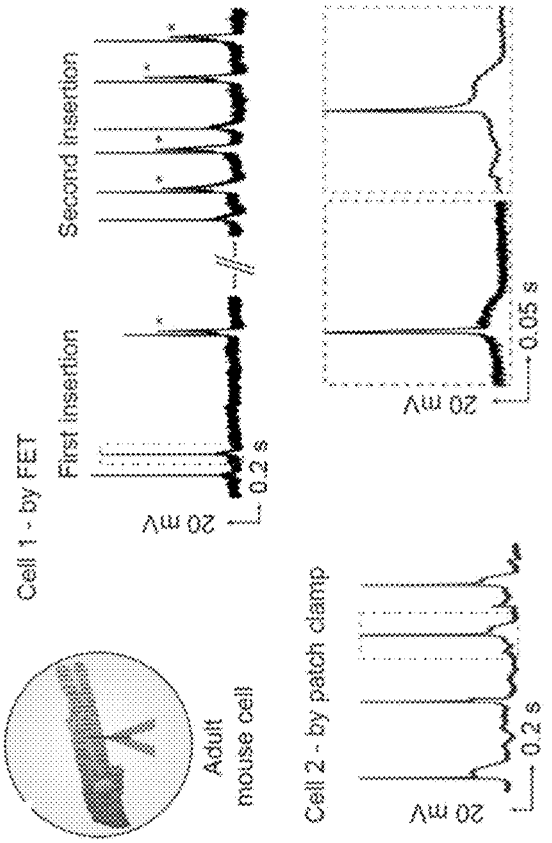
Figure 3B:
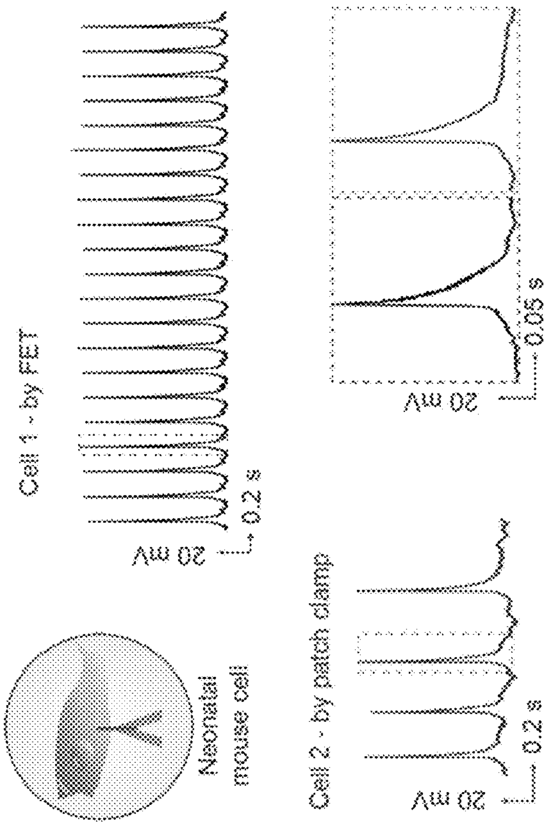
Figure 3D:
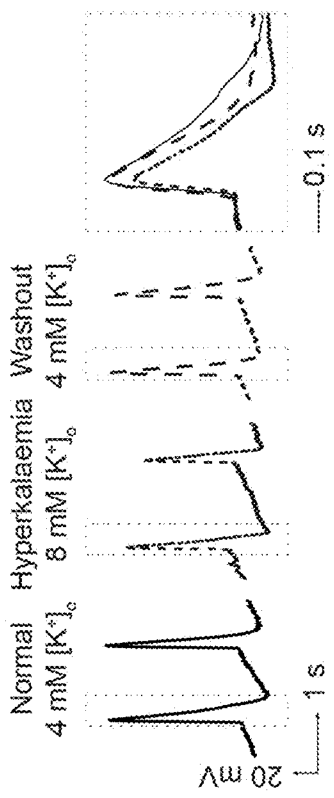
Figure 3E:
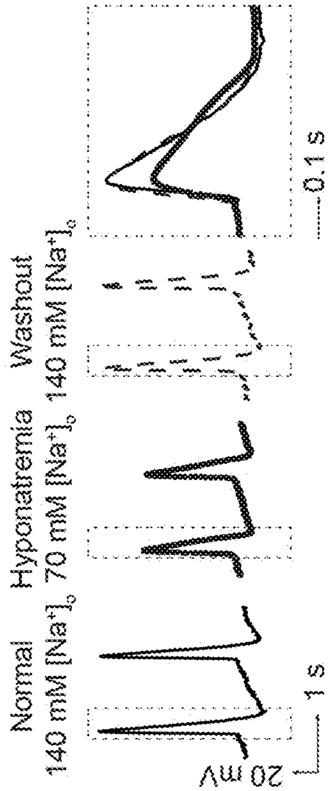
Figure 3F:
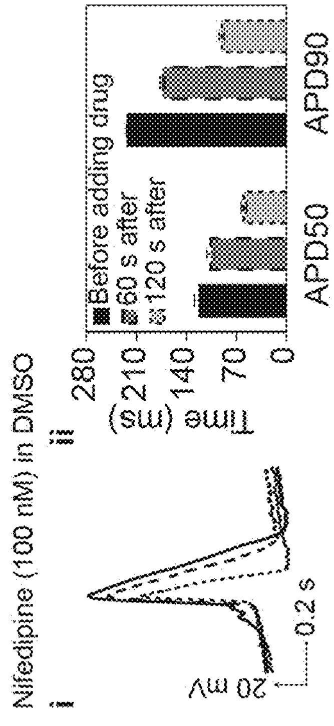
Figure 3G:
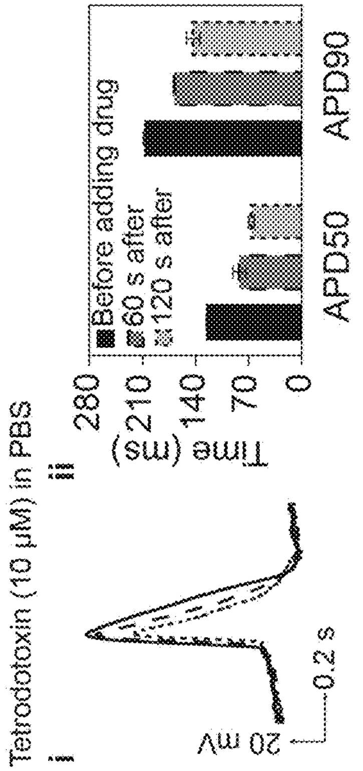

We tested the FET performance by verifying the HL-1 cells' response to extracellular solution composition and ion channel blocking drugs. FIGS. 3*d* and 3*e* show the effect of hyperkalemia or hyponatremia on the recorded electrophysiological behaviors of cardiomyocytes, including the beating rhythm, resting membrane potential, and action potential duration. Abnormally high potassium or low sodium ion concentration would vary the cell's action potential shape by shortening the duration and decreasing the amplitude. FIGS. 3*f* and 3*g* show the measured responses of HL-1 cells to ion channel blockers with modulated action potential amplitude and duration. The results show that nifedipine or tetrodotoxin lowers the amplitude and reduces the action potential duration at 50% or 90% repolarization (APD50 or APD90; data listed in Table 1). The effect is reversible after the extracellular solution was swapped back to normal compositions.

Recording Intercellular Signal Conductions

Figure 4B:
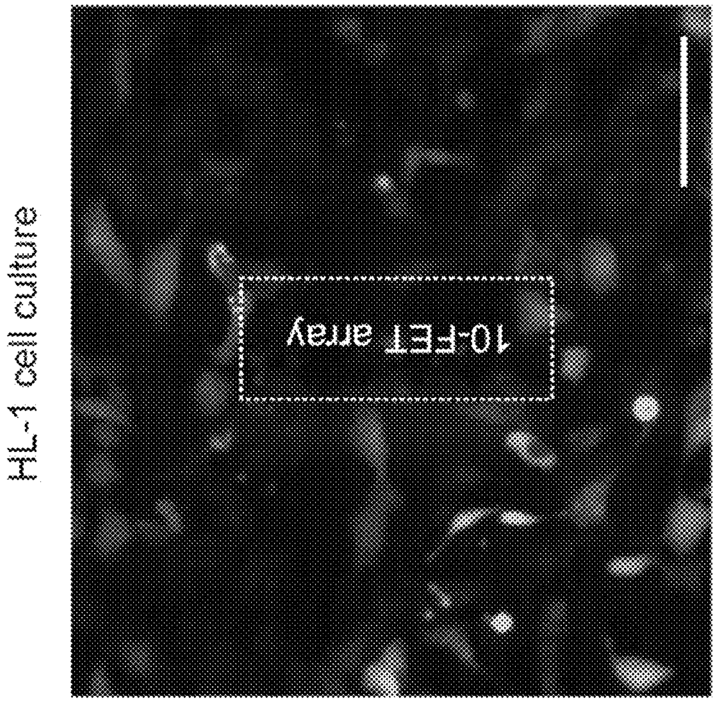
FIGS. 4*a*-4*f* show intracellular recording on a 2D HL-1 cell culture by a 10-FET array.
Figure 4A:
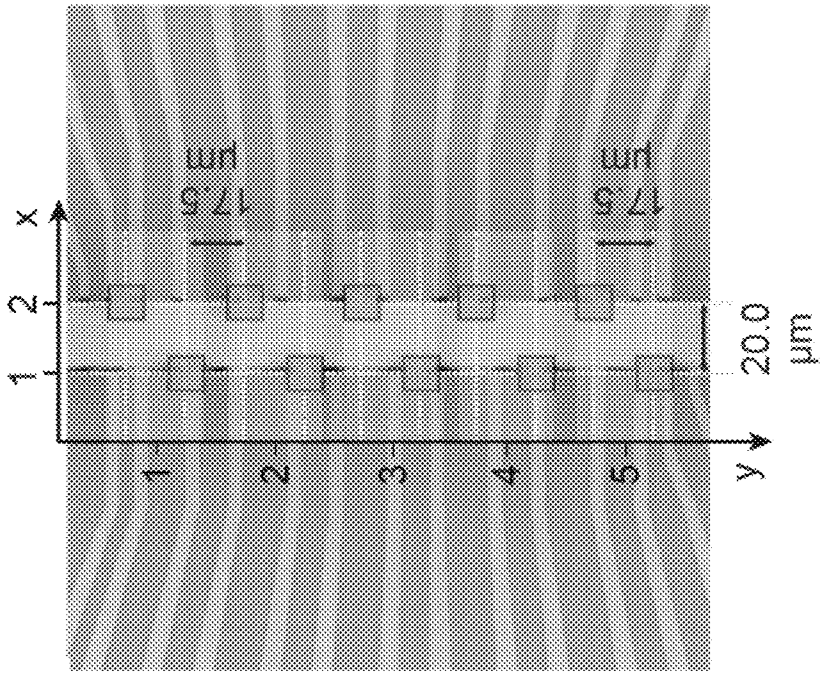

We used a 3D 10-FET array with well-defined spacing to record intercellular signal conductions, which is related to the electrical coupling states between cells. FIG. 4 shows intracellular recording on a 2D HL-1 cell culture by a 10-FET array. In particular, FIG. 4*a* shows a schematic top view of a 10-FET array. The spacing between each FET is accurately defined by lithography. A coordinate system is used to denote the position of each FET, as indicated by the squares. When a common electrical pulse is provided, the FETs exhibit the same characteristics, and the electrical signal delay between any two channels is no greater than 0.01 ms, suggesting that the system-induced electrical delay is negligible. A layer of spontaneously firing HL-1 cells cultured on a PDMS sheet was laminated on the FET array. FIG. 4*b* shows a fluorescent image of a 10-FET array interfacing with a 2D culture of HL-1 cells (average size ~50 μm), stained by Fluo-4 am dye. During the measurement, only the FETs are interfacing with the cells, while the areas around them are not contacting with the cells The scale bar in FIG. 4*b* is 100 μm. We used electrical stimulation to regulate HL-1 cells' firing patterns to study the direction and velocity of intercellular signal conduction.

Figure 4D:
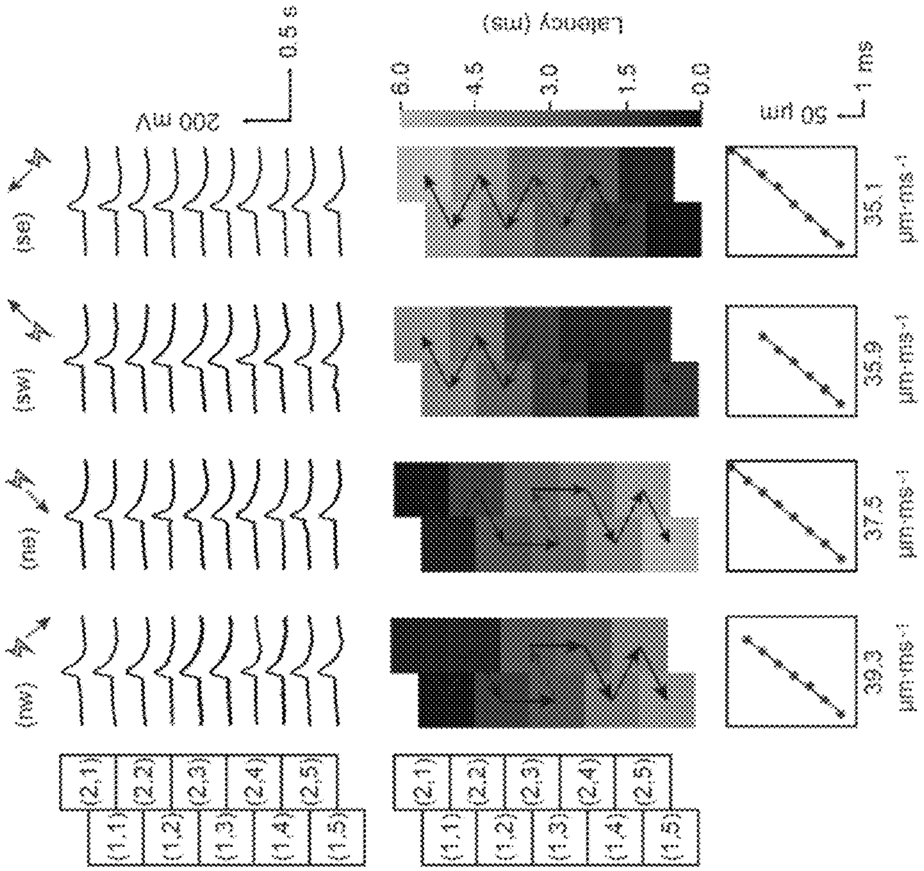
Figure 4C:
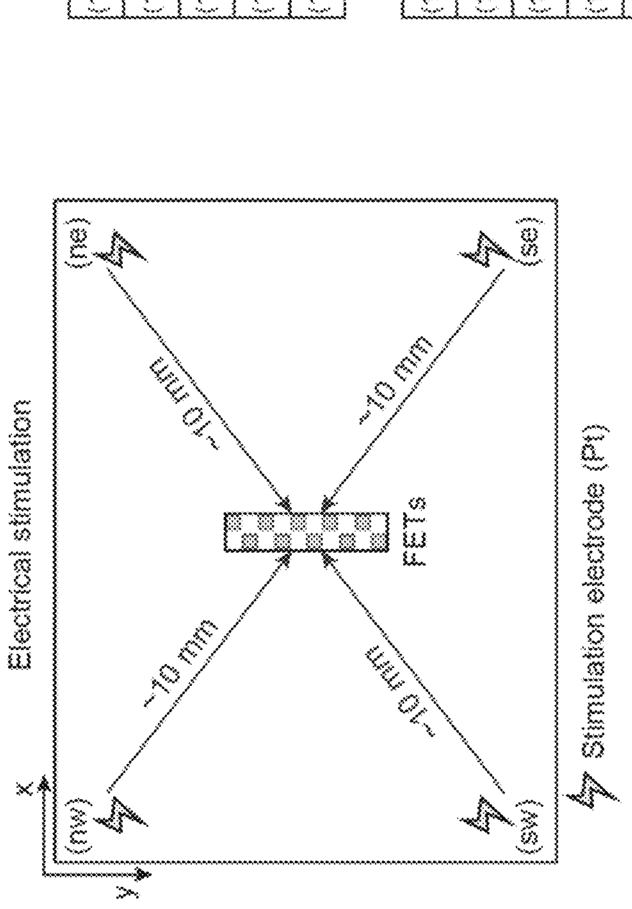
Figure 35:
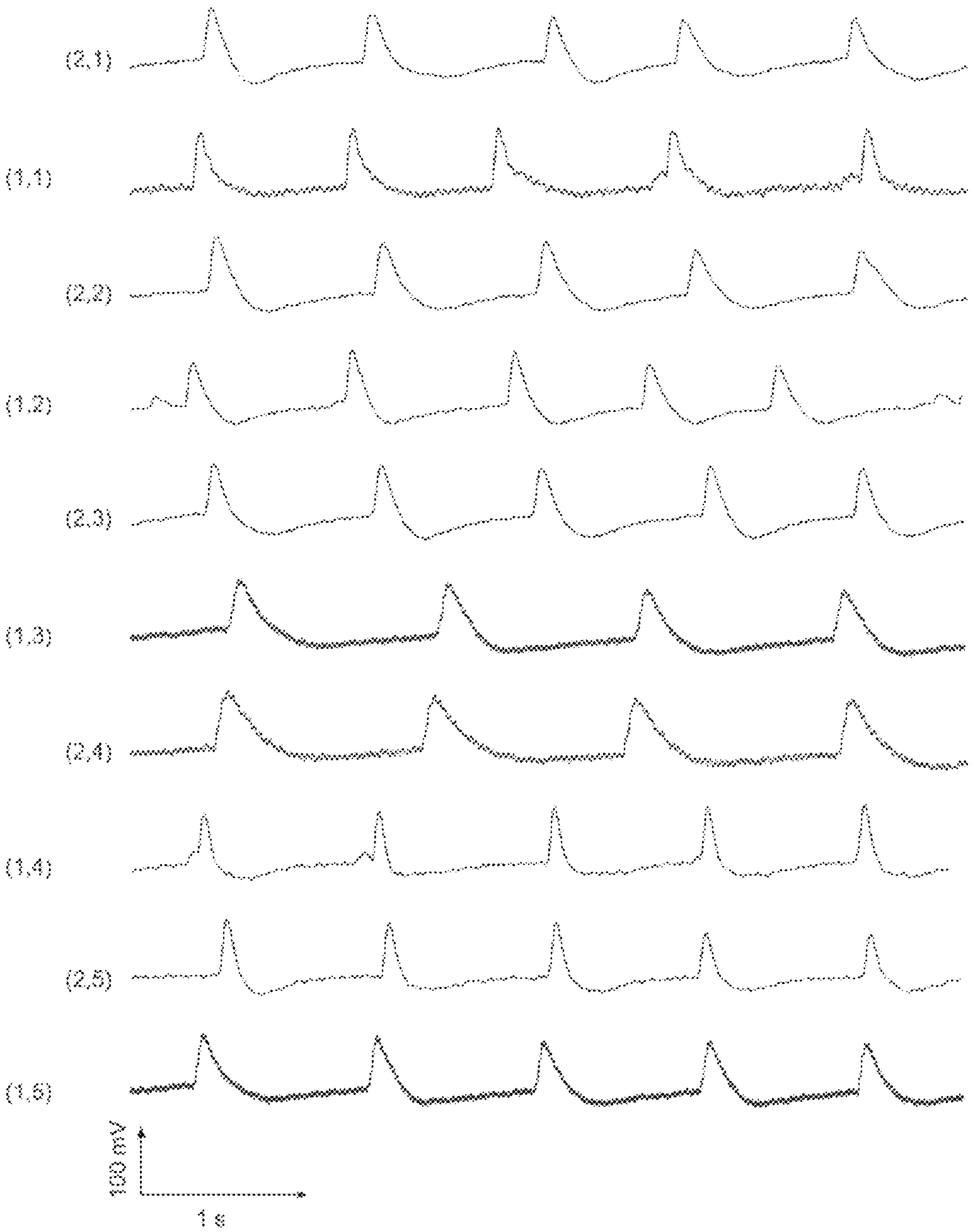
FIG. 35 shows recordings of spontaneous firing HL-1 cells by a 10-FET array.

Four electrodes were placed in the cell culture on the four corners, and a stimulation pulse was applied to one electrode in each measurement. FIG. 4*c* shows the schematic setup for stimulating the HL-1 cells, with four Pt electrodes placed in the cell culture on each corner. A stimulation pulse was applied to a single electrode in each measurement. We used biphasic pulses, so the net injection current was zero. The frequency, width, and amplitude of the pulses were 1 Hz, 1 ms, and 1 V, respectively, to effectively pace the cells. Under electrical pacing, spontaneous arrhythmic action potentials are suppressed, and the corresponding recorded cellular signals are shown in FIG. 4*d* and FIG. 35 and FIG. 10. FIG. 4*d* shows simultaneous intracellular recordings from a 2D HL-1 cell culture under electrical pacing at different orientations to the FETs. All FETs recorded periodic intracellular action potentials of 95~116 mV. Heat maps illustrate the latency of action potentials among the cells. Arrows indicate the possible signal conduction paths among cells. In all measurements, the signal first arrives at the cell closest to the stimulation electrode and then transmits subsequentially to the neighboring cells. The average intercellular conduction velocity is 35.1~39.3 $\mu m \cdot ms^{-1}$. Regardless of the stimulation orientation to the FETs, the intracellular signal conduction is always from (1,3) to (2,3).

We calculate the signal latencies between the FETs by cross-correlating the recorded action potential profiles (see Table 2). A heat map visualizes the action potential conduction direction among the cells, as indicated by the arrows in FIG. 4*d*. Based on the conduction latencies and the predefined distances between the FETs, the intercellular signal conduction velocity is calculated to be 35.1~39.3 $\mu m \cdot ms^{-1}$, comparable with the results from other studies on HL-1 cells. Long-period recordings show the robustness of the measurements by the FET array (see FIG. 37 and Table 3).

Fast Signal Conductions within a Cell

Intracellular signal conduction in cardiomyocytes corresponds to various forms of subcellular ionic activities. However, it is challenging to record intracellular conductions in cardiomyocytes because it is difficult to interface two or more patch clamps with one cardiomyocyte. Also, the short signal latency inside the cardiomyocyte can be overshadowed by the intrinsic delay of the existing recording systems.

Figure 4F:
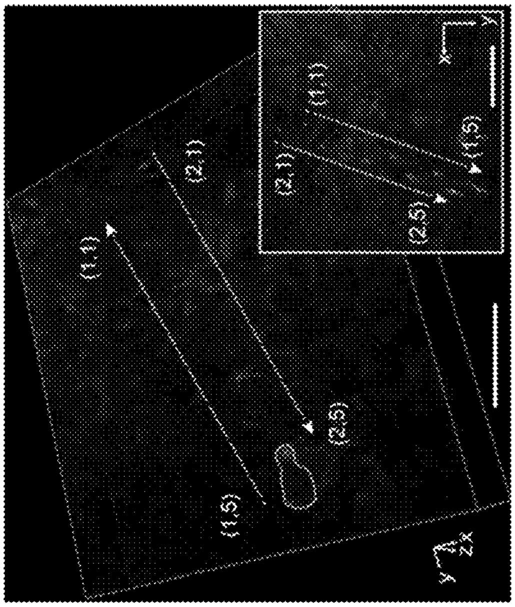
Figure 4E:
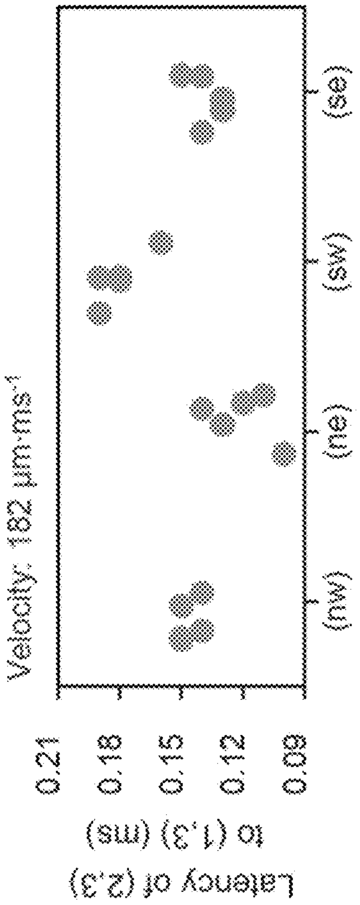
Figure 38B:
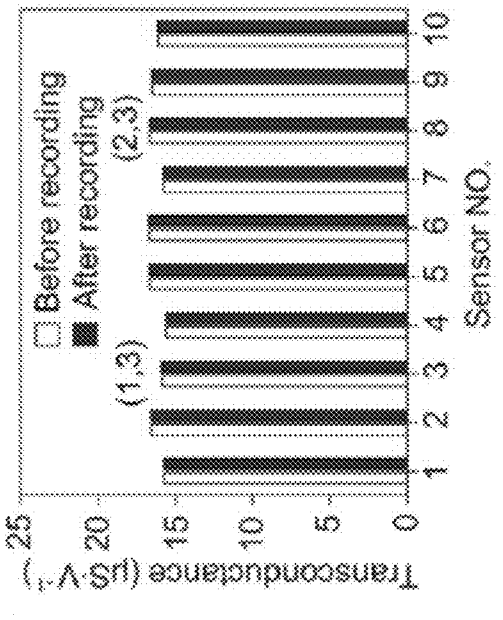
FIGS. 38A-38F show a justification of the intracellular signal conduction inside a HL-1 cell.
Figure 38A:
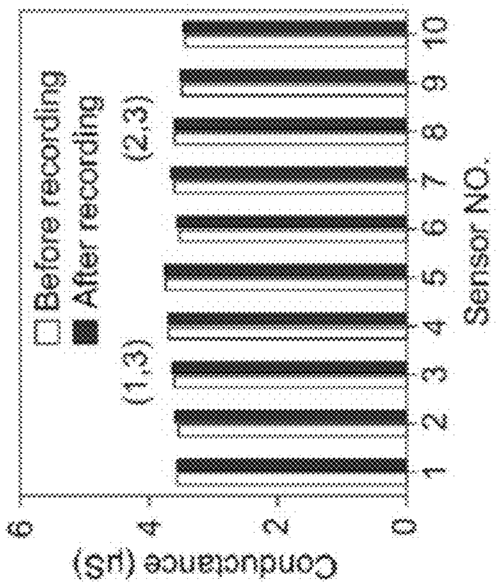
Figure 38C:
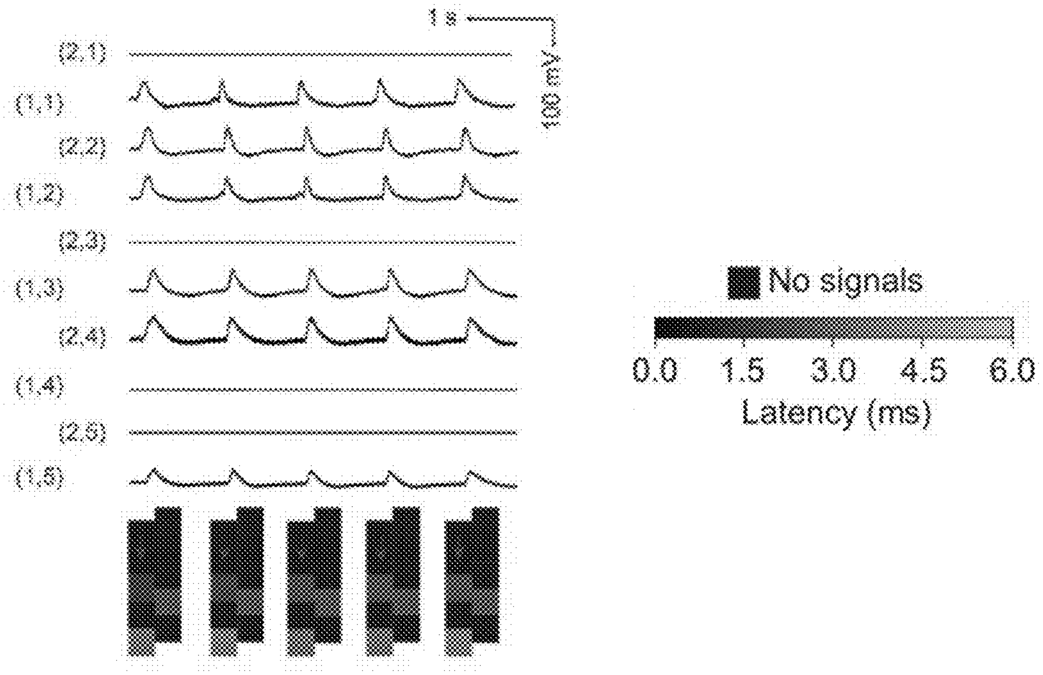
Figure 38D:
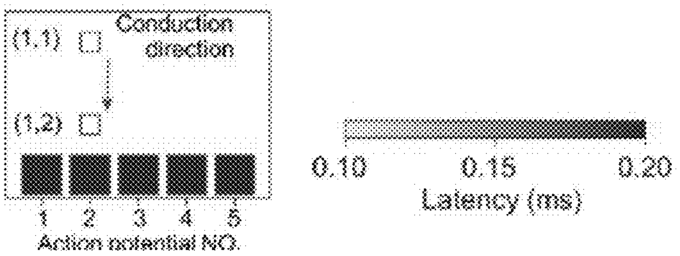
Figure 38E:
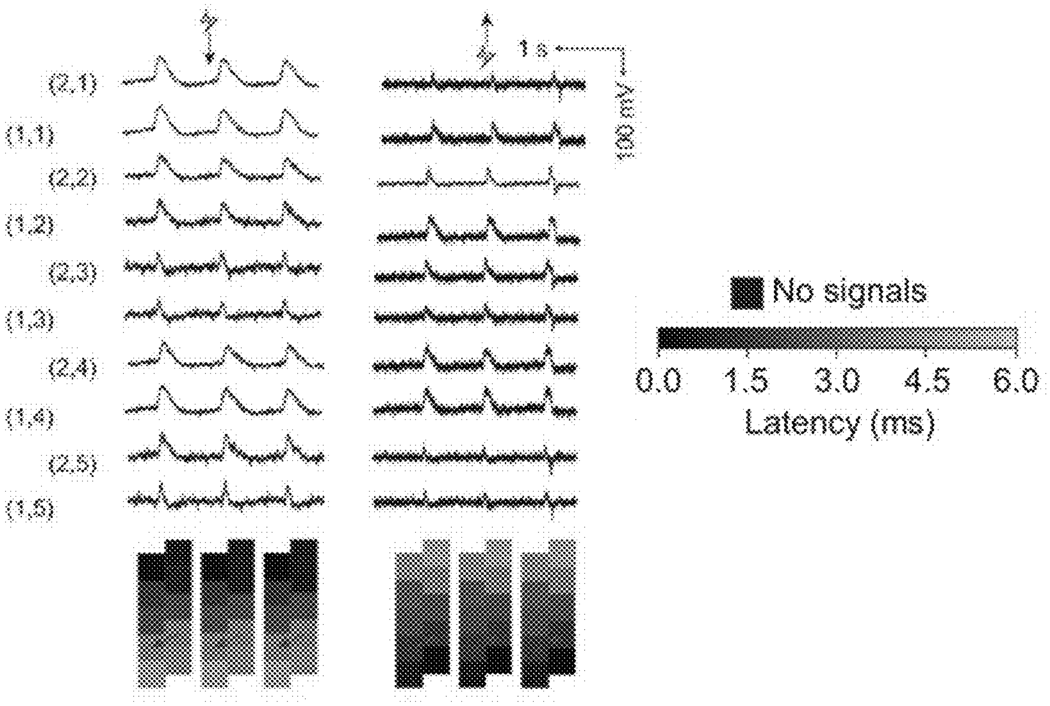
Figure 38F:
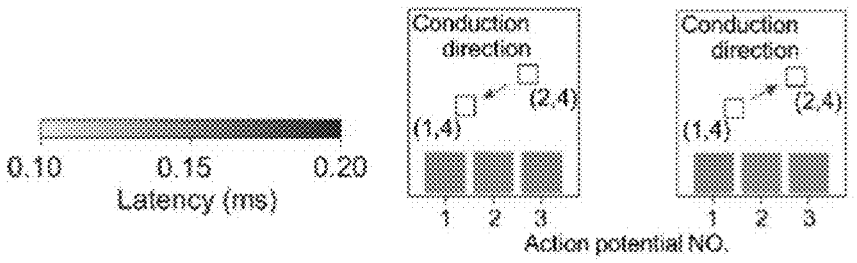
Figure 39A:
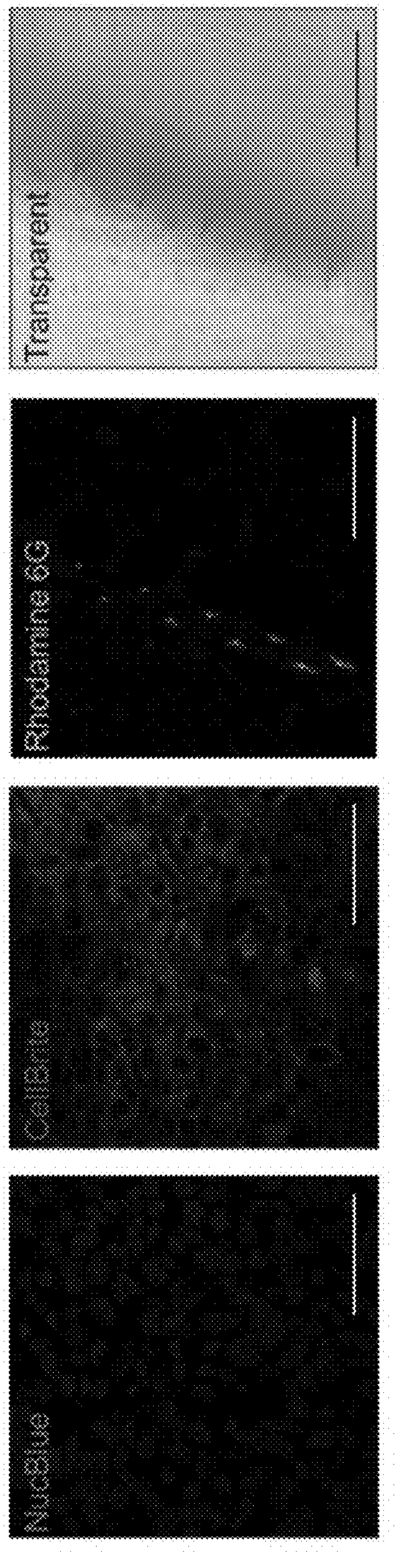
FIG. 39A-39E show fluorescent images and simultaneous action electrical recordings of an FET array and HL-1 cells.
Figure 39C:
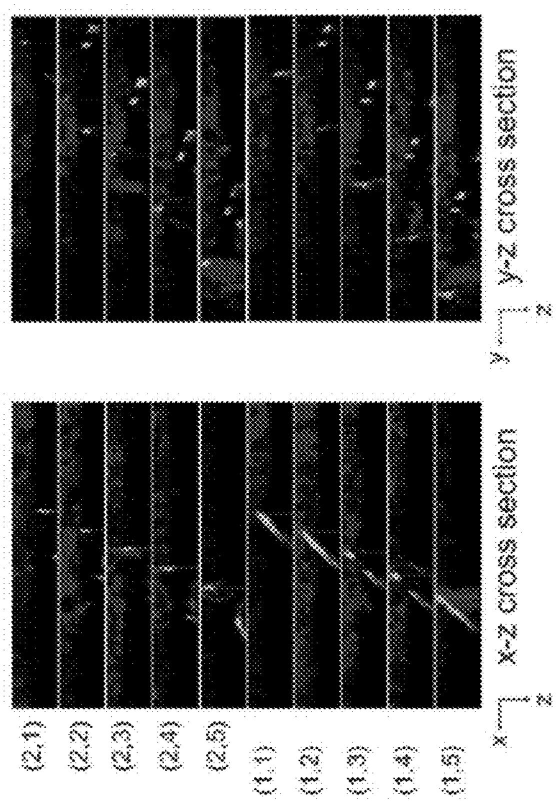
Figure 39B:
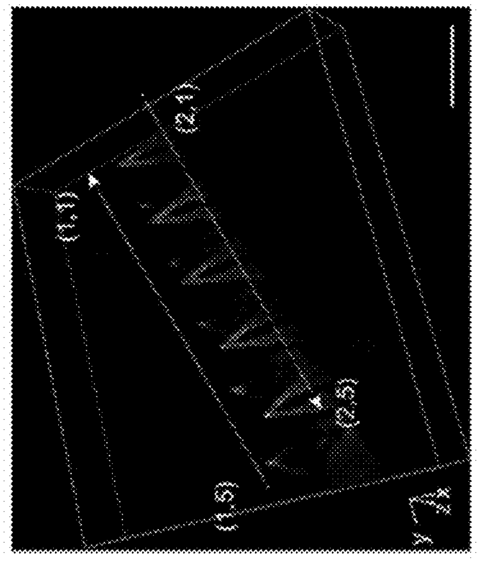
Figure 39E:
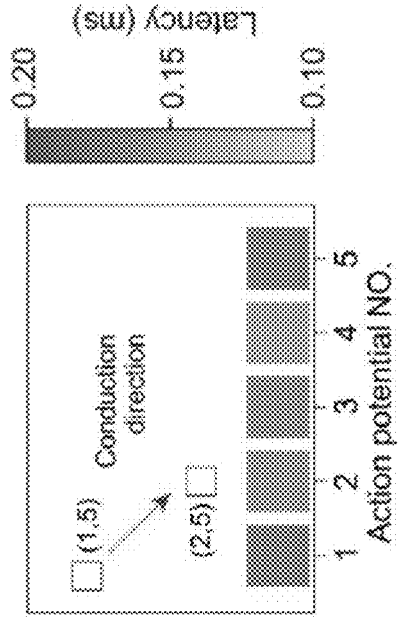
Figure 39D:
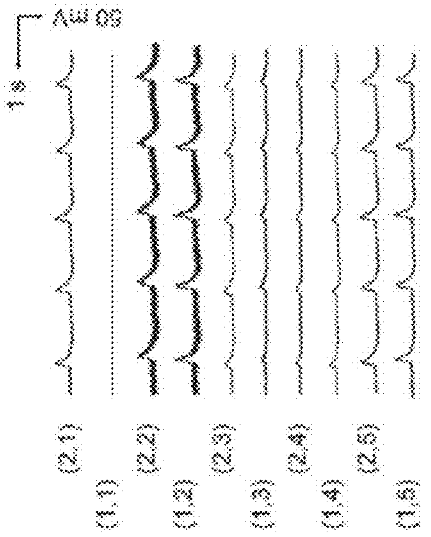
Figure 43A:
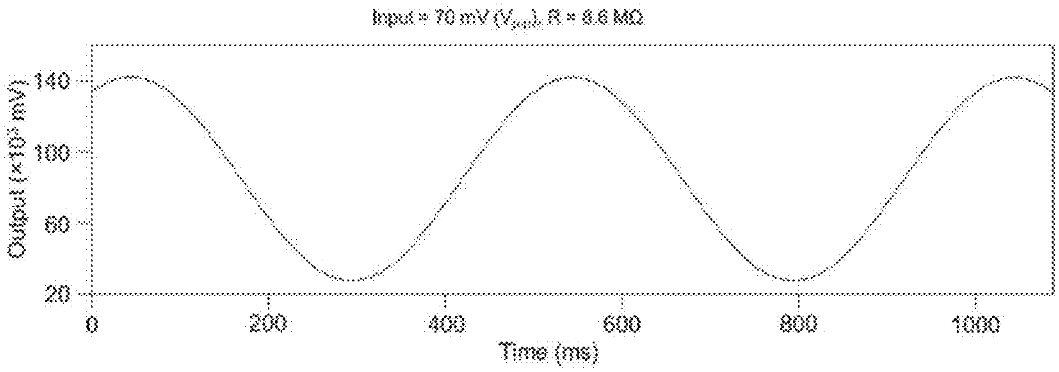
FIG. 43A-43C show amplification tests of the DDC264.

In FIG. 4*d*, regardless of the orientation of the stimulation electrode, we found the latencies between the FETs at (2,3) and (1,3) to be always ranging from 0.10 ms to 0.20 ms (Table 2), much shorter than those between the other FETs. Given the distance between these two FETs (26.6 μm), the conduction velocity is calculated to be 182 $\mu m \cdot ms^{-1}$, which is about five times the intercellular conduction velocity. FIG. 43*e* shows that the average and standard deviation of the latencies is between (1,3) and (2,3) calculated from the 20 action potentials in four orientations being 0.146±0.025 ms. The intracellular conduction velocity is 182$\mu m \cdot ms^{-1}$, which is about five times the velocity of intercellular conduction. To verify the measurement, we used the same 10-FET array to study a different HL-1 cell culture. This time, we found no signal conduction between the FETs at (2,3) and (1,3); but two other FETs, at (1,1) and (1,2), showed a ~0.18 ms latency (see FIGS. 38*c* and 38*d*). To triple check the measurement results, we used confocal microscopy to image live cells while simultaneously recording electrical signals. The results verified that two FETs were in the same cell. FIG. 4*f* shows confocal microscopy images illustrating a 3D view of FETs intracellularly interfacing live HL-1 cells. Inset is the corresponding top view. The images clearly show two FETs, (1,5) and (2,5), are interfacing the same cell, whose corresponding action potentials recordings are shown in FIG. 39*d*. The scale bars in FIG. 4*f* are 50 μm. Therefore, the signals we measured between these two FETs are intracellular conductions. The slight fluctuation in the intracellular conduction velocity may be because of the constantly changing ionic distributions within the cell. The intracellular conduction is much faster than the intercellular conduction because the latter is slowed down by ion diffusion processes via gap junctions between neighboring cells.

Additionally, in FIG. 4*d*, when the stimulation originated from different orientations relative to the FETs, the corresponding intercellular signal conduction direction would change. However, we found that the intracellular conduction direction was always from (1,3) to (2,3) in this case, independent of the directions of intercellular conduction, which was probably related to the positions of the FETs and cells' coupling with the neighboring cells (see FIGS. 38 and 40).

Intracellular Recording of 3D Tissue Constructs

Compared with 2D cellular cultures, 3D engineered tissue constructs better resemble natural organs in structural complexity and physiological functions. Therefore, they are excellent models for intracellular electrophysiology studies. However, existing devices have limitations in interfacing with 3D tissues; either they can only do extracellular sensing, or they have a uniform height for interrogating cells on a common plane only.

Figure 5A:
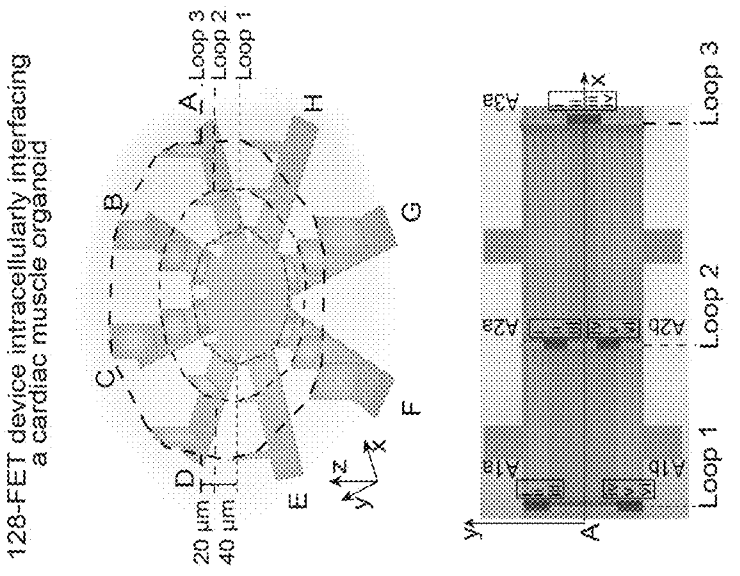
FIGS. 5*a*-5*f* show intracellular recording on a microtissue of neonatal rat cardiomyocytes by a 128-FET array.
Figure 5B:
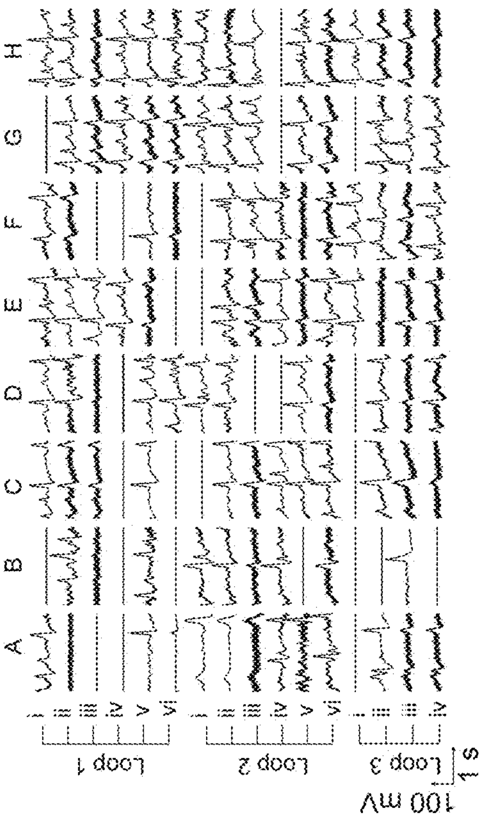
Figure 5C:
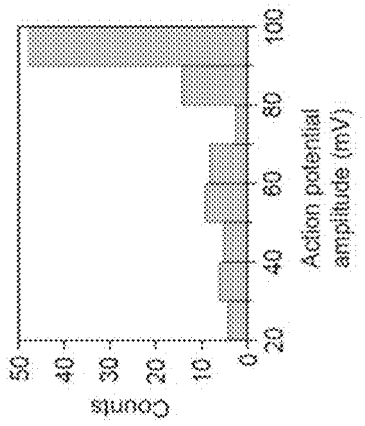

With tunable heights, the 3D FET sensor array provides a unique opportunity to study the electrophysiology of 3D tissues. To this end, we fabricated a stretchable 128-FET array distributed in 40 units of three different heights, capable of interrogating cells at three different depths in a 3D microtissue. FIG. 5 shows intracellular recordings on a microtissue of neonatal rat cardiomyocytes by a 128-FET array. In particular, FIG. 5*a* shows schematic diagrams of the 128-FET array distributed on eight arms. On each arm, there are 16 FETs in five units of different heights, distributed on three concentric loops (top panel). The 16 FETs' relative positions and assigned coordinates are labeled (bottom panel). Representative recordings by the array show intracellular action potentials in a 3D cardiac tissue, with 44% of the FETs being intracellular, 34% extracellular, and 22% inactive, where the intra- or extra-cellular signals were defined by the shape and amplitude of the signals In particular, FIG. 5*b* show representative recordings from the 3D cardiac tissue by the 128-FET array. Intracellular action potentials are recorded from all three loops on each arm. FIG. 5*c* shows a histogram of the spike amplitudes in FIG. 5*b*. (see also FIG. 45). The inactive FETs could be due to electrically inactive cells, or degraded performance of the FET, or nonideal FET-cell coupling (e.g., because of clastic response from the cytoskeleton).

Figure 5D:
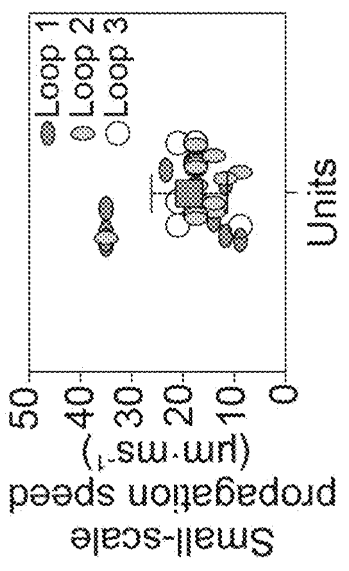
Figure 5E:
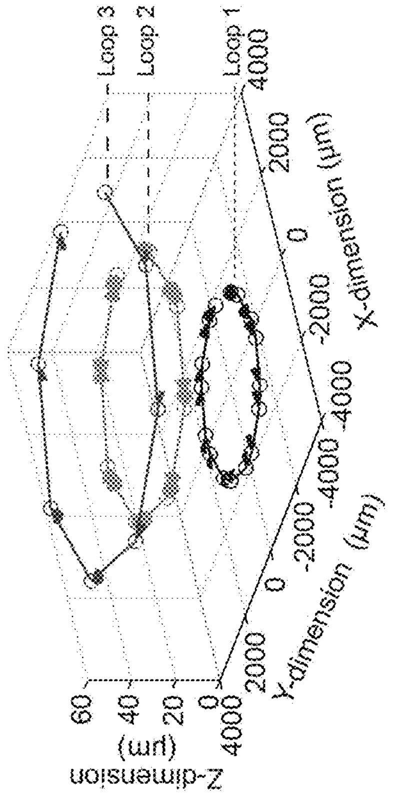
Figure 5F:
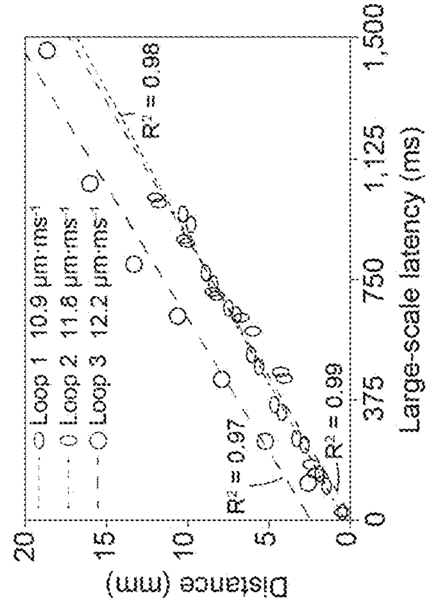
Figure 11:
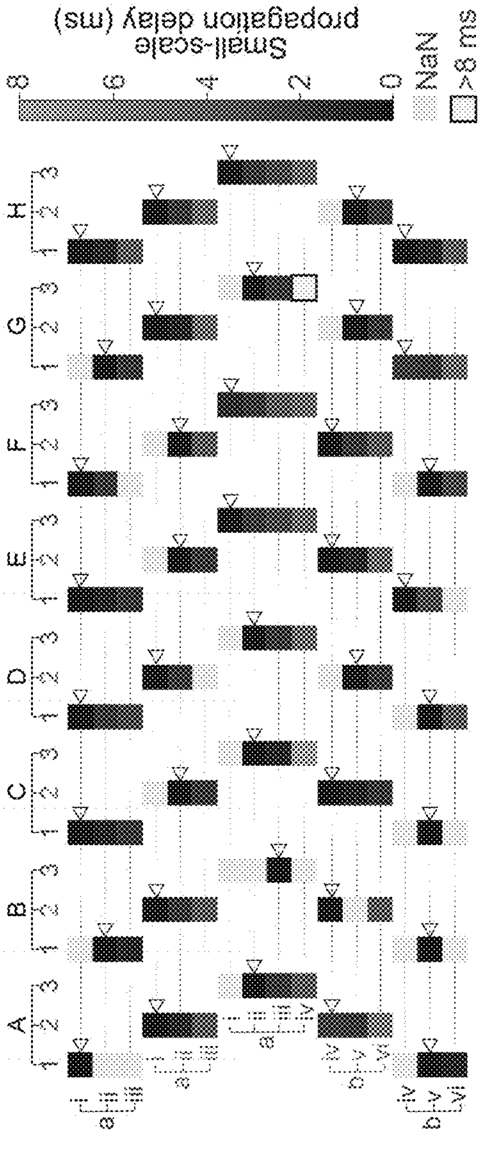
FIG. 11 shows small-scale signal conduction within the cardiac tissue by the 128-FET array.

We used the FETs in each unit to study small-scale intercellular signal conductions, whose velocities are calculated to be 18.8±7.5 $\mu m \cdot ms^{-1}$, consistent with reported values. FIG. 5*d* shows the small-scale intercellular signal conduction velocity measured within each unit. The average and standard deviation of the velocities within the 40 units are 18.8±7.5 $\mu m \cdot ms^{-1}$. (FIG. 11). We also leveraged the relatively large spacing between the 40 units of FETs to acquire the velocity of large-scale signal conduction. FIG. 5*e* shows a 3D visualization of the signal conduction in the whole 3D tissue construct. On all three loops, the signal conduction directions are consistent, beginning at arm H and then propagating to arm A. For each of the three heights, signals propagate clockwise among the units, forming a loop (see FIG. 5*a*). The calculated signal conduction velocities on the three different loops are 10.9 $\mu m \cdot ms^{-1}$, 11.8 $\mu m \cdot ms^{-1}$, and 12.2 $\mu m \cdot ms^{-1}$. FIG. 5*f* shows a linear fit of the intercellular signal conduction velocity across the units in each loop. The calculated large-scale conduction velocities are generally slower than those small-scale within each unit, because we assume the signal conduction path is linear from point to point on the large-scale; the actual path is likely to follow a zig-zag pattern, depending on the cells' relative positions and their electrical coupling states.

Fabrication of the 3D FET Sensor Arrays

In some embodiments the FET arrays were fabricated by the compressive buckling technique. The 2D structure contains silicon FETs, gold electrodes by sputtering, as well as two polyimide layers and an SU-8 mechanical supporting layer by spin casting. The shapes and patterns of each layer were defined by lithography and reactive ion etching. The overall fabrication process included four main steps: Si doping to generate the FETs, transfer printing of the FETs on a temporary 2D substrate, device fabrication on the 2D substrate, and structural transformation from 2D to 3D. In a nutshell, the FET was first made on a silicon-on-insulator wafer with standard cleanroom micro/nanofabrication techniques. Second, the completed FET was released from the silicon-on-insulator wafer and transfer-printed on a temporary 2D substrate. Third, a sequence of different functional materials was deposited on the FET to enable the electrical and mechanical robustness of the device. Finally, the fabricated multi-layered device was released and transfer-printed on a prestrained elastomeric substrate for controlled buckling. The detailed fabrication process will be described below in connection with FIG. 6.

Finite Element Analysis of the 3D FET

ABAQUS (v6.13) was used to study the mechanical behavior of the device during compressive buckling. As the thickness of the silicone substrate was much greater than that of the device, a boundary condition was to constrain the device to buckle only above the substrate. Displacement boundary conditions were applied to the two edges of the device to initiate the compression. Composite shell elements (S4R) were used to model the SU-8, PI, Si, and Au layers. The minimal size of the element was set to be half of the FET tip's width (~0.5 μm). The total number of elements in the model was ~106. Mesh convergence of the simulation was accomplished for all cases. The elastic modulus (E) and the Poisson's ratio (v) are as follows: EPI=2.5 GPa, vPI=0.34; ESi=130 GPa, vSi=0.27; EAu=78 GPa, vAu=0.44; and ESU-8=4 GPa, vSU-8=0.22. The fracture strain of Au and Si are 5% and 1%, respectively.

Surface Conductivity Mapping of the FET

The FET was characterized by a scanning microwave microscope (SMM; Keysight™ 7500), which combined an atomic force microscope and a vector network analyzer. The atomic force microscope had a conductive probe scanning on the FET surface to show the topography. Simultaneously, a microwave signal from the network analyzer was transmitted to the probe, reflected by the sample at the contact point, and then sent back to the network analyzer. The reflection coefficient obtained from the transmission and reflection signals showed the conductance information. Detailed calculations of the reflection coefficient will be presented below.

Phospholipid Coating

Phospholipid coating on the FET surface facilitated the cell internalization process, by spontaneous fusion, to achieve direct contact with the cells' cytosols. Briefly, large phospholipid vesicles in aqueous solutions were broken into small unilamellar vesicles by consecutive freeze-and-thaw treatments, sonication, and filter extrusion. These high-surface-energy vesicles would form uniform phospholipid coatings on the FET surface by self-assembly. Schematics in FIG. 18, discussed below, demonstrate the whole process in steps. Successful coating of the phospholipids was verified by the fluorescent images shown in FIG. 19, also discussed below.

Fabrication of the Multi-Electrode Array

The multi-electrode array, composed of Au electrodes, an SU-8 insulation layer, and a glass substrate, was fabricated using standard micro/nanofabrication techniques. The detailed fabrication process will be described below.

Water-Gate Characterization

The FET's sensitivity was obtained by measuring the FET's transfer characteristics. In the water-gate characterization (see FIG. 15), the corresponding FET's conductance was measured under a fixed positive bias (e.g., 200 mV) at the source and a potential sweep (from −100 to 100 mV) at the gate. Experimental details will be presented below.

$Ca^{2+}$ Sparks Screening

Schematics presented in FIG. 21, described below, illustrate the process of staining $Ca^{2+}$ and monitoring their transient activities under the fluorescent microscope. First, the HL-1 cells were cultured in a supplemented Claycomb medium. We removed the cell culture medium by aspiration and added clear-color typical Tyrode's solution. Second, we added the Fluo-4 AM (Invitrogen™) stock solution to the cells and incubated it for an hour to facilitate the loading of calcein dyes. Then, we removed the old solution and refilled it with fresh Tyrode's solution. Finally, we monitored the $Ca^{2+}$ signals under a microscope with a 480 nm excitation filter and a 525 nm emission filter.

HL-1 Cell Culture

We followed the standard cell culture protocol provided by Sigma-Aldrich. All materials and solutions were from Sigma-Aldrich. The cells were cultivated in the supplemented Claycomb medium after pre-coating the substrates with templating materials. We prepared the cell cultures on PDMS sheets for signal recording, on cell culture flasks for cell proliferation, and on cell culture dishes for $Ca^{2+}$ sparks screening. The details will be presented below.

Primary Cardiomyocytes Culture

Neonatal mouse ventricular myocytes were isolated from 1~2-day old Black Swiss mouse pups purchased from Charles Rivers Labs. Adult mouse single ventricular myocytes were isolated from the mouse ventricles using the enzymatic digestion method by Langendorff. The cells were obtained by digesting the ventricles in buffered solutions. After removing the fibroblast cells and blood from the vasculature, the cardiomyocytes were cultured on laminin templated PDMS sheets or cell culture dishes for signal recordings. The detailed preparation of the solutions will be presented below.

Whole-Cell Patch-Clamp Electrophysiology

Whole-cell current patching on HL-1 cells and primary cardiomyocytes were performed at 35° C. with cells plated on a PDMS sheet superfused with an external solution. A glass micropipette filled with the solution in the lumen was attached to the cell membrane, forming a giga-seal. After that, the membrane patch got ruptured by a negative pressure in the pipette, which established the whole-cell configuration. Action potentials were recorded with a holding potential at −80 to −40 mV and evoked by injecting currents to the cells.

Data Acquisition

An electrophysiological signal acquisition system includes the FETs for interfacing with the cells, preamplifiers, a signal digitizer, and a graphical user interface (i.e., computer software) for data visualization. We used a customized 10-channel preamplifier and a commercial data acquisition system (Axon) and software (Axon) with the 10-FET array, and a commercial 256-channel current-input analog-to-digital converter (Texas Instruments) and its configured software with the 128-FET array. Sampling rates adopted in these recordings ranged from 500 to 100,000 Hz in different systems. Before recording cellular signals, we characterized the complete signal measurement system (including a 10-FET array, the preamplifier, and the data acquisition device) and confirmed that the system had low intrinsic noise and no electrical crosstalk among these channels (see FIGS. 33 and 34).

Signal Processing

All signal recordings were post-processed offline in MATLAB (Math Works). Intracellular and extracellular signals of 2D cell cultures (HL-1 cells, adult mouse, and neonatal mouse cardiomyocytes) recorded by the FETs had large signal-to-noise ratios and thus raw data were presented. The MEA recordings of HL-1 cells passed through a notch filter (60 Hz) and a bandpass filter (0.5 Hz to 30 Hz). The electrical signals of the 3D cardiac muscle tissues, if without specified notes, were filtered through a bandpass filter (0.1 Hz to 30 Hz). The FET's sensitivity, noise level, and the delay between two action potential signals were also calculated in MATLAB and will be discussed below.

Electrical Stimulation of the HL-1 Cells

An electrode made of platinum was used to stimulate the HL-1 cells and manipulate their firing patterns. We applied a biphasic squared pulses stimulus (1 V, 1 Hz, and 1 ms peak width) by an analog output terminal in a commercial DAQ system (Digidata 1440, Axon) with a commercial software (pCLAMP 10.3, Axon). The electrode was placed ~10 mm away from FETs.

Pharmacological and Ion-Concentration Modulation of HL-1 Cells' Electrophysiology We added nifedipine (Sigma Aldrich or Abcam) or TTX (Sigma Aldrich or Abcam) into the typical Tyrode's solution. We tuned the potassium or sodium concentrations in the typical Tyrode's solution. These solutions were administered by perfusing (i.e., simultaneous aspirating the old solution and adding the new solution) the cells when the cells' electrical signals were simultaneously recorded.

Engineering of Cardiac Microtissues

Neonatal rat cardiomyocyte tissues were engineered on a PDMS platform composed of a well and two microposts using the methods previous reported (see FIG. 45). Cardiomyocytes were mixed with the collagen-based gel at a density of ~50 M cells·ml−1. Each cell-laden hydrogel was filled inside the PDMS well around two micro-posts and incubated for 1 hour. Then, culture media was added to the cell-laden gels, followed by incubation. Additional details will be presented below.

Fluorescence Staining of Live Cells

The HL-1 cell membranes were marked by a cytoplasmic membrane dye (CellBrite-Red). Cell nuclei were stained with NucBlue. The polyimide layer in the FETs was mixed with rhodamine 6G dye. Additional details will be presented below.

Quantification and Statistical Analysis

Signal latencies in FIG. 4 were calculated by cross-correlating each two recording traces in MATLAB. The signal conduction velocity was calculated by linear regression of the extracted signal latencies from the raw data. Data in FIGS. 2, 3, 4, and 5 were processed and visualized using MATLAB.

Conclusions

With the device size down to the submicron regime, the high sensitivity, and the high signal-to-noise ratio, FETs have attracted growing attention as a tool for interrogating electrogenic cells in the past decade. 2D planar FETs for extracellular interfacing usually lack one-to-one correspondence between the cells and FETs, providing information on an ensemble of cells near the FET. 3D FETs allow direct interfacing with the cytoplasm of cells, which ensures the correspondence to each specific recorded cell. However, existing 3D FET devices are not for large-scale, high-spatial-resolution sensing. With an unprecedented number and a pre-defined layout, the 3D FET sensor array in this work can fill this technological gap (see FIG. 46). The arrayed FETs provide tremendous opportunities for studying fundamental physiologies of electrogenic cells. The acquired knowledge can help understand the pathology and guide the treatment of numerous evolutionary disease models.

The intracellular signals disclose more meaningful information about the cell type and density of various ion channels. Particularly, the full-amplitude action potentials are highly relevant to the disease status and pathology of the cells. Sub-threshold signals can potentially shed light on the process of intercellular synchronization, the mechanism of electrophysiological modulation, and how these sub-threshold signals impact the development of sensory systems. The studies of the conduction behavior would not only enhance the understanding of the ionic transport across organellular membranes within a cell but also facilitate the studies of electrical coupling between different cells. These findings carry significant implications for understanding subcellular electrophysiology, organellar ionic dynamics, organelle-cell membrane interaction, and their influences on cellular physiological activities, including proliferation, differentiation, and apoptosis.

The 3D FET sensor array described herein can be applied to various types of cardiac tissues, such as embryonic stem cell-derived cardiomyocytes, myocyte-fibroblast cocultures, and other general electrogenic cells, such as neurons. Reliable recordings of 3D tissues on a large scale may reveal the cellular alignment directions. In vivo studies may be performed by ensuring that the 3D FET sensor array can penetrate through the thick membranes on the myocardium and the cortex, preventing severe immune responses, and eliminating motion artifacts induced by heart beating and brain pulsation. To accomplish this the 3D FETs' structures (e.g., tip size, spacing, and relative positions), array size, structural materials, surface coating, and deployment approach may be chosen to enhance the reliability, quality, and duration of the recordings. Additionally, artificial intelligence assisted signal processing may be used.

Fabrication of the 3D Field-Effect Transistor (FET)

Figure 6A:
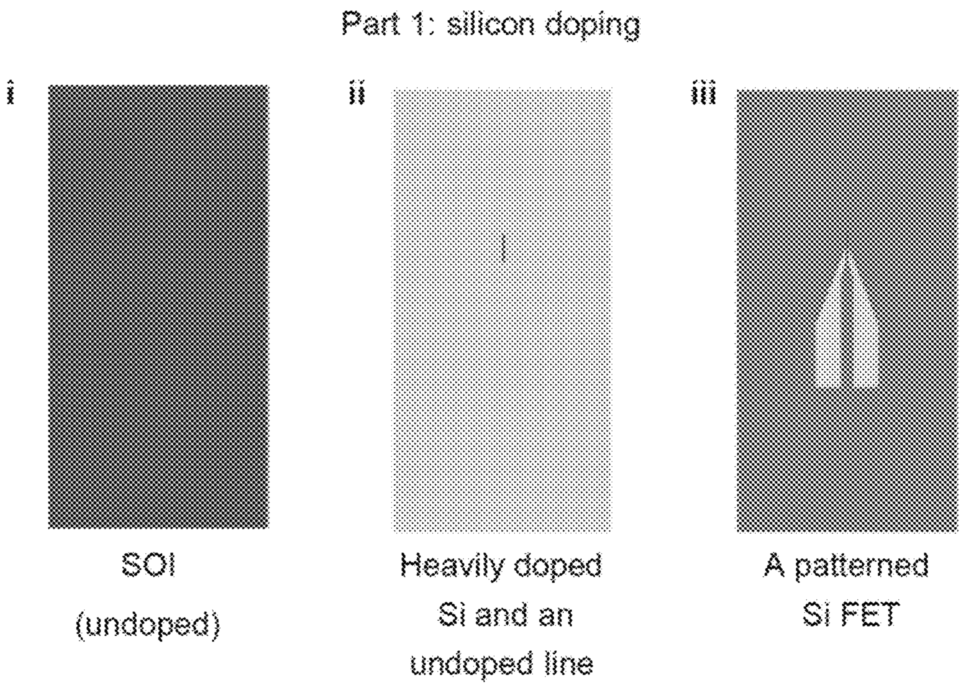
FIGS. 6A-6C show a series of schematically illustrated steps showing the fabrication steps of one example of the 3D FET sensor array.
Figure 6B:
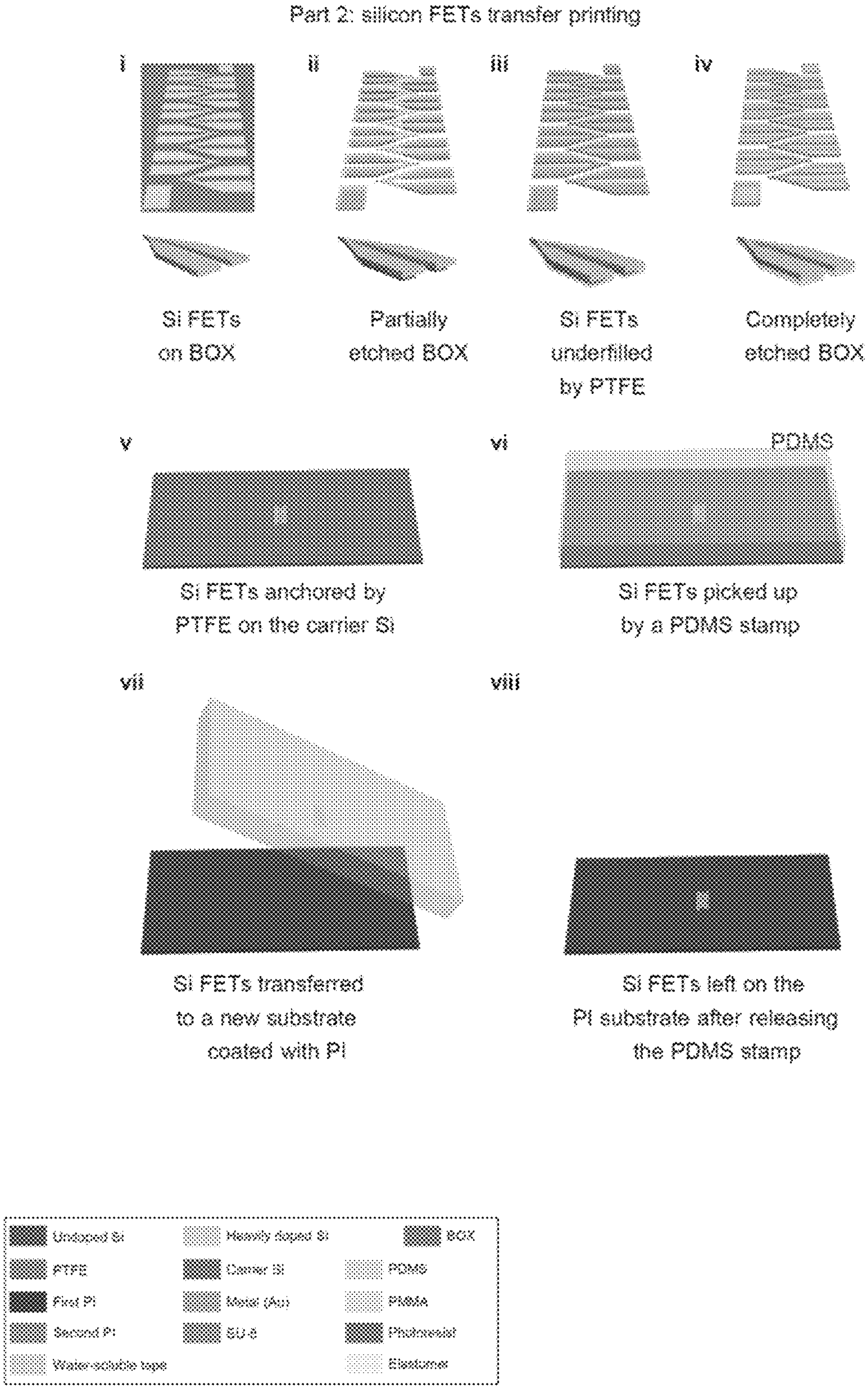
Figure 6C:
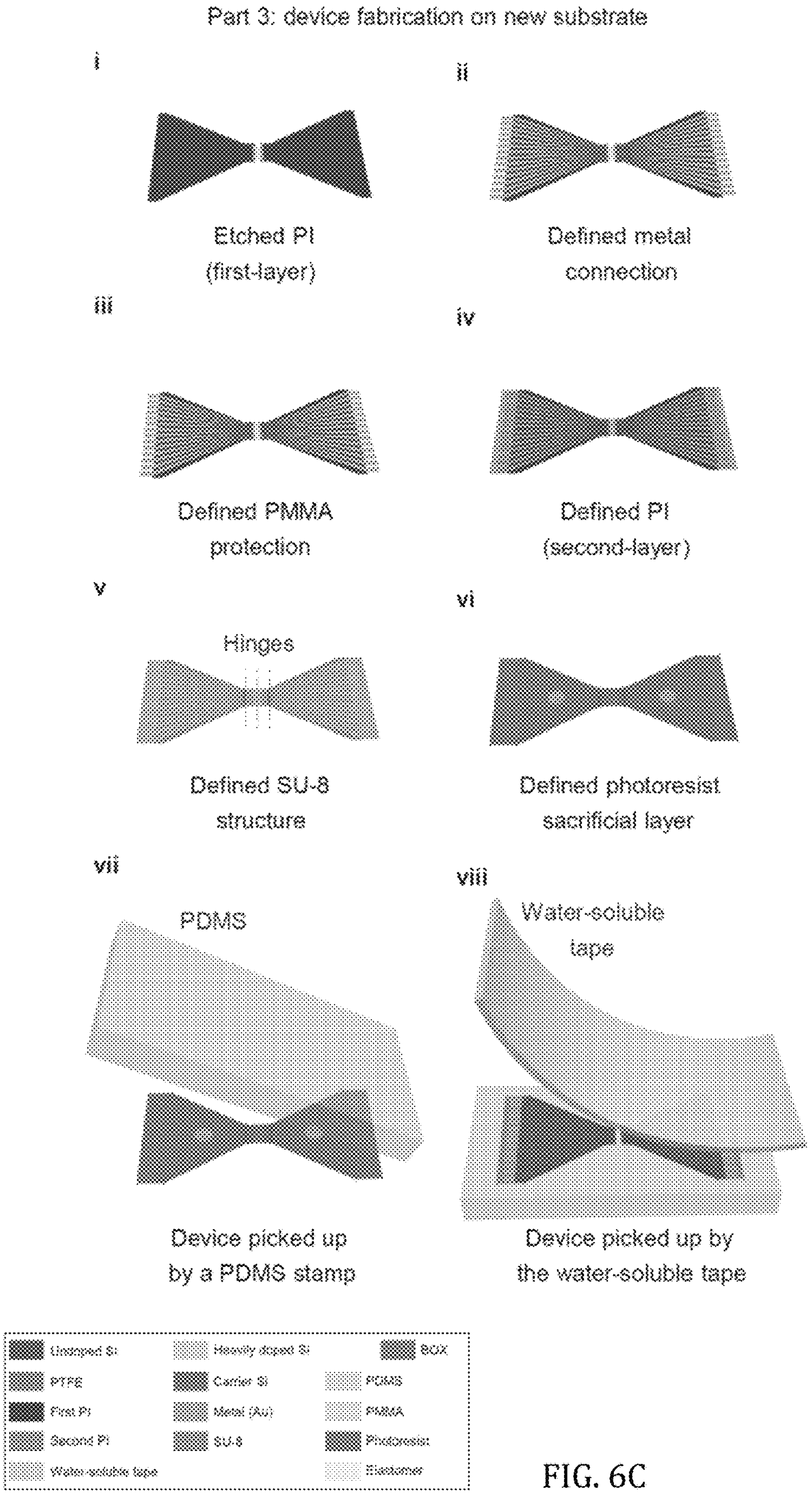
Figure 12A:
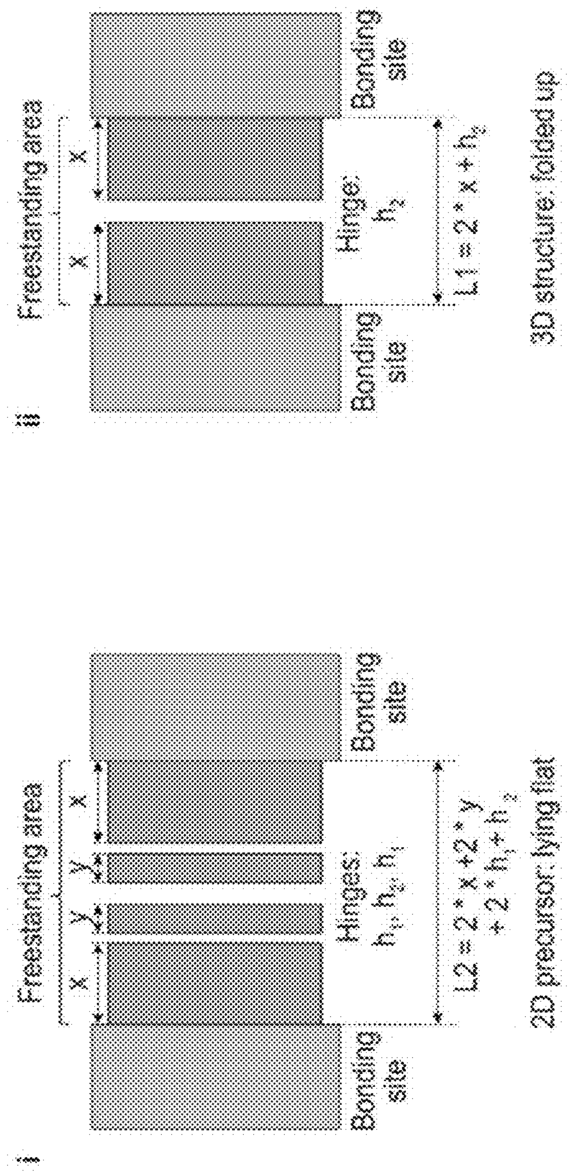
FIGS. 12A-12B show the structural design of one example of the 3D FET sensor arrays described herein.
Figure 12B:
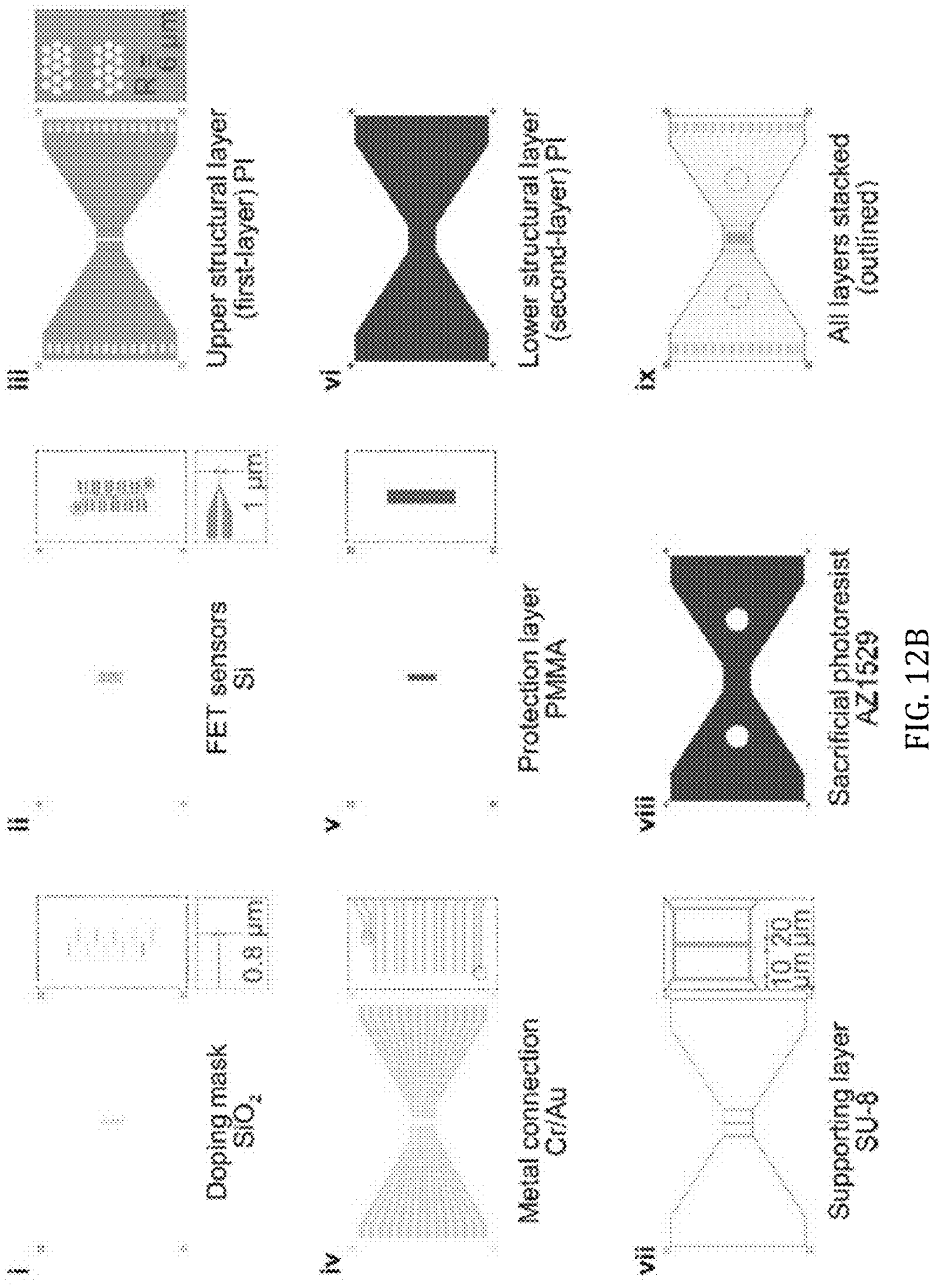
Figure 13A:
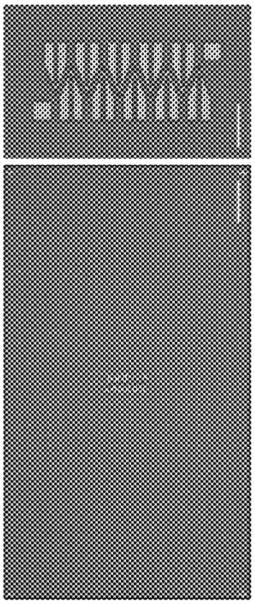
FIGS. 13A-13H show optical microscopical images illustrating the fabrication steps of the arrayed FETs.
Figure 13B:
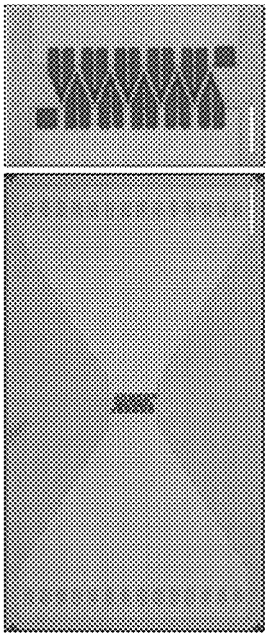
Figure 13C:
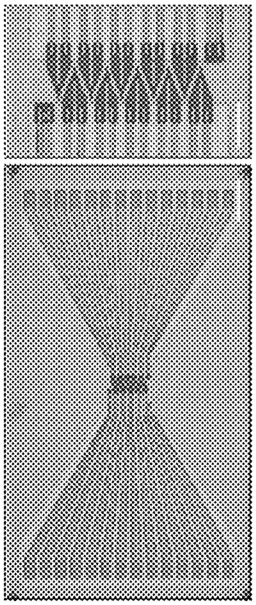
Figure 13D:
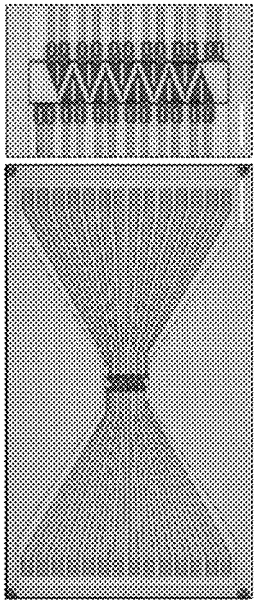
Figure 13E:
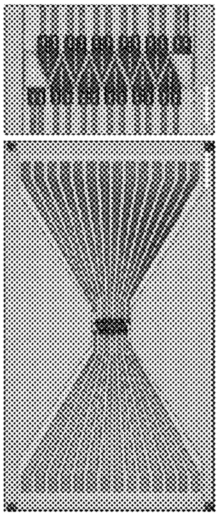
Figure 13F:
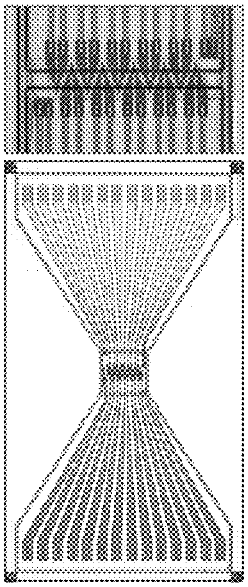
Figure 13G:
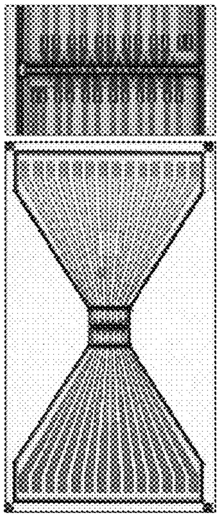
Figure 13H:
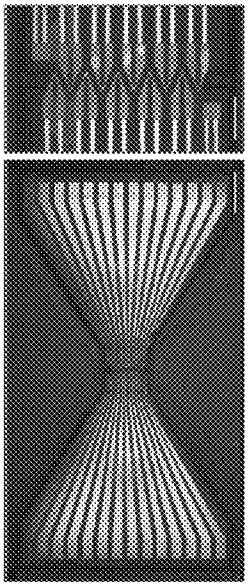

In some implementations, fabrication some examples of the stretchable 3D FET array involved standard micro/nanofabrication techniques, as well as a specially tailored transfer printing technique, and the compressive buckling technique. Details are illustrated in FIG. 6*a* and FIG. 12 and will be described below for one particular embodiment.

The 3D FET has a functional silicon transistor connected with gold conduction electrodes, which are sandwiched by two polyimide (PI) structure layers. A poly(methyl methacrylate) (PMMA) layer is holding and protecting the FETs during the sequential fabrication process. It would get removed by acetone before releasing the prestrain and applying the compressive force. A relatively rigid SU-8 layer serves as the mechanical support of the whole device. A photoresist layer defines the bonding sites of the SU-8 to the prestrained elastomeric substrate.

1.1. Si Doping Defining the FET's Drain, Source, and Gate Terminals (See FIG. 6*a*)

1.1.1. Preparation of the Silicon Substrate

The device was fabricated on a silicon-on-insulation (SOI) wafer (University wafers, device layer: 1.5 μm, oxide layer: 3 μm, carrier layer: 550 μm). SOI samples were diced by a diamond dicing machine and cleaned thoroughly in an RCA (Radio Corporation of America) clean process to remove all organic contaminations, particles, and $SiO_2$ on the wafer surface (Mixture solution is Ammonia hydroxide (29%): hydrogen peroxide (30%): deionized (DI) water=1:1:5 in volume; The solution was heated to 140° C., and the samples were boiled for 15 min; The oxide on the silicon surface got removed by dipping the samples in buffered oxide etchant (BOE) 6:1 for 2-3 seconds followed by DI water rinsing). Next, the 1.5 μm silicon was thinned down to 400 nm by dry etching (inductively coupled plasma-reactive ion etching (ICP-RIE)); RIE: 30 W, ICP: 1,200 W, 18.0 mTorr, 20° C., 25.0 sccm $SF_6$, 50.0 sccm $C_4F_8$, 120-180 s). Another dry etching process (ICP-RIE; RIE: 200 W, ICP: 2,000 W, 50.0 mTorr, 15° C., 50 sccm $O_2$, 1 min) removed the induced $C_4F_8$ residue coated on the silicon surface.

1.1.2. $SiO_2$ Doping Mask Fabrication

The sample was RCA cleaned again to remove any oxide or contaminants on the surface. Alignment markers at the four corners of the sample were defined by photolithography (photoresist NR-3000PY: spin-casting at 4,000 r.p.m. for 60 s, baking on a hotplate at 150° C. for 60 s, UV irradiance at 220 $mJ \cdot cm^{-2}$, post-exposure baking at 100° C. for 60 s, and developing for ~20 s with developer RD6) and dry etching (ICP-RIE: 30 W, ICP: 1,200 W, 18.0 mTorr, 20° C., 25.0 sccm $SF_6$, 50.0 sccm $C_4F_8$, 60 s). The silicon on the alignment markers positions was thinner than the other areas, providing optical contrast while aligning the photomask in subsequent fabrication steps. Next, $SiO_2$ doping mask was fabricated by depositing a uniform 100 nm or 300 nm thick oxide layer on the sample surface using plasma-enhanced chemical vapor deposition (PECVD; RF power: 20 W, 1,000 mTorr, 350° C., 117.0 sccm $SiH_4$, 710.0 sccm $N_2O$, 246 s), and the doping mask patterns were defined by photolithography (photoresist AZ 1505: spin-casting at 4,000 r.p.m. for 45 s, baking on a hotplate at 105° C. for 90 s, UV irradiance at 30 $mJ \cdot cm^{-2}$, and developing for ~15 s with developer AZ 300 MIF) and dry etching $SiO_2$ (RIE: 150 W, 30.0 mTorr, 20° C., 25.0 sccm Ar, 25.0 sccm $CHF_3$, 720 s).

1.1.3. Thermally Driving Dopants into the Silicon

Figure 8B:
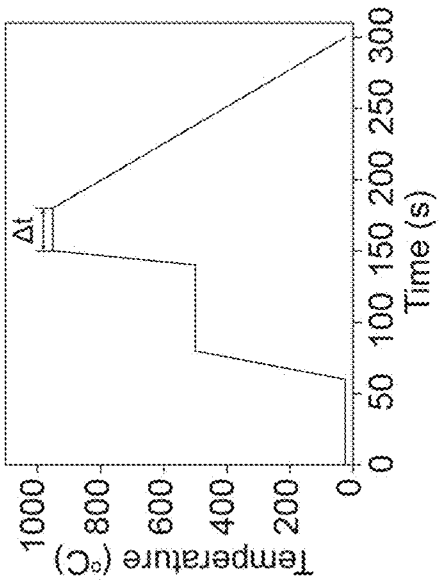
FIG. 8A-8F show data for optimizing the FETs' electrical properties by tuning doping concentrations.
Figure 8A:
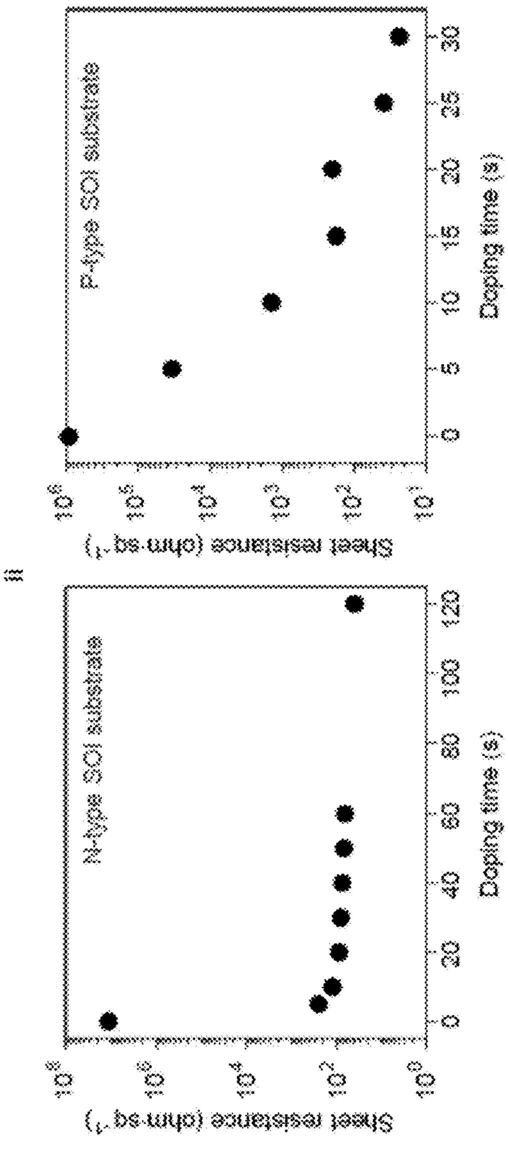
Figure 8C:
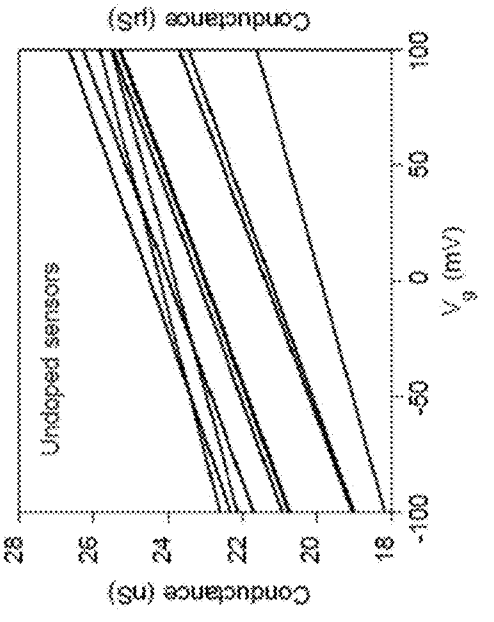
Figure 8D:
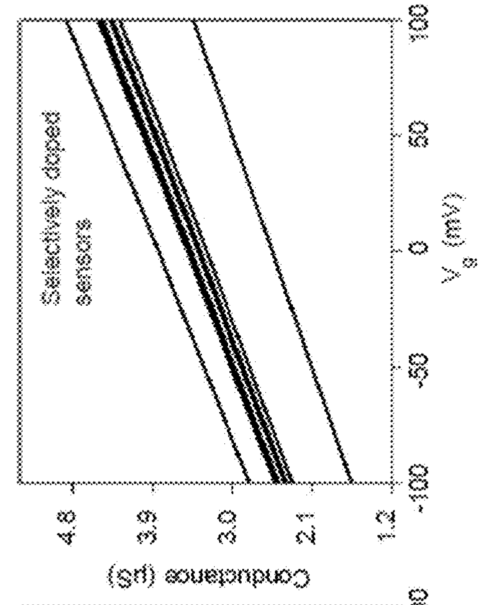
Figure 8E:
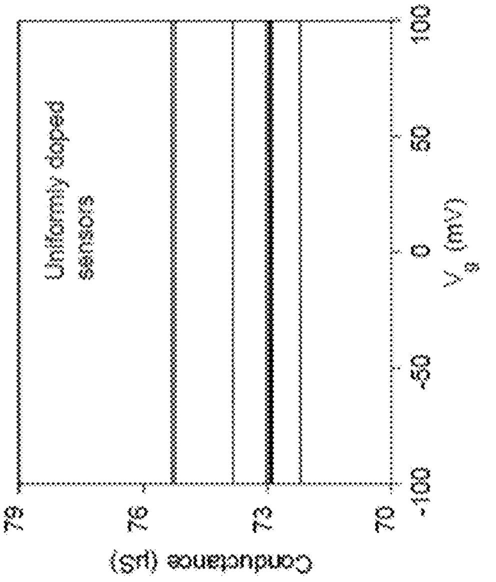

The dopants were coated on the sample surface (spin-on diffusants, B151 or P509: spin-casting at 3,000 r.p.m. for 10 s, soft baking on a hotplate at 200° C. for 15 min) and annealed in a rapid thermal annealing furnace (RTA furnace: 950° C. for certain time referring to FIG. 8*b*). During sample annealing, the dopants would diffuse into the silicon dioxide mask instead of the underneath silicon, forming the selectively undoped regions. Then, the doping mask and the excessive dopants got removed in BOE for ~15 min. After that, silicon probe structures were defined by photolithography (photoresist AZ 1505: spin-casting at 4,000 r.p.m. for 45 s, baking on a hotplate at 105° C. for 90 s, UV irradiance at 30 $mJ \cdot cm^{-2}$, and developing for ~15 s with developer AZ 300 MIF) and silicon dry etching (RIE: 30 W, ICP: 1,200 W, 18.0 mTorr, 20° C., 25.0 sccm $SF_6$, 50.0 sccm $C_4F_8$, 60 s) and a follow-up RCA clean to obtain contamination-free silicon samples for FETs. It was notable that offsets in doping regions caused by misalignment of photolithography and/or non-uniform doping induced by uneven spin-coating on the silicon surfaces would introduce variations in the measured conductance and transconductance of the FETs.

1.1.4. Characterization of the Doping Results

The FET had a lightly doped conduction channel in the middle and two heavily doped source and drain terminals on the sides. We characterized the doping concentration distribution by using an atomic force microscope coupled with the scanning microwave microscopy function, as described in the Methods section in the main text. The topography image in FIG. 1*d* reflects the height profile of the FET surface. The height difference between the lightly doped middle region and its two sides was due to the RIE etching of the $SiO_2$ when defining the doping mask that covered the middle part. To dry etch the $SiO_2$, $CHF_3$ gas was applied, which could also react with Si at a selectivity of 3:1. If there was any over-etching, the exposed Si would also be etched to form a small step edge compared to the middle region protected by photoresist during the dry etching. Over-etching was preferred over under-etching because we wanted to ensure the silicon is completely exposed before casting spin-on-dopants to fulfill successful doping.

1.2. Transfer-Printing of the FET Sensors to a New Substrate (see FIG. 6*b*)

1.2.1. Free the FET Device Structure from the Oxide Layer Underneath

The 3 μm oxide layer (buried oxide: BOX) in the SOI was wet etched (hydrofluoric acid (HF) 49%: 140-160 s) to undercut the FET structures, and also left sufficient oxide residue to connect the FET structures to the carrier wafer. A layer of PTFE (polytetrafluoroethylene) (AF: PTFE (Amorphous Fluoroplastics Solution) was deposited: spin-casting at 1,000 r.p.m. for 60 s, baking on a hotplate sequentially at 110° C. for 5-10 min, 245° C. for 5 min, and 330° C. for 15 min) on the FET surfaces, and dry etched (RIE; 80 W, 50.0 mTorr, 35-40° C., 50.0 sccm $O_2$, 10 s) to expose the silicon surface. As a result, the previous undercut portion of $SiO_2$ was filled with PTFE. Then, the rest of the $SiO_2$ was completely etched off by placing the samples in HF (49%) for 2-3 hours.

1.2.2. Preparation of a Temporary 2D Substrate for the FET Structures

A temporary 2D substrate was needed to connect and encapsulate these FET structures in functional devices. The temporary substrate was prepared by sequentially coating Al (sputtering; 200 W, 3.0 mTorr, 10 sccm Ar, 5 min, ~60 nm), PMMA (495 All: spin-casting at 4,000 r.p.m. for 60 s, baking on a hotplate at 180° C. for 1 min, ~800 nm), and $SiO_2$ (plasma enhanced chemical vapor deposition (PECVD); RF power: 20 W, 1,000 mTorr, 350° C., 117.0 sccm $SiH_4$, 710.0 sccm $N_2O$, 82 s, ~100 nm). Here, the Al layer served as the sacrificial materials to be later etched away in hydrochloric acid (HCl, 37-38%) to release the FET device from the substrate. The PMMA and $SiO_2$ dual layers acted as the protection materials to firstly avoid HCl from attacking the metal connections at the Au/Cr/Si interfaces, and to secondly prevent chemicals in subsequent steps from overetching the PI or PMMA.

1.2.3. Transfer-Printing of the FET Structures

The sample prepared in 1.2.1 was deposited with an anti-adhesive $C_4F_8$ layer (RIE: 5 W, ICP: 500 W, 18.0 mTorr, 20° C., 10.0 sccm $C_4F_8$, 120 s) to reduce the adhesion between the silicon device and the transfer-printing stamp. A polydimethylsiloxane (PDMS; base: curing agent=4:1 in weight ratio) stamp was used to press on the FET structures and quickly pick them up from the SOI carrier wafer. Dry etching (RIE: 80 W, 50.0 mTorr, 20° C., 50.0 sccm $O_2$, 420 s) the picked-up silicon surface to completely remove all of the PTFE underneath the FETs and to activate the silicon surface. Next, PI (2545; spin-casting at 6,000 r.p.m. for 60 s, baking on a hotplate at 100° C. for 20 s, ~1.6 μm) was coated on the prepared temporary substrate as described in 1.2.2. At the time the PI layer was baked for 20 s, we pressed the PDMS stamp with the activated FET surface contacting the PI and held on the hotplate for 1 min before slowly releasing the PDMS stamp from the substrate. Then the FET structures were successfully transfer-printed to the temporary substrate.

1.3. Fabrication of the 2D Arrayed FETs (see FIG. 6*c*)

1.3.1. Determination of the FET Shape

The $C_4F_8$ layer left on FET surfaces got removed by dry etching (RIE: 80 W, 50.0 mTorr, 35-40° C., 50.0 sccm $O_2$, 10 s). Then we fully cured the PI layer (hard baking on a hotplate; 250° C., 60 min). Its shape was determined by photolithography (photoresist AZ 1529: spin-casting at 4,000 r.p.m. for 45 s, baking on a hotplate at 95° C. for 120 s, UV irradiance at 350 mJ·cm$^{-2}$, and developing for ~40 s with developer AZ 300 MIF) and dry etching (RIE: 80 W, 50.0 mTorr, 35-40° C., 40.0 sccm $O_2$, 10 sccm $CF_4$, 300 s).

1.3.2. Metallization for Interconnections

A lift-off process was used to define the metal patterns for connecting the FETs by photolithography (photoresist NR-3000PY: spin-casting at 4,000 r.p.m. for 60 s, baking on a hotplate at 150° C. for 60 s, UV irradiance at 220 mJ·cm$^{-2}$, post-exposure baking at 100° C. for 60 s, and developing for ~20 s with developer RD6) and sputtering (chromium: 200 W, 3.0 mTorr, 5 sccm Ar, 30 s, ~5 nm; gold: 200 W, 3.0 mTorr, 5 sccm Ar, 5 min, ~100 nm). The metallization was finalized after the samples were soaked in acetone for 15 min. Moisture induced in the lift-off process got removed when the samples were baked in a vacuum oven at 100° C. for 10 min.

1.3.3. Embedding a Sacrificial Layer for Holding the FET Sensors

A PMMA layer was coated on the FETs for dual purposes: to protect the FETs during the following fabrication process and to serve as a sacrificial layer to release the FETs from the PI layer during the compressive buckling. Because PMMA is not photo-patternable by UV light in photolithography, a combination of photolithography and dry etching process was employed to pattern the PMMA layer. Given that PMMA is dissolvable in organic solvents such as acetone and NMP that would be used to remove the photoresist after dry etching, we coated a thin layer of PI on the PMMA before casting the photoresist. Notably, the PI is also photo-patternable and dissolvable in basic developers such as AZ 300 MIF but is resistant to acetone. Herein, sequential coating of PMMA (495 A11: spin-casting at 2,000 r.p.m. for 60 s, baking on a hotplate at 180° C. for 1 min, ~1,250 nm) and PI (PI2545/NMP=2:1 in volume; spin-casting at 3,000 r.p.m. for 60 s, baking on a hotplate at 150° C. for 1 min, ~624 nm) followed by photolithography (photoresist AZ 1512: spin-casting at 4,000 r.p.m. for 60 s, baking on a hotplate at 95° C. for 60 s, UV irradiance at 120 mJ·cm$^{-2}$, and developing for ~12 s with developer AZ 300 MIF) and dry etching (RIE: 80 W, 50.0 mTorr, 35-40° C. 50.0 sccm $O_2$, 150 s) defined the PMMA structure. The photoresist and PI on top of the PMMA got removed by acetone and developer AZ 300 MIF, respectively. Similarly, moisture was removed in the vacuum oven (100° C., 5 min).

1.3.4. Sandwiching the Functional Materials by a Second PI Layer

An adhesion promoter for PI (VM651/DI water=1:50 in volume; spin-casting at 3,000 r.p.m. for 60 s, baking on a hotplate at 100° C. for 1 min) was cast before a second PI layer (PI2545; spin-casting at 1,500 r.p.m. for 60 s, baking on a hotplate at 150° C. for 1 min, ~4,500 nm) was formed to sandwich the FET sensors and the PMMA. Its pattern was established by photolithography (photoresist AZ 1529: spin-casting at 4,000 r.p.m. for 45 s, baking on a hotplate at 95° C. for 120 s, UV irradiance at 350 mJ·cm$^{-2}$, and developing for ~40 s with developer AZ 300 MIF) and dry etching (RIE: 80 W, 50.0 mTorr, 35-40° C., 50.0 sccm $O_2$, 300 s). The PI was fully cured after baking at 250° C. on a hotplate for 1 hour.

1.3.5. Forming a Mechanical Support of the Soft Structure

A relatively rigid and thick SU-8 layer provided structural support to the device. The second PI layer was activated by oxygen plasma (RIE: 50 W, 50.0 mTorr, 35-40° C., 50.0 sccm $O_2$, 10 s) to bond with the SU-8 and prevent any delamination that might occur in the multi-layered device. Photolithography (SU-8 2010: spin-casting at 4,000 r.p.m. for 30 s, baking on a hotplate at 95° C. for 150 s, UV irradiance at 140 mJ·cm$^{-2}$, post-exposure baking at 95° C. for 210 s, and developing for ~140 s with SU-8 developer). Hard baking (100° C. on a hotplate, 1 hour) fully crosslinked the polymer chains of the SU-8.

1.3.6. Adding a Sacrificial Layer to the Compressive Buckling Process

A photoresist layer served as the sacrificial material for releasing the non-bonded areas of the device during the compressive buckling. To fabricate such a layer, the SU-8 surface was activated (RIE: 50 W, 50.0 mTorr, 35-40° C., 50.0 sccm $O_2$, 30 s) before coating a photoresist layer followed by photolithography (photoresist AZ 1529: spin-casting at 4,000 r.p.m. for 45 s, baking on a hotplate at 95° C. for 120 s, UV irradiance at 350 mJ·cm$^{-2}$, and developing for ~40 s with developer AZ 300 MIF).

1.4.1. Releasing the Flexible Device by Removing the Sacrificial Metal Layer

The device had a stack of layers and was attached to the temporary substrate during the fabrication processes as described above. To free the multi-layered device from the temporary substrate, the Al layer was etched in HCl fume evaporated from HCl solution (37-38%). After 12-hour etching, the Al was mostly gone, but device was still loosely anchored on the substrate by the photoresist pattern and could be released from the substrate by the mechanical force of the stamp.

1.4.2. Transfer-Printing the Device to a Prestrained Elastomer Substrate

A PDMS stamp picked up the device from the substrate. A cellulose-based, water-soluble tape allowed retrieval of the device from the PDMS stamp. Next, a strip of elastomer (Dragon Skin) was placed and prestrained on a uniaxial stretcher. The device and the dragon skin surfaces were treated in ultraviolet-induced ozone (UVO) cleaner, with the UV lamp ~1 cm apart from their surfaces, for 10 minutes. The device/tape was transferred on the UVO-treated elastomer surface with press. The bonded structure was then baked in a convection oven at 80° C. for 10 min.

1.4.3. Popping up the Device by Releasing the Prestrain

DI water and acetone removed the water-soluble tape and the PMMA and photoresist layers in the device, respectively. The selectively bonded sites were located at middle places of the SU-8. When the prestrain in the elastomer substrate was slowly released, the 2D structure transformed to the 3D configuration gradually. Finally, the entire device was rinsed with BOE and DI water to remove any oxide residues adhered to the device.

1.5. Wiring the Device and Sterilization before Interfacing with Cells

Before interfacing with cells, first, the entire device was wired using anisotropic conductive film (ACF) cables, which were bonded to the backend flat printed circuit cable (FPC) connector board (by aligning and pressing the cable on the tin leads with heating at 180° C. for 10 s). Second, the device was coated by a bilayer of Parylene C (1 g) and $SiO_2$ (sputtering; 200 W, 3.0 mTorr, 50 sccm Ar, 10 min). Parylene C was used to protect the silicon FET from dissolving in the solution. $SiO_2$ was used to generate a hydrophilic surface of the FET for binding with phospholipids. The insulation layer was vital to maintain the FET's high sensitivity and material stability during the measurement. The device was soaked in 70% ethanol for half an hour and then treated by UV for 1 hour for sterilization.

Signal Analysis in Scanning Microwave Microscopy

The reflection coefficient of the microwave signal varies depending on the dielectric properties of the sample at each scanned point; hence the conductivity can be mapped. In the experiment, we particularly tuned the reference setting so we could verify if the corresponsive relationship between the reflection coefficient and the uncalibrated conductivity was positive or negative.

To enhance the measurement sensitivity, a homemade interferometric system was developed. The interferometric system contained a hybrid coupler that split the source microwave into two coherent signals. One signal went to the probe, and the other to a tunable attenuator and phase-shifter. Both signals got reflected: the former one was reflected by the sample, and the latter reflected by the tunable attenuator and phase-shifter. The two reflected signals were combined at the output of the coupler and canceled each other after proper tuning. The resulting signal was amplified and measured by the network analyzer in the transmission mode. With proper tuning, the system operated at its best sensitivity; small conductivity changes could be detected.

Figure 7B:
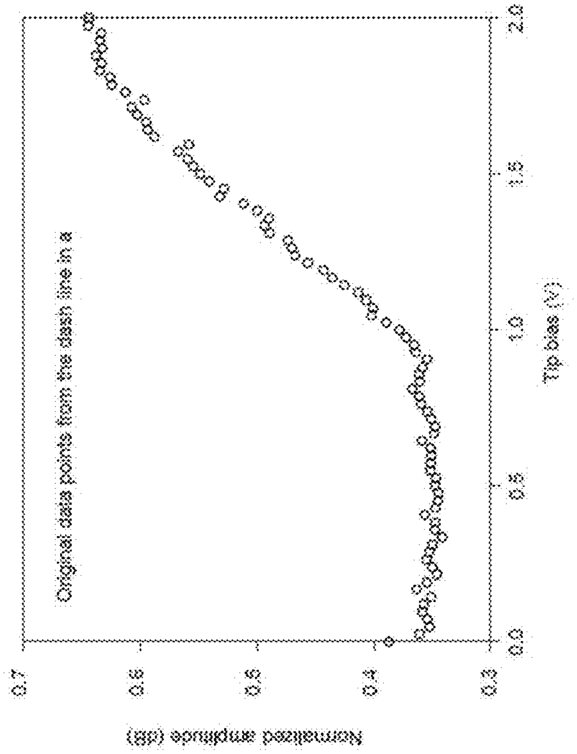
FIGS. 7A-7B maps the FET's conductivity by an atomic force microscope with a bias applied by the scanning tip.
Figure 7A:
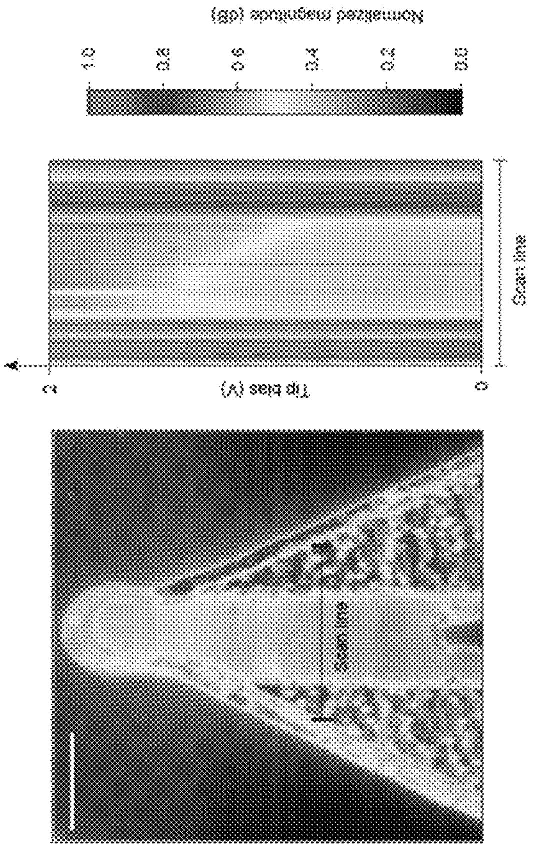

A linear scan of the FET tip area was performed to verify the doping results. In FIG. 7, the conduction channel's conductivity increased with a greater bias applied by the atomic force probe, which showed convincing evidence that the FET had an n-type channel. The conductivity went up when the tip bias was ~1 V, representing the threshold voltage to turn "ON" the FET. Notably, the FET was engineered to have an $N^+NN^+$ structure which meant it was in a depletion-mode at the "ON" state with zero gate bias, as shown in the water-gate characterizations in FIG. 2. The plausible contradiction here could be due to the different mechanisms of the characterization approaches, where the gate capacitance, method of applying the gate bias, and the information that could be read from the signals were different, which have been well studied. The difference of the ON/OFF voltage range between the tip-gate and the ion water-gate is mainly caused by that the ion water-gate has a much bigger gate capacitance (double-layer capacitance), so that a small gate-voltage can result in a larger carrier density change in the semiconductor channel, hence affect its conductance greatly. The tip gate capacitance is small; hence it needs a bigger voltage to reach the same switch effect.

Calculation of the Membrane Potential Recorded by the FET

Each FET's gate terminal was electrically coupled with the ionic solution, so ionic flows in the solution would change the electrical field and thus conductance in the conduction channel of the FET by electrostatic interactions. An FET sensed the electric field potential on its gate terminal and translated the value by its current readout through its conduction channel. The translational factor is defined by the transconductance of the FET, which we also used to define an FET's sensitivity. The transconductance $g_m$ is defined as:

$$g_m = \frac{\Delta I_{ds}}{\Delta V_g}, \tag{1}$$

where $I_{ds}$ is the current in the conduction channel of the FET and $V_g$ is the electric field potential on the gate, which also represents the membrane potential in recording the cellular signals. After measuring the transconductance of the FET, we can correspond the current in the conduction channel to the gate potential by the following formula:

$$I_{ds} = V_g \times g_m, \tag{2}$$

In the case of cell membrane potentials, it can be written as:

$$I_{ds} = V_m \times g_m, \tag{3}$$

where $V_m$ is the membrane potential, i.e., the action potential. The FET sensor was cascaded to a current preamplifier where the current was amplified and converted into a voltage reading and fed into the downstream data acquisition (DAQ)

system. The DAQ then digitalized the voltage signal as the computer readout, which could be expressed as:

$$V_r = I_{ds} \times \beta, \tag{4}$$

where $V_r$ is the voltage readout in the DAQ and β is the amplification of the preamplifier. We can establish the relationship between the membrane potential, $V_m$, and the voltage readout, $V_r$, by substituting equation (3) into equation (4):

$$V_r = V_m \times g_m \times \beta, \tag{5}$$

Or $$V_m = \frac{V_r}{g_m \times \beta}, \tag{6}$$

The amplification β is a known value, which was pre-set at its design period. The transconductance, $g_m$, can be determined by the slope of the line plot of $I_{ds}$-$V_g$ in the water-gate characterization of the FET sensor, seen in FIGS. 2*c* and *d*. Therefore, we can accurately obtain the recorded intra- or extra-cellular membrane potentials by the voltage readouts.

Justification of Using the n-Type Depletion-Mode FET ($N^+NN^+$) and Optimization of the Sensitivity-to-Noise Ratio The significant difference between a depletion-mode and an enhancement-mode FET is whether it is "ON" at zero gate bias, where the depletion-mode FET already has charges in the conduction channel ("ON") without a gate bias. The feature is beneficial for the FET biosensors to operate in an aqueous environment because we can avoid the large gate bias required to turn on the FET, which would generate irreversible faradaic reactions such as electrolysis of water. Further, the depletion-mode FETs show high sensitivity and thus have been extensively used to detect weak signals in biological systems.

Figure 8F:
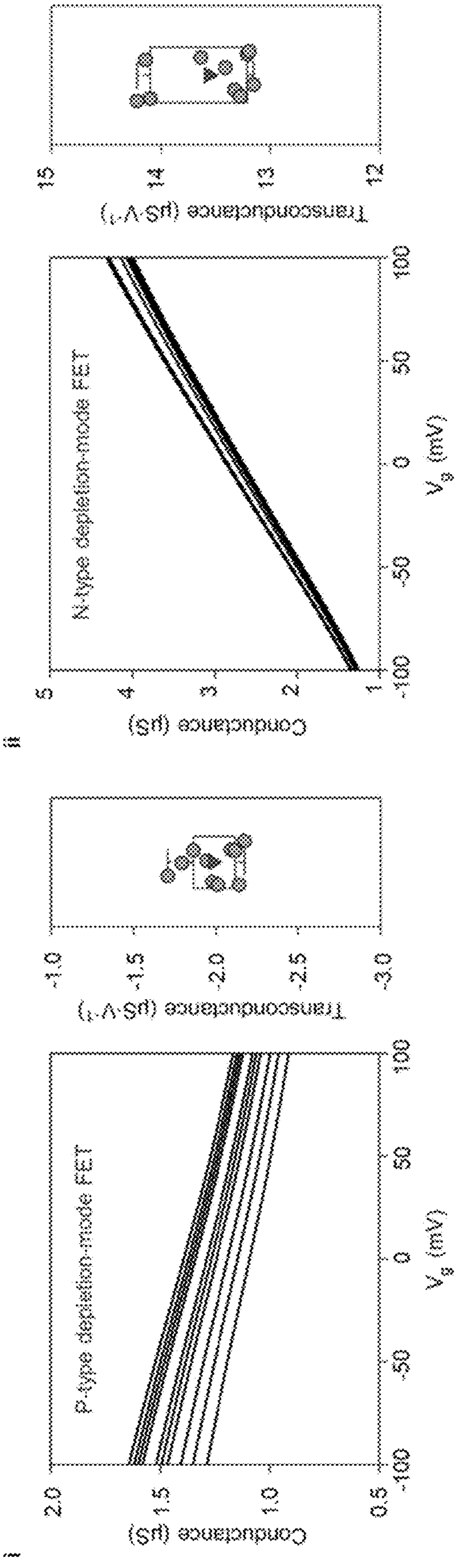

We prepared a p-type and an n-type depletion-mode FET arrays. These two arrays had the same structure and dimensions. Each array had ten FETs with heavily doped source and drain regions (p-type: ~10 ohm·sq$^{-1}$; n-type: ~10$^2$ ohm·sq$^{-1}$) and an undoped gate region (p-type: ~10$^6$ ohm·sq$^{-1}$; n-type: ~10$^7$ ohm·sq$^{-1}$). In FIG. 8*f*, transfer characteristics of both devices showed that the n-type FETs demonstrated about six times larger sensitivity than the p-type FETs. Therefore, we chose the n-type depletion-mode FET in this work.

Optimizing the doping levels in the drain, source, and gate regions of the $N^+NN^+$ FET yielded the largest sensitivity-to-noise ratio of the FETs. In this process, we lightly doped the gate region for 1~20 seconds (FIG. 2*a*). Before doping, the SOI wafer had a background doping level (antimony doped), making its sheet resistance ~10$^7$ ohm·sq$^{-1}$. The sheet resistances of lightly and heavily doped silicon were 10$^4$ ohm·sq$^{-1}$ and 10$^2$ ohm·sq$^{-1}$, respectively.

To improve the sensitivity-to-noise ratio, ideally, we want to increase the sensitivity and, in the meantime, decrease the noise level of the FET. However, these two properties would show a positive relationship between each other. In electrophysiological experiments, electrical measurement noises can arise from current fluctuations in the cell membrane, the sensors, the preamplifier electronics, and/or external sources such as power lines, computers, monitors, and many other devices located in the vicinity of the measurement setup.

External noises can be largely reduced by the application of electromagnetic shielding, such as using a faradaic cage to isolate the cells and sensors from the surrounding electronics. However, internal noises represented by current or voltage signal fluctuations cannot be avoided. These noises often show in low-frequency regions, so called low-frequency noise. Generally, thermal noise, shot noise, pink noise (i.e., flicker noise or 1/f noise), and generation-recombination noise represent the common internal noises in a transistor sensor. Pink noise and generation-recombination noises are frequency-dependent and are high in the low frequency.

The positive relationship between the noise level and the FET's sensitivity is in two aspects. First, there was external noise during the electrical measurement even a faradaic cage was implemented. These noises were amplified by the FETs. Thus, a FET of higher sensitivity leads to a higher level of noises. Second, in a model describing the sensitivity of silicon nanowire transistors to the gate charge, the transistor's sensitivity would increase by decreasing the doping concentration. At the same time, lower doping concentration would elevate the noise level of the transistor. Therefore, we can conclude a positive relationship between the transistor sensitivity and the noise.

Characterization of the FET's Response Time to Input Gate Signals

The response time of an FET shows its switching characteristics. The typical switching frequency of the silicon FET is in the megahertz range, corresponding to the response time of hundreds even tens of nanoseconds. The response time of an FET is primarily affected by the input capacitance (such as the gate-source capacitance and gate-drain capacitance). For an FET sensor that interacts with cells, the FET must accurately retain fast and slow cellular signals, including opening and closing of rapid sodium ion channels (~1 ms), initiation of an action potential of cardiomyocytes (~1 ms), and activation of fast transient outward current of potassium ions and chlorine ions (<10 ms). It herein requires the FET to show the fast response to cellular signals with a wide bandwidth, which means the frequency range that the biosensor can maintain a stable amplitude of the detected signals. Within this range, the amplitude of the recorded signals by the FET is almost fixed with little fluctuations.

Figure 16A:
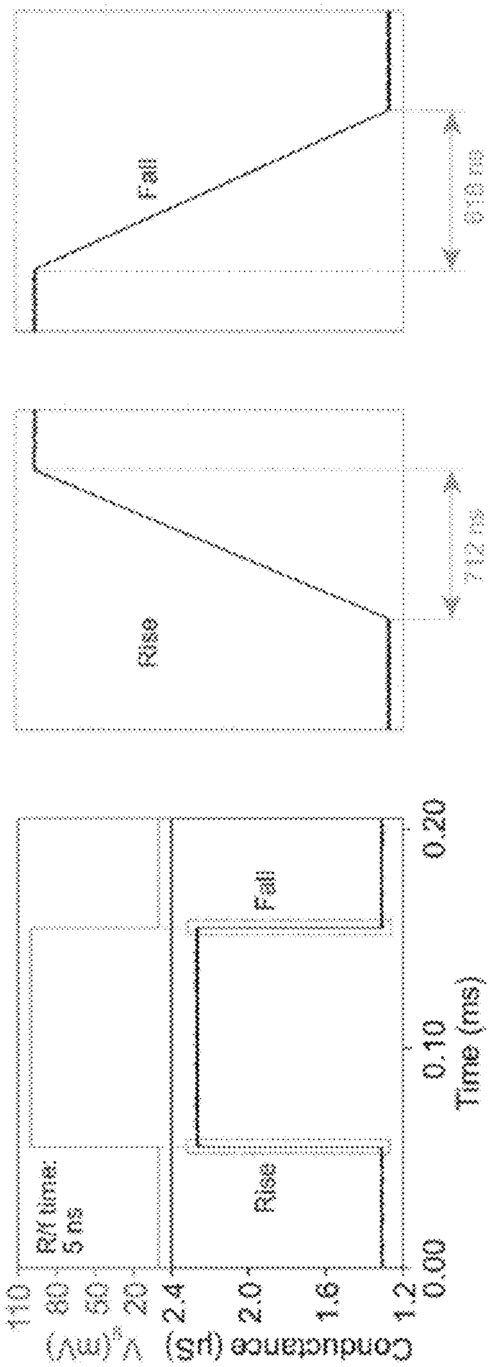
FIGS. 16A-16B show the FET's response characteristics to rapid and slow signals.

Here, we characterized the FET's response time by applying a rapid signal on its gate terminal using a similar configuration to that of the water-gate characterization. We used an arbitrary waveform generator (Model 3390, Keithley) to generate a pulse signal (rising/falling time: 5 ns, duration: 0.1 ms, amplitude 100 mV) and fed it to the FET. In FIG. 16*a*, the corresponding FET's output signal indicated a response time of 600~700 ns, much shorter than the recorded signal latencies between FETs, which were in the microsecond range. It proved the FET sensor had sufficiently fast response to external signals and therefore could faithfully record rapid cellular electrical signals.

Surface Functionalization of the FET by the Phospholipids

Two types of phospholipid bilayers were used in the experiments including a synthetic lipid bilayer and a natural cell membrane. These two types of lipid bilayer membranes had different advantages and were preferred in different applications. The natural cell membranes were structurally and functionally similar to those of the host cells so they could express specific cellular biomarkers (e.g., CD47) in the membranes to mimic the cellular surface to the greatest extent. Hence, we could use these natural cell membranes without additional modification. Red blood cell membranes have been widely used for nanoparticles coatings in fields of drug delivery, vascular injury repair, and tumor imaging because of the simplicity of the isolation process. On the other hand, the synthetic phospholipids showed higher flexibility for engineering and modification and superb stability. Besides, synthetic lipids were usually less expensive than natural cell-derived membranes.

Figures 18A, 18B, 18C, 18D, 18E, 18F, 18G:
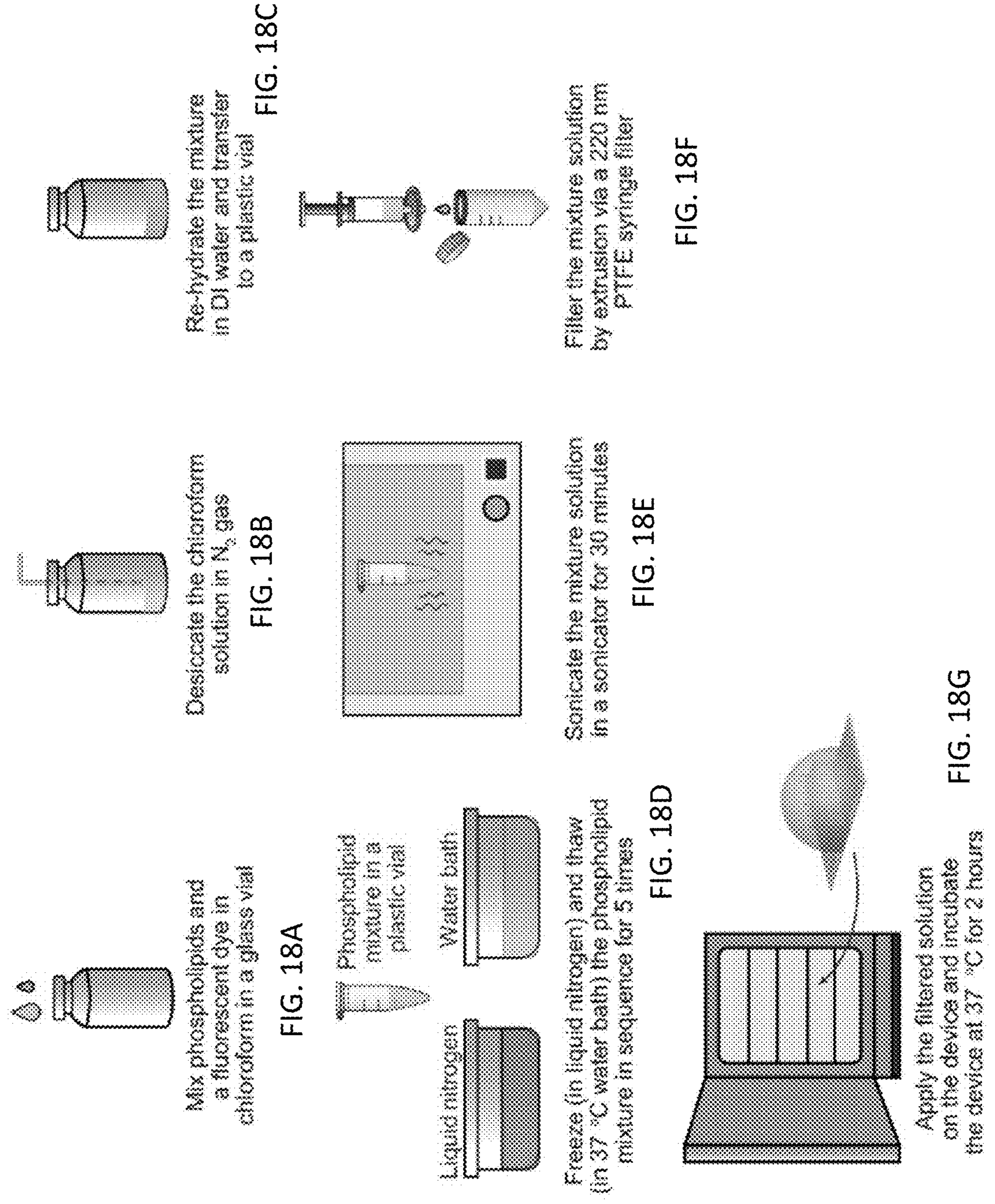
FIGS. 18A-18G show the schematic process of functionalizing the FET surface with phospholipids.
Figure 19A:
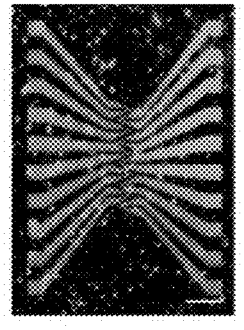
FIGS. 19A-19F show functionalization of the FET surface with phospholipids and equivalent circuit models of cellular measurements before and after FET internalization.
Figure 19B:
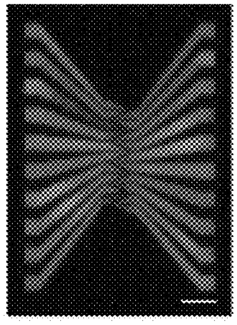
Figure 19C:
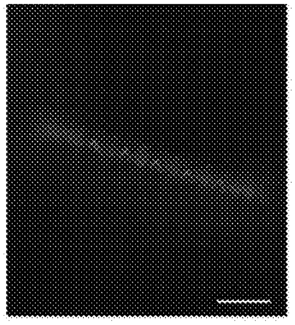
Figure 19D:
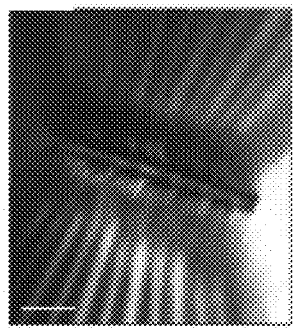
Figure 19E:
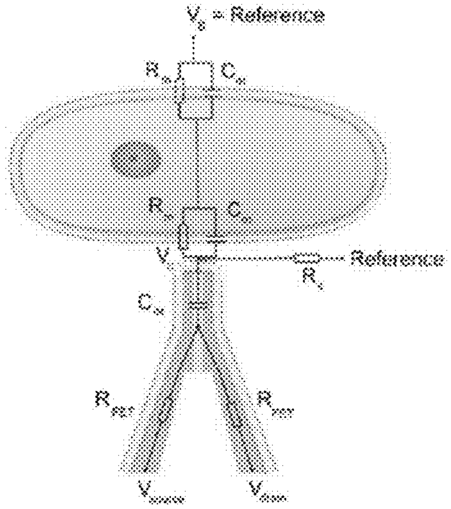
Figure 19F:
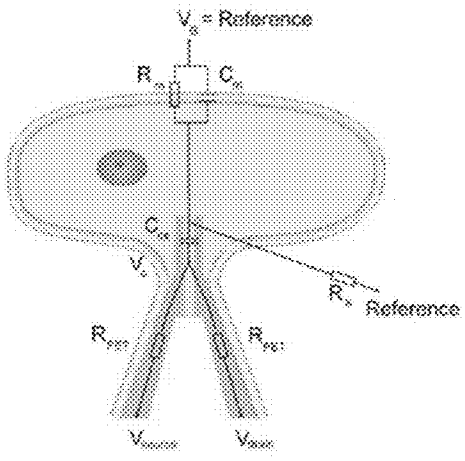
Figure 20A:
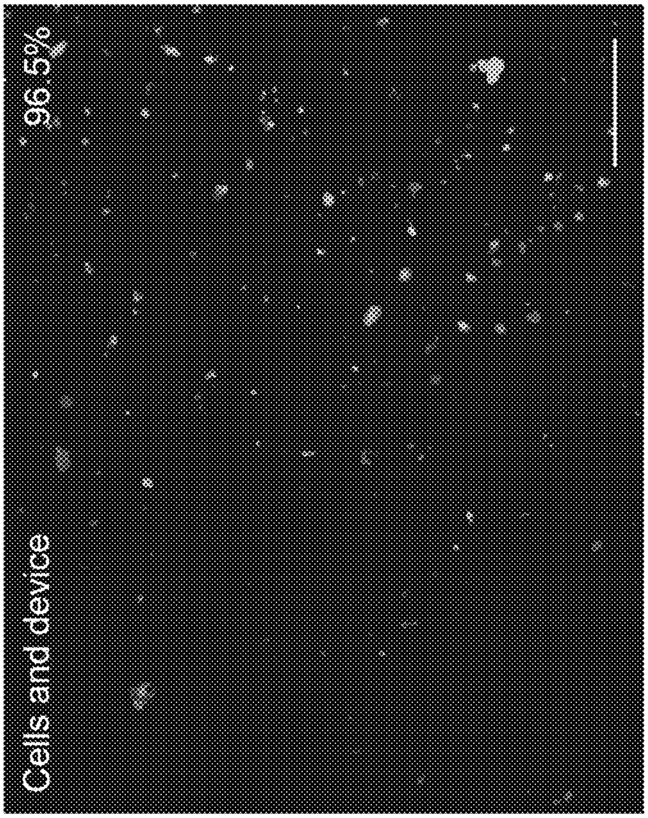
FIGS. 20A-20F show tests of cell viability.
Figure 20B:
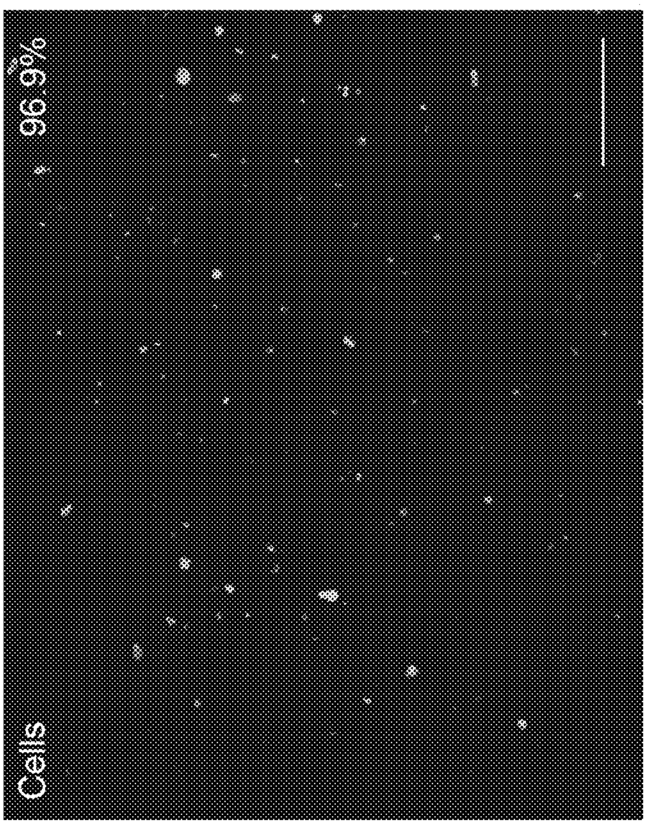
Figure 20C:
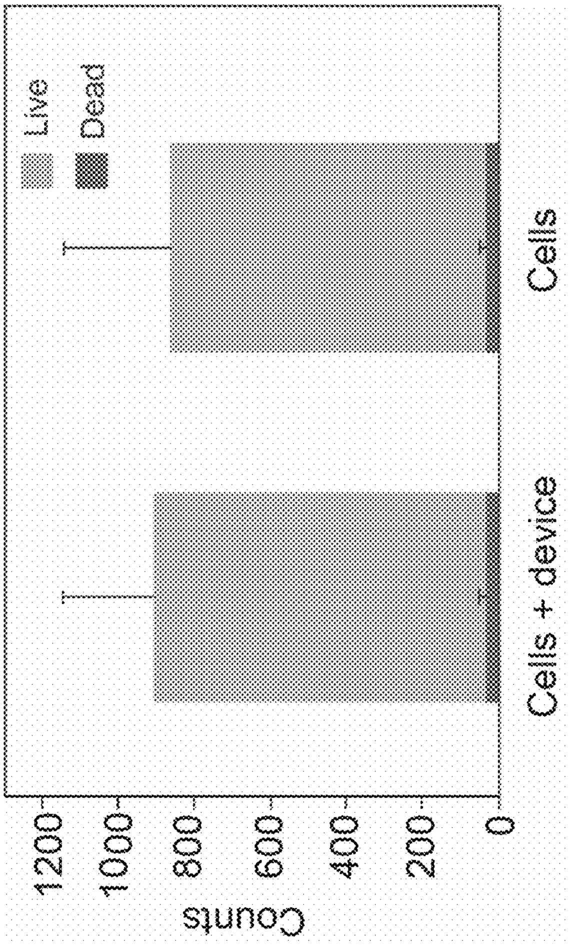
Figure 20D:
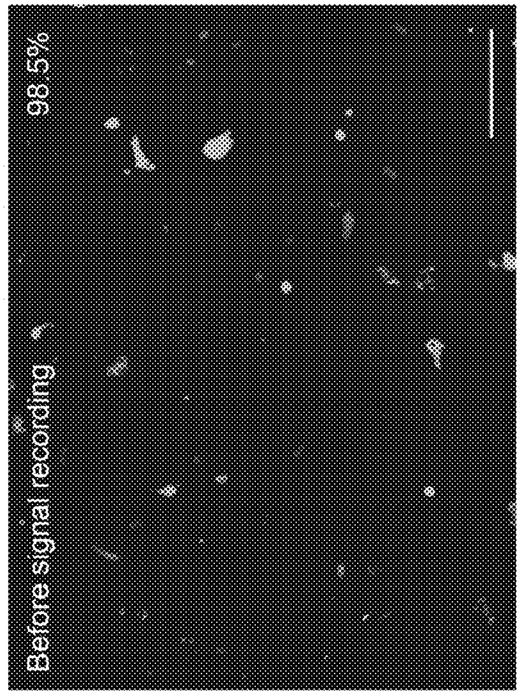
Figure 20E:
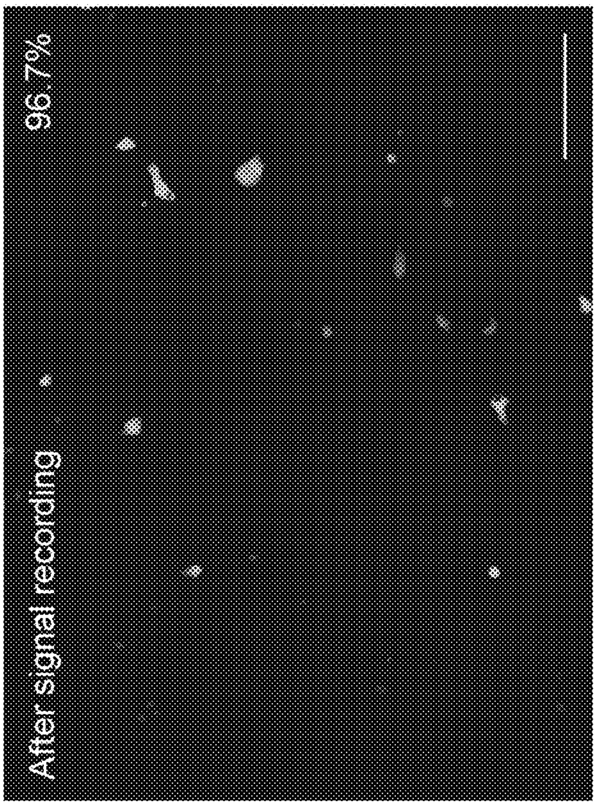
Figure 20F:
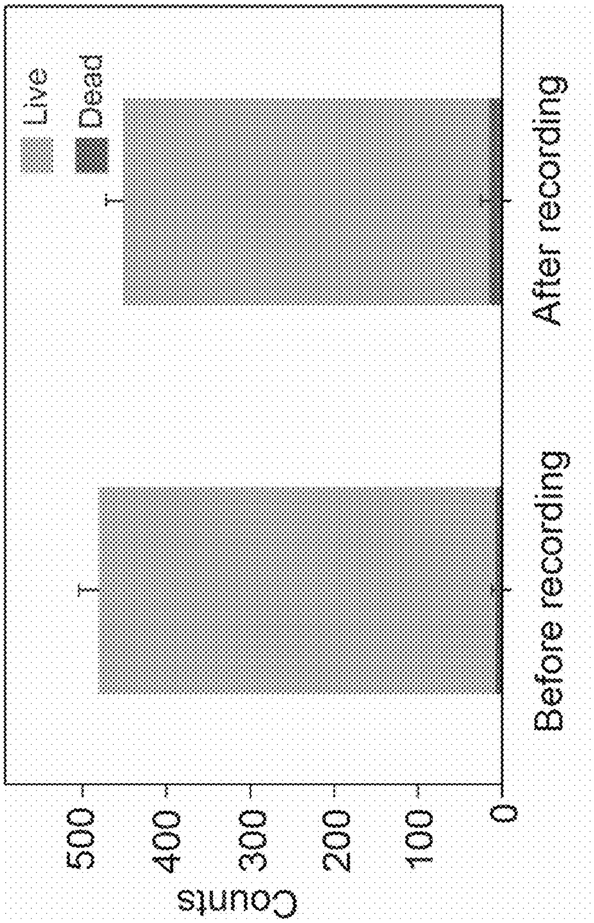

The synthetic lipid bilayer was made of DMPC (1,2-Dimyristoyl-sn-glycero-3-phosphocholine) from Avanti, and the extracted red blood cell membranes were obtained by following established protocols. We added the fluorescent material into the phospholipid bilayers for characterization purposes (FIG. 18*a*). We skipped this step when preparing the phospholipid coatings on the FET sensors used for signal recordings. Ideally, the lipid bilayer could naturally merge with the cell membrane. However, in reality, the spontaneous fusion would get affected by other materials in the cellular context, such as collagen. The fusion process took some time to form a perfect interface. Plus, the cell could expel the FET out of its body even after the sensor internalization (called the elastic response from the cytoskeleton). The coatings could be repeatedly used for intracellular measurements of different cells for about three times. After that, the phospholipid coating became worn and torn, making it difficult to get stable intracellular recordings, or even no signals at all.

The critical step in the preparation of the phospholipid bilayers was to generate high-surface-energy small lipid vesicles that could spontaneously form a lipid coating layer on the FET surface. A step-by-step description of the coating process is introduced below.

6.1. Removing the Organic Solvent in the Received Lipid Solutions

The received synthetic phospholipids were dissolved in chloroform solutions in glass vials. We removed the chloroform solvent and prepared aqueous lipid solutions. To achieve that, purging nitrogen gas overnight desiccated the chloroform thoroughly in a glass vial.

6.2. Re-Hydrating the Lipids in DI Water

The phospholipids were re-hydrated with the DI water and immediately transferred to a plastic vial. Here, importantly, using the plastic vials specifically was to prevent the hydrophilic segment of the phospholipid bilayer from attaching to the glass vial walls.

6.3. Breaking the Large Phospholipids Aggregates into Small Unilamellar Vesicles (SUVs)

The mixture in the aqueous solution underwent a freeze-and-thaw process (freeze in the liquid nitrogen and thaw in a water bath of 37° C.) for at least five times to break the multi-lamellar lipid vesicles into unilamellar vesicles. The later sonication treatment was also employed to disperse the lipid vesicles separately in the solution and eliminate any aggregation of small lipid vesicles. The next step of preparing the lipid solution was to extrude the mixture solution through a PTFE syringe filter. Only the small unilamellar vesicles would be left in the prepared solution. These SUVs had high surface energy so they could self-assemble to become a uniform lipid coating on the FET surface. Note that for natural red blood cell membranes, they are in bilayered vesicle structures upon collection for natural cells. They only need to undergo this extrusion process to generate unilamellar small vesicles.

6.4. Applying the SUVs Solutions on the FETs

To coat the lipid bilayers on the FETs, we applied the lipid solution to the FETs and put them in an incubator at 37° C. to sit for at least two hours. Spontaneous lipid fusion took place at such a higher temperature than the lipid's transition temperature (24° C. for DMPC). After that, removing the excessive lipid solutions gently by DI water completed the functionalization.

Fabrication of the Multi-Electrode Array (MEA)

The MEA in this study had multiple conductive electrodes that were extracellularly contacting cellular membranes and recording the membrane potentials. We used these devices to verify the cardiomyocytic electrophysiological activities. The collected extracellular signals served as a control for those recorded by the FET.

7.1. Cleaning the Glass Substrate

The first step was to clean cover glass slides (35 mm by 50 mm by 0.13-0.16 mm; Fisherbrand™) to remove all organic contaminants and particles in stabilized sulfuric acid and hydrogen peroxide mixture solution (Nano-Strip; VWR International, heating up to 80° C. for half an hour), followed by rinsing with DI water and drying with nitrogen gas.

7.2. Fabricating the Metal Connection Layouts

A lift-off process allowed forming metal connection patterns on the glass slides. The process involved photolithography (photoresist NR-3000PY: spin-casting at 4,000 r.p.m. for 60 s, baking on a hotplate at 150° C. for 60 s, UV irradiance at 220 mJ·cm$^{-2}$, post-exposure baking at 100° C. for 60 s, and developing for ~20 s with developer RD6) and then sputtering (chromium: 200 W, 3.0 mTorr, 5 sccm Ar, 30 s, ~5 nm; gold: 200 W, 3.0 mTorr, 5 sccm Ar, 5 min, ~100 nm). The samples were soaked in acetone overnight to thoroughly remove all photoresists and lift off the metals on the top of the photoresists.

7.3. Depositing the Insulation Layer

A thin layer of SU-8 was coated to insulate most of the metal wires and only expose the metal electrode pads, by photolithography (SU-8 2000.5: spin-casting at 4,000 r.p.m. for 30 s, baking on a hotplate at 95° C. for 60 s, UV irradiance at 100 mJ·cm$^{-2}$, post-exposure baking at 95° C. for 60 s, and developing for ~60 s with SU-8 developer). Hard baking at 180° C. for an hour cured the SU-8 completely so that the SU-8 was safe and compatible with cells during measurements.

7.4. Assembling a Container for the Cell Culture Medium

A conical centrifuge tube (Falcon™) was cut at 3 cm apart from the threaded dome. The flat top surface was adhered to the center of the MEA using a low toxicity silicone adhesive (Kwik-Sil™, World Precision Instruments) to build a container for the cell culture medium (FIG. 29*a*).

7.5. Wiring and Sterilizing the Device

We used silver epoxy (8831, MG Chemicals) to connect the metal leads of the MEA to flexible cables and the backend circuit. The device was sterilized in 70% ethanol for 5 hours before use.

Characterization of the FET's Sensitivity by the Water-Gate Method

The measurement system is illustrated in FIG. 15, where the FET was connected to preamplifiers, DAQ (e.g., Digi-Data 1440A), and downstream to a computer graphic user interface (GUI; for example, Axon pCLAMP 10 Software Suite).

The ionic solution such as the phosphate-buffered saline (PBS; Sigma-Aldrich, pH=7.4; temperature=37° C.) or typical Tyrode's solution (NaCl 140 mM, KCl 4 mM, $CaCl_2$ 1.8 mM, $MgCl_2$ 1 mM, HEPES (4-(2-hydroxyethyl)-1-piperazineethanesulfonic acid) 10 mM, glucose 10 mM, pH=7.35 with NaOH, temperature=37° C.) was added on the FET's gate surface. An Ag/AgCl electrode was immersed in the solution and applied a potential sweep from −100 mV to 100 mV to the solution. In the meantime, a positive potential (e.g., 200 mV) was fed to the FET's source terminal.

The FET's drain terminal conducted currents to the downstream preamplifier. With a change in the gate potential, the corresponding change in the source to drain current could be recorded and plotted in the GUI. The FET's sensitivity was finally defined by the slope of the FET's transfer characteristic plot.

It was notable that in the FET's temporal response to rapid signals (FIG. 2*g*-*i*), sometimes there was overshoot, which was caused by the capacitance between the metal wires, dielectric layers, and the ionic solution. These three layers formed a parallel plate capacitor. In the water-gate characterization, the ionic solution and thus the gate signal were covering everywhere. Therefore, the metal-induced capacitance would affect the characterization result. However, in the cellular measurement, the local cellular signal is applied to the FET locally, but not on anywhere else, so we could safely neglect the capacitance effect in the cellular measurements.

HL-1 Cell Culture Protocol

The HL-1 cardiomyocytes were purchased from Sigma-Aldrich.

To prepare the cells for signal recordings, the cells were cultivated on thin PDMS sheets (base material: curing agent=10:1; prepared by spin-casting the mixed precursors on a 4-inch wafer at 500 r.p.m. for 60 s, baking in a convection oven at 80° C. for 4 hours).

Before cell plating, the PDMS sheet was cut into 3 cm by 3 cm square and placed in a 35 cm cell culture dish. The PDMS sheet was soaked in 70% ethanol for 30 min, followed by ultraviolet sterilization for 1 hour. Fibronectin/Gelatin (5 $\mu g \cdot ml^{-1}$ fibronectin in 0.02% gelatin solution, 1 ml) was coated on the pre-treated PDMS surface for at least 1 hour before seeding the cells.

After removing the coating agent, the cells (at a density of $\sim 1 \times 10^5$ $cm^{-2}$) were plated and maintained in the supplemented Claycomb medium (10% fetal bovine serum, norepinephrine 0.1 mM, L-Glutamine 2 mM, and penicillin/streptomycin 100 $U \cdot ml^{-1}$/100 $\mu g \cdot m^{-1}$, 2 ml) in an incubator at 37° C. and 5% $CO_2$. The cell culture medium was replaced by a 2 ml fresh medium every day until the cells reached confluency in 3-4 days.

Sterilizing the MEA and the FET before plating the cells followed the same procedure as the abovementioned. Fibronectin/Gelatin was coated on the MEA surface before cell seeding to enhance cell attachment.

Primary Cardiomyocyte Culture Protocol 10.1. Neonatal Mouse Cardiomyocytes

The neonatal mouse ventricles were predigested in HBSS (Hank's Balanced Salt Solution) (0.5 $mg \cdot ml^{-1}$) containing Trypsin (0.5 $mg \cdot ml^{-1}$) at 4° C. on an orbital shaker at 80 r.p.m. for overnight, and then were thoroughly digested in collagenase (330 $U \cdot ml^{-1}$) and HBSS (0.8 $mg \cdot ml^{-1}$) mixed solution.

Isolated cells were suspended in the cell culture medium (Dulbecco's Modified Eagle Medium: M199=4:1 in volume, penicillin/streptomycin 120 $U \cdot ml^{-1}$/100 $\mu g \cdot m^{-1}$, L-Glutamine 2 mM, HEPES 10 mM, 10% Horse Serum, 5% Fetal Bovine Serum). The cells were plated in a T-75 flask to remove the adherent fibroblast cells.

The suspended cardiomyocytes were transferred to a PDMS sheet in a 35-cm dish pre-coated with laminin (1 $\mu g \cdot ml^{-1}$ laminin in sterile 1×PBS). The cells were incubated at 37° C. in a humidified incubator with 10% $CO_2$. The medium was replaced on a daily basis.

10.2. Adult Mouse Cardiomyocytes

Adult mouse hearts were isolated via aortic perfusion with a buffered perfusion solution (NaCl 113 mM, $Na_2HPO_4$ 0.6 mM, $NaHCO_3$ 12 mM, KCl 4.7 mM, $KHCO_3$ 10 mM, $KH_2PO_4$ 0.6 mM, $MgSO_4.7H_2O$ 1.2 mM, HEPES 10 mM, Taurine 30 mM, phenol red 0.032 mM, glucose 5.5 mM, temperature=37° C.; pH=7.35 with NaOH) to fully remove all blood from the vasculature. A 1 mg/mL collagenase type 2-containing digestion buffer digested the matrix of the heart during perfusion at a rate of 3 $ml \cdot min^{-1}$. Once the heart was sufficiently digested, the ventricles were removed and minced with scissors before being triterated in warmed solution (90% perfusion solution, 10% fetal bovine serum, 12.5 uM calcium chloride) with a transfer pipette. Cells were strained through 100 um mesh and stepwise, slowly brought to 1 mM calcium concentration. Then they were transferred to a 35 cm dish pre-coated with laminin (1 $\mu g \cdot ml^{-1}$ laminin in sterile PBS solution). The cells were incubated at 37° C. in a humidified incubator with 5% $CO_2$ for 4 hours before measurements.

Electrophysiological Measurements by the Whole-Cell Patch-Clamp

Whole-cell current patching on HL-1 cells and primary cardiomyocytes were performed with external solution (for all types of cells: NaCl 140 mM, KCl 4 mM, $MgCl_2$ 1 mM, HEPES 10 mM, glucose 10 mM, temperature=37° C.; for HL-1 cells: $CaCl_2$ 1.8 mM, pH=7.35 with NaOH; for primary cells: $CaCl_2$ 1.0 mM, pH=7.4 with NaOH).

Glass pipettes were pulled from borosilicate glass using a micropipette puller (Model P-87, Sutter Instrument Co.). The as-pulled glass pipettes were then filled with an internal solution (NaCl 10 mM, KCl 10 mM, K-Aspartate 120 mM, $MgCl_2$ 1 mM, HEPES 10 mM, MgATP 5 mM, pH=7.2 with KOH). The glass pipettes had an average impedance of 2-5 MΩ measured in the cell medium bath.

Junction potentials were zeroed before the formation of the membrane-pipette sealing. Several minutes after the seal was formed, the membrane was ruptured by gentle suction to establish the whole-cell configuration for current clamping. Cell capacitance was measured by integrating the capacitive transient evoked by applying a 5 mV hyperpolarizing step from a holding potential of −40 mV.

Figure 23:
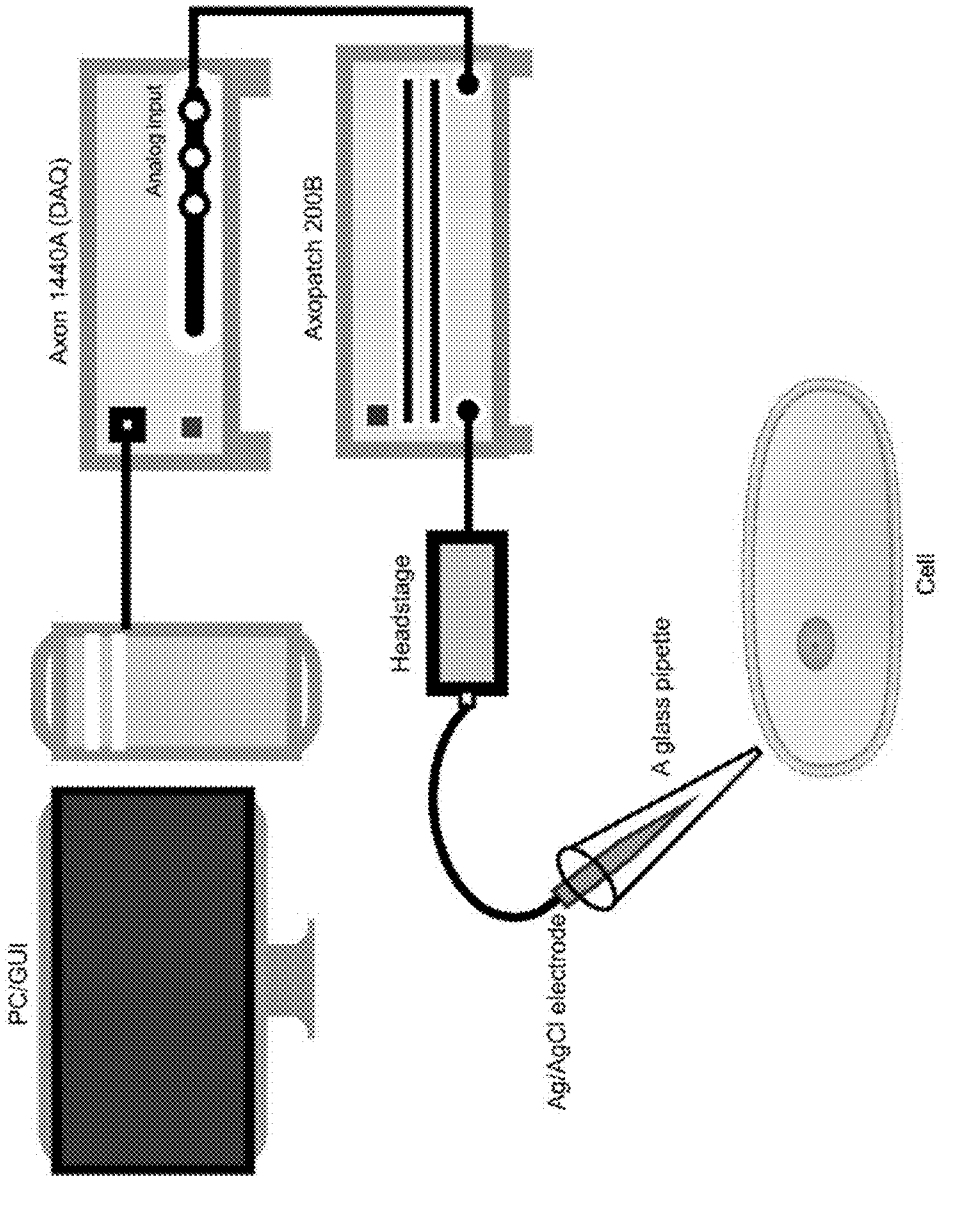
FIG. 23 shows the schematic experimental setup of using the patch clamp to record intracellular signals of a single cell.

Schematics in FIG. 23 illustrate the electrical system of the patch-clamp platform, including an Ag/AgCl electrode connected with a headstage for amplifying the recorded signals by a feedback circuit. The headstage connected to an amplification system (Axonpatch 200B) and a data digitalization module (DigiData 1440A, Axon). Current-clamp command pulses were generated by a digital-to-analog converter (DigiData 1440A, Axon) controlled by the pCLAMP software (10.3, Axon). After the cells were stimulated by an injection current, action potential spikes could be recorded and shown in the GUI.

The small discrepancy between the results from the FETs and the patch-clamp is within the standard cellular signals' fluctuation range due to differences in cellular physiology and measurement setups.

Electrophysiological Signal Acquisition 12.1. The Acquisition System for the 10-FET Array The experimental setup for sensing cellular electrophysiology by the 10-FET array consisted of a commercial DAQ system (DigiData 1440A) and a customized 10-channel preamplifier shown in FIGS. 31 and 32. The setup was similar to that used for water-gate characterization, where cells were placed on the FET with a zero bias from the Ag/AgCl electrode. The sampling rates applied for the recordings were within the range from 10 to 100 kHz.

Figure 30A:
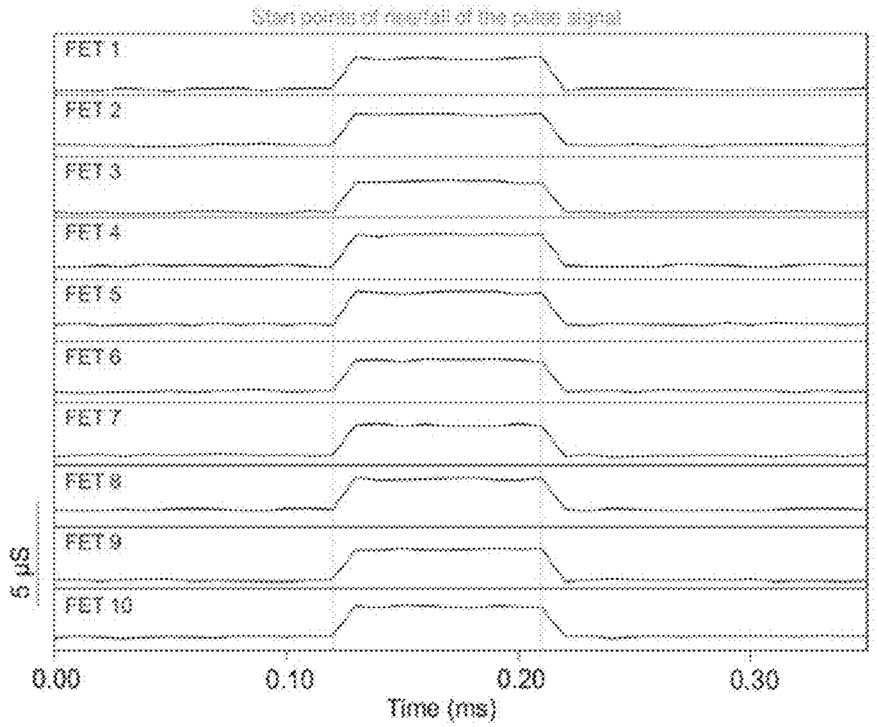
FIG. 30A-30B show characterization of the electrical signal delay introduced by the measurement system.
Figure 30B:
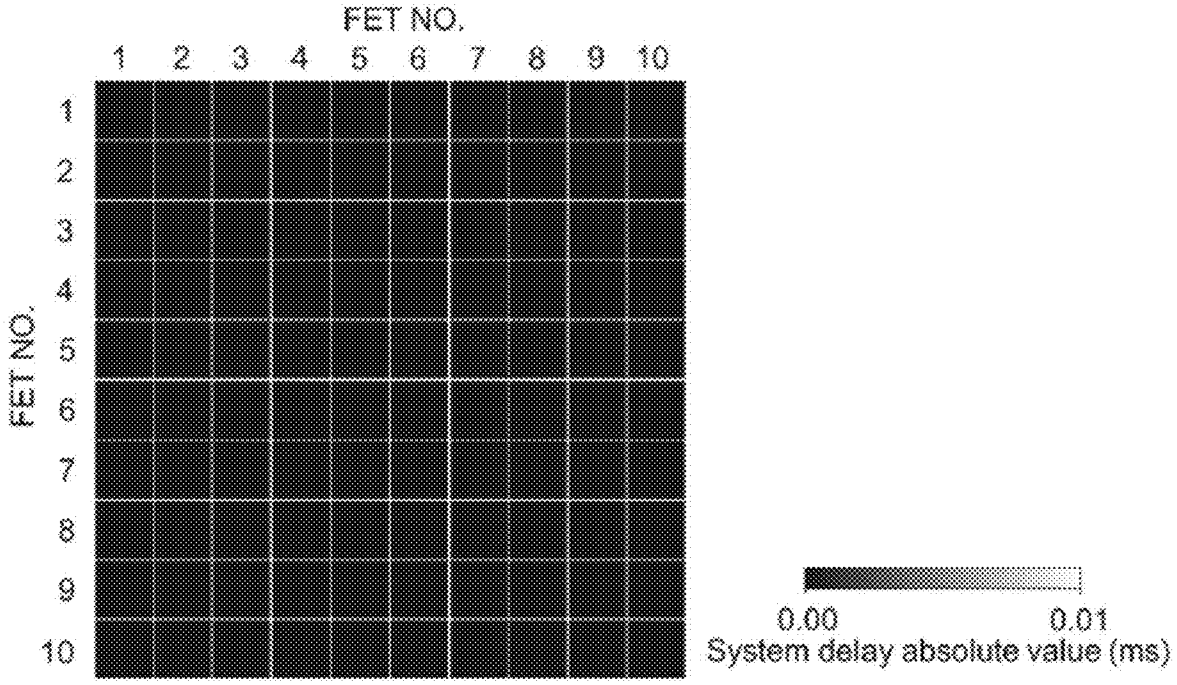

Electrical characterization showed no crosstalk between different channels in the preamplifier (FIG. 33). By hooking up the preamplifier to the DAQ, PC, and the 10-FET array, each FET in the array operates independently, showing no crosstalk with each other (FIG. 30).

12.2. The Acquisition System for the 128-FET Array

The DAQ system consisted of a DDC264 (Texas Instruments) and a customized acquisition interface to the evaluation board (FIG. 42). The DAQ was connected to the FET sensor arrays using ACF cables and an adaptive printed circuit board. Customized software (Texas Instruments) controlled the DAQ system. All recordings by the 128-FET array in this study used a sampling rate of 500-1,000 Hz, which was large enough to ensure the signal's fidelity, and small enough to meet the limited capacity of the chip memory for on-board data storage.

Signal Processing and Analysis 13.1. Calculations of the FET's Sensitivity and Noise Level The FET's sensitivity and noise level were analyzed and computed in MATLAB. The sensitivity was represented by the slope of the FET's water-gate characterization plot. To obtain the slope, a linear fitting of the plot was performed. The noise's amplitude was calculated from the same plot. First, we substituted every gate potential (x-coordinate) into the fitting function to get a new set of values, which represented the recordings without noise. Second, we subtracted the new values from the originally recorded (y-coordinate) values and got the pure noise signals. Third, the difference between the maximal and minimal values of the noise signals represented the peak-to-peak amplitude of the noise.

13.2. Signal Latency Calculation by the Cross-Correlation Method

Figure 36A:
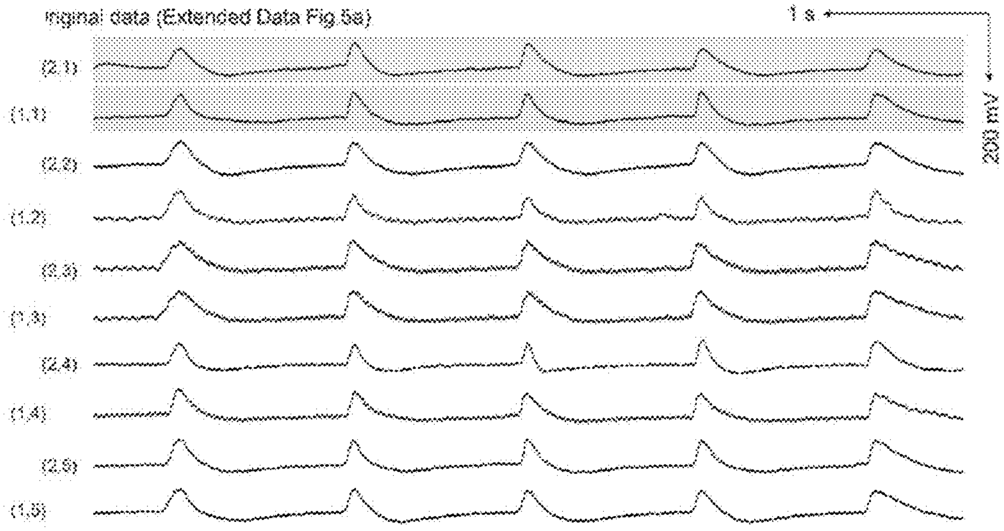
FIGS. 36A-36B show the cross-correlation method.
Figure 36B:
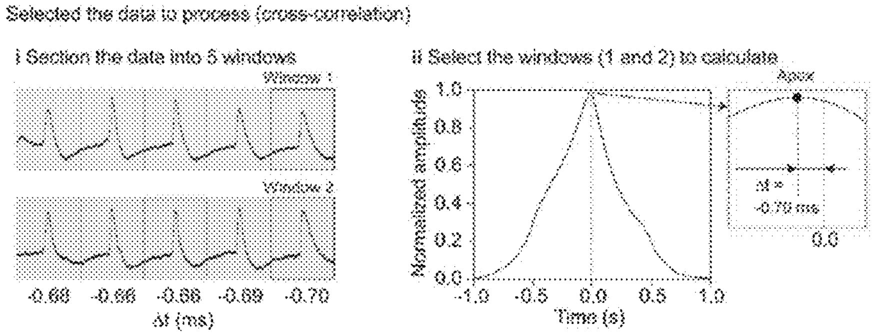

FIG. 36 introduces the cross-correlation method to calculate the latency between two action potential spikes. The computation was conducted in MATLAB using the cross-correlation function. To calculate the latency between any two action potentials, we first chose the simultaneous recordings from different FET sensors, such as (2,1) and (1,1) in FIG. 35. We selected a fixed duration of data that contained an action potential recorded by (2,1) and (1,1). The latency between these two data sections was calculated by the cross-correlation method.

Justification of the Action Potential Morphologies

Cells show different physiological characteristics even though they are of the same type or even in the same cell culture. For example, in the same culture, some cells are contractile, but some are not; also, some cells are spontaneously firing action potentials, but some are not. Their actual action potential shapes of different cells would have slight differences as well. Plus, as a cancerous cell line, HL-1 cells would mutate during proliferation and reproduction, so their physiological characteristics would vary from different cell passages (i.e., how many times they have reproduced themselves). In different literature, the action potential morphologies of HL-1 cells were not identical.

Modulation of HL-1 Cells' Electrophysiology by Adding Drugs or Changing the Ion Concentrations in the Culture Solutions Cellular electrophysiology can be modulated by drugs. These drugs act as ion channel blockers that can affect ionic influx and/or efflux across the cellular membrane so they can modulate cellular electrophysiology that can be reflected by the action potential morphology. In this work, the cells' responses to nifedipine or tetrodotoxin (TTX) were studied. Nifedipine is an L-type calcium ion blocker and TTX is a sodium ion blocker. To prepare the drug solutions, we added nifedipine or TTX to the typical Tyrode's solution.

Changing the ion concentrations in the extracellular medium would also impact cellular electrophysiological characteristics. For instance, abnormal solutions with above normal potassium concentration (a.k.a. hyperkalemia) or below normal sodium concentration (a.k.a. hyponatremia) in the culture medium can interfere with the proper electric signals. In this experiment, we prepared solutions containing doubled concentrations of potassium ions for hyperkalemia and half concentrations of sodium ions for hyponatremia studies.

After the drugs or the abnormal solutions were administered to the cells, it took several minutes to affect the action potential recordings. Replacing the solutions with drugs or abnormal concentrations of ions back with the typical Tyrode's solution by perfusion would recover the cell's normal electrophysiological characteristics.

Cardiac Microtissues Engineering 3D microtissues exhibit large similarity to the native tissue in the natural state, providing value for studying organ development, disease progression, and effectiveness of certain drugs. Therefore, it is attracting more attention as the biological model for pathology and pharmaceutical studies of cardiovascular diseases.

Figure 45C:
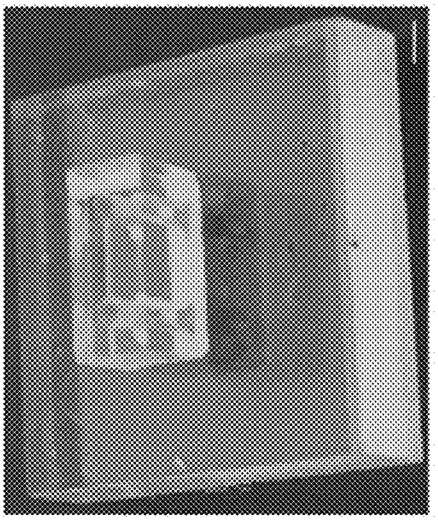
FIG. 45A-FIG. 45 E show fabrication processes of the PDMS platform for cultivating cardiac microtissues.
Figure 45B:
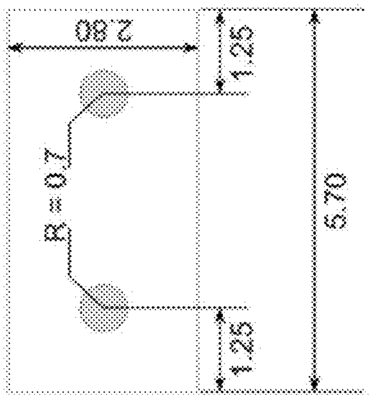
Figure 45A:
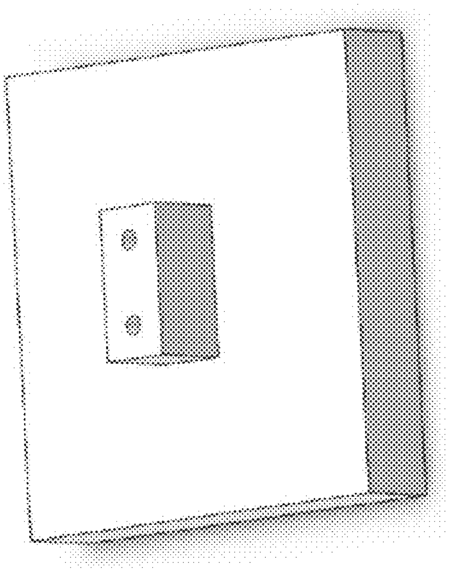

The PDMS platform consisted of two or more micro-posts and one well to construct the microtissues was fabricated. A master mold was designed using AutoCAD (Autodesk Inc., USA) and made of PMMA using laser ablation (FIG. 45*c*). Sticking the PMMA to the Petri dish formed a mold for curing PDMS (Dow Corning, Sylgard™ 184, USA, base: curing agent ratio 20:1, heated at 80° C. for 2 hours, FIG. 45*d*). After proper sterilization, the fabricated PDMS platform (within the well and around the microposts) was filled with a collagen-based hydrogel with a density of 3 $mg \cdot ml^{-1}$. The cell culture media was a mixture of Dulbecco's Modified Eagle Medium (DMEM) (Gibco, USA), 10% fetal bovine serum (Gibco, USA), and 1% penicillin-streptomycin (Lonza, USA). Cells were incubated at 37° C. with 5% $CO_2$.

Figure 41:
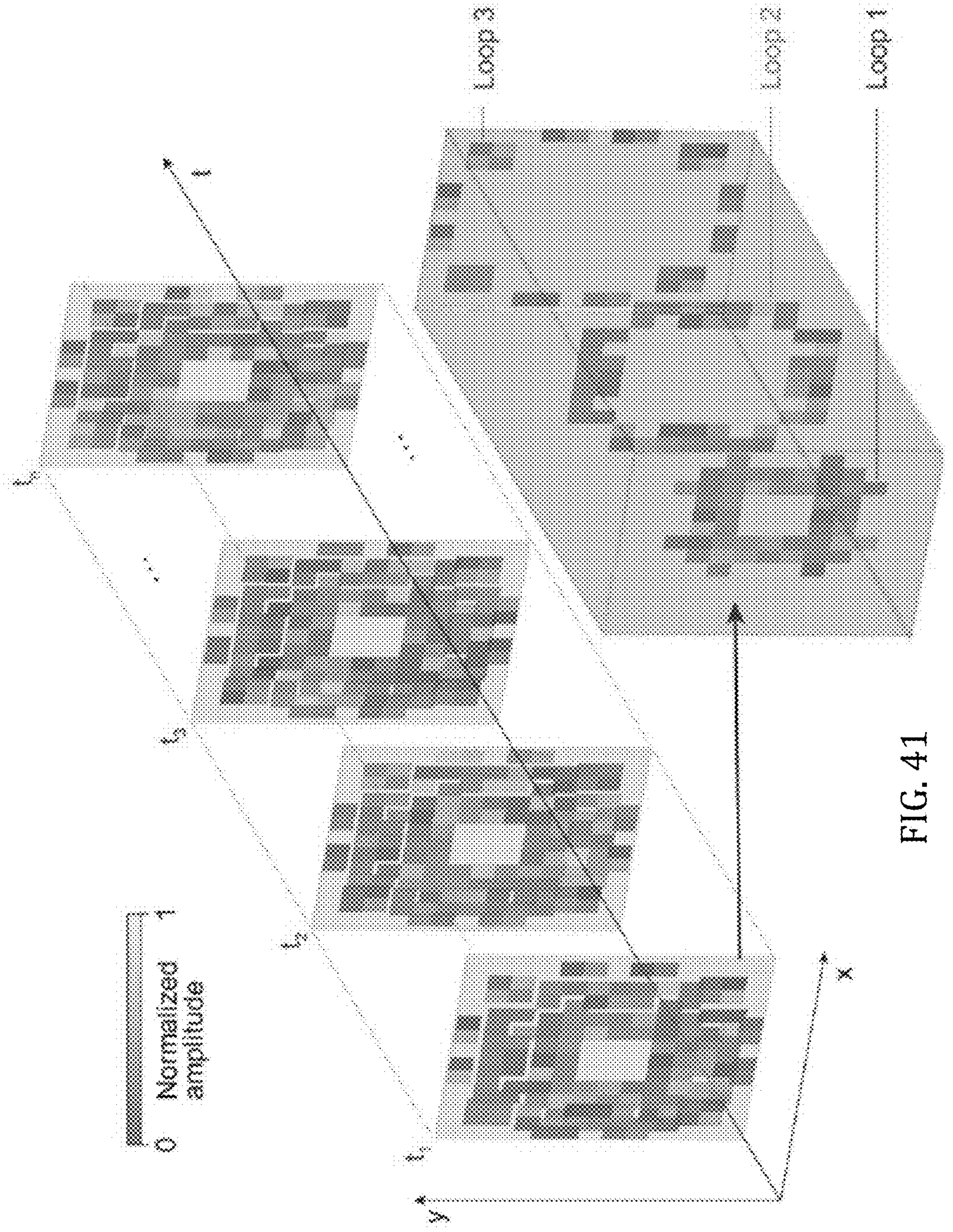
FIG. 41 shows the organization of the 128-FET array and display of data.
Figure 41B:
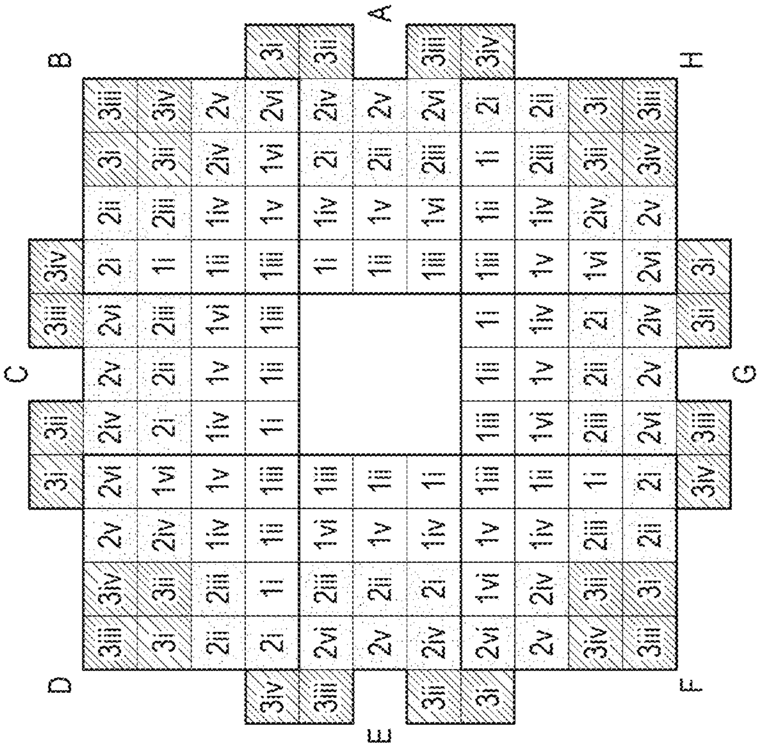
Figure 41A:
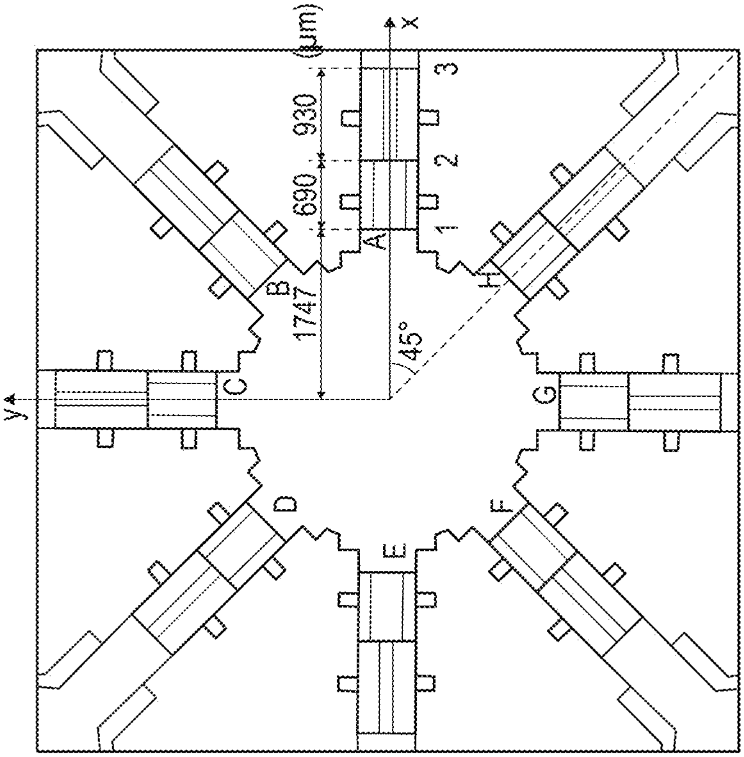
Figure 41C:
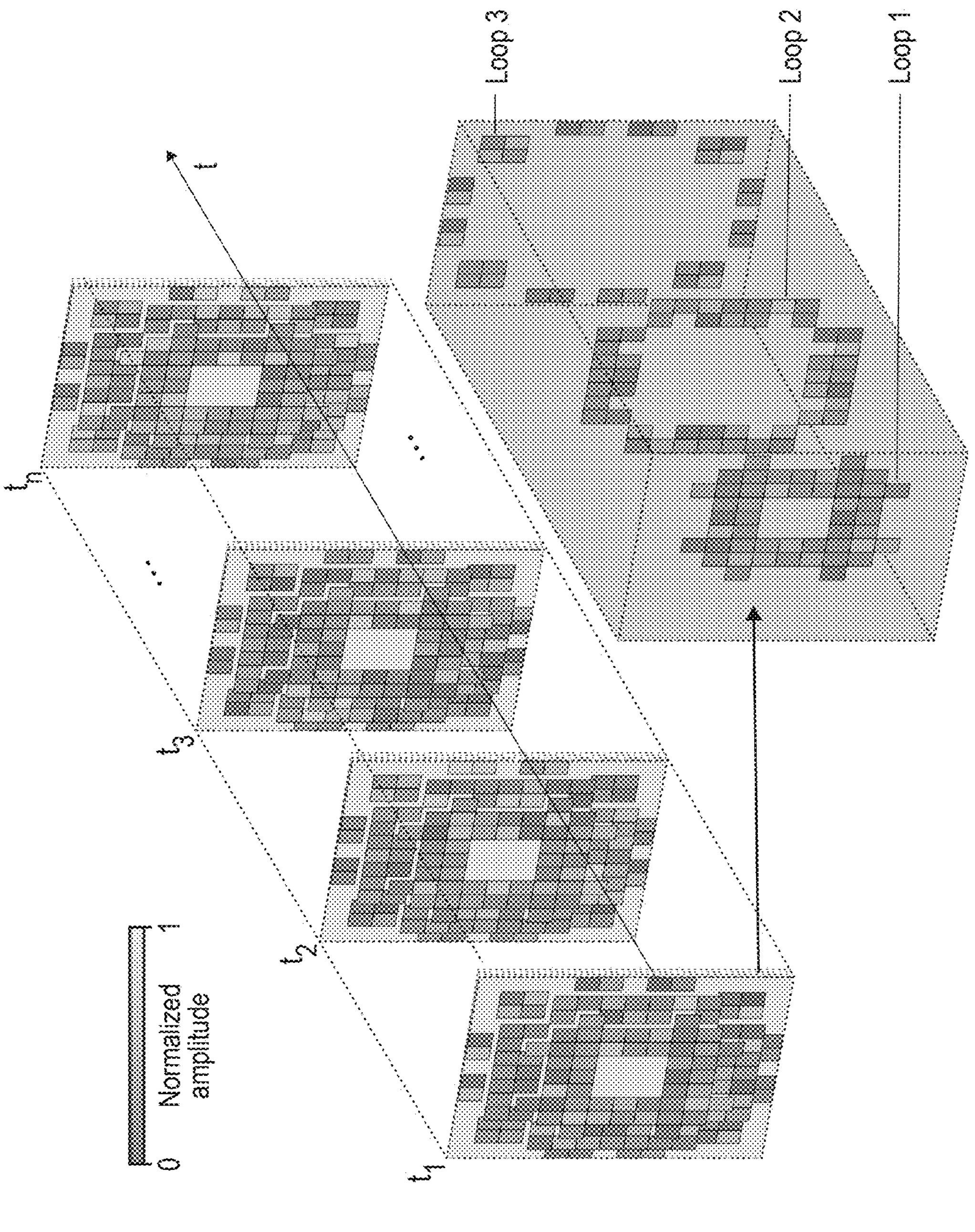
Figure 42A:
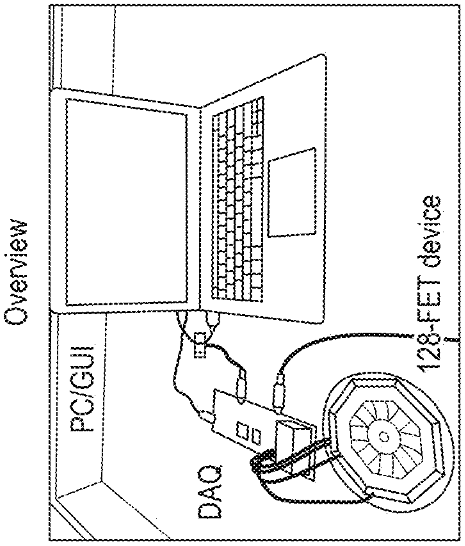
FIG. 42A-42D show pictures of the experimental setup of recording electrophysiology of the 3D cardiac tissue by the 128-FET array.
Figure 42B:
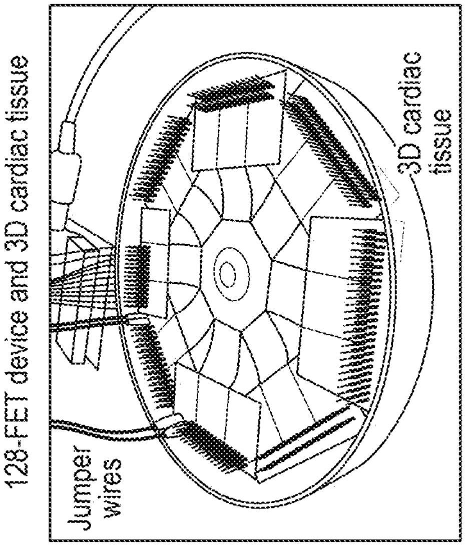
Figure 42C:
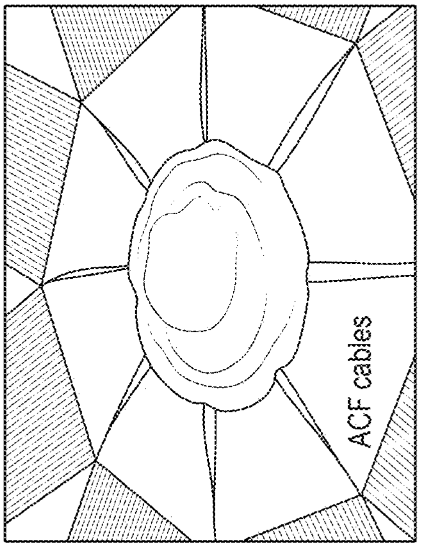
Figure 42D:
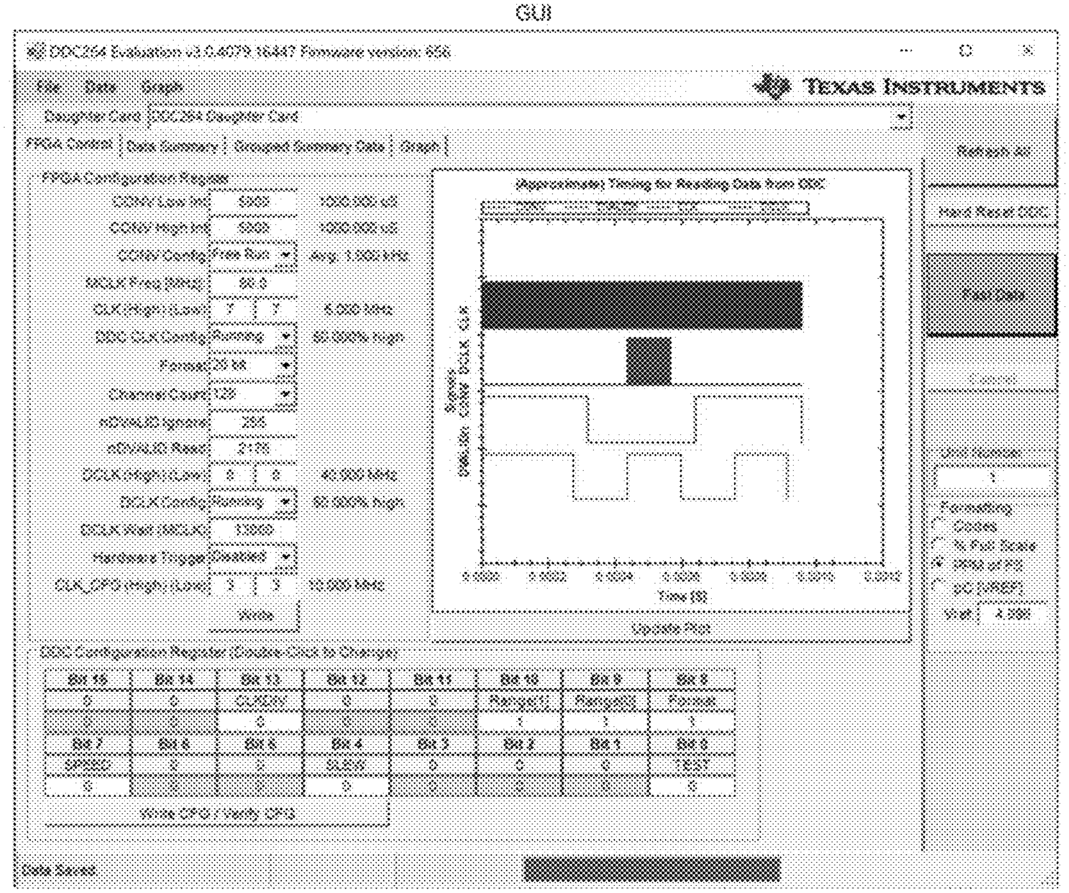
Figure 45E:
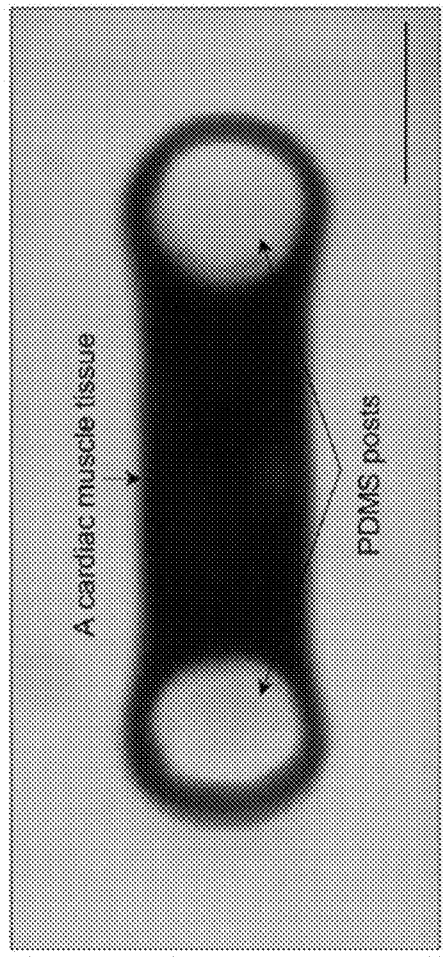
Figure 45D:
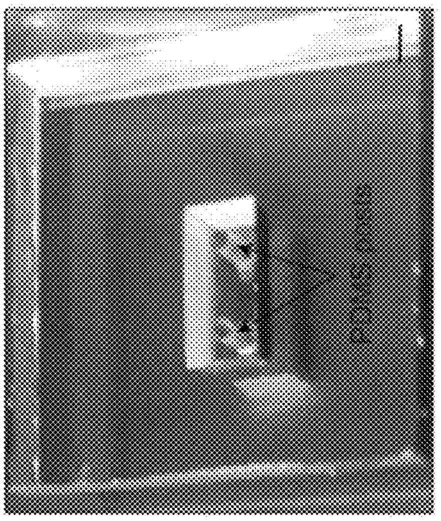

Measurements were conducted three days after cell seeding in the PDMS platform and forming the tissue compaction (FIG. 45*e*). FIG. 41 shows the measurement setup of the 128-FET array, which included a customized DAQ system based on a commercial current input analog-to-digital converter (TI DDC264). Each channel could operate independently with no crosstalk. The system had a fixed amplification of 13.81 $V \cdot nA^{-1}$ (FIG. 42).

Fluorescence Staining of the HL-1 Cells and the FET

We conducted fluorescence staining and confocal microscopy imaging to show the cell/FET interfaces. In this work, live cell staining was performed using NucBlue (ThermoFisher Scientific) and CellBrite (Red; Biotium). The HL-1 cells were incubated at 37° C. for 15 minutes and 20 minutes after adding CellBrite and NucBlue dyes, respectively. To visualize the FET device, we mixed 0.1 $mg \cdot ml^{-1}$ rhodamine 6G dye (Sigma Aldrich) in the PI layer during the device fabrication. The device would emit green fluorescence, as shown in FIG. 4*f* and FIG. 39.

Confocal imaging was carried out using a Leica SP8 confocal microscope with lightning deconvolution. Confocal images were acquired using 405, 647, and 488 nm to excite components labeled with NucBlue, CellBrite, and Rhodamine 6G fluorescent dyes, respectively. Fiji (ver. 2.1.0/1.53c) was used for analyzing the confocal images.

Additional Description of FIG. 6-FIG. 46

FIG. 6 show a series of schematically illustrated steps showing the fabrication steps of the 3D FET array. a, The FET's drain, source, and gate regions are determined on an n-type SOI wafer by doping. First, the undoped region (i.e., the region with only the background doping from the wafer) is coated by a layer of $SiO_2$ as the barrier for spin-on dopants from diffusing into the silicon substrate. Second, the FET shape is defined by photolithography and reactive ion etching. b, The FETs are firstly anchored to the substrate by PTFE, and then are transferred using a PDMS stamp to a temporary 2D substrate coated with PI. c, Multi-layered polymers and metal are coated and patterned on the temporary substrate. Finally, the layered device is transferred to a PDMS stamp and picked up by a water-soluble tape. d, The FET array is transferred to a prestrained elastomer substrate and selectively bonded at the two pre-designed bonding sites. When the prestrain releases, the 2D FET array gets compressed and buckled up to form 3D geometries.

FIG. 7 maps the FET's conductivity by an atomic force microscope with a bias applied by the scanning tip. a, A linear scan of the FET's conductivity was performed with a positive bias by the atomic force microscope. The results show a larger positive bias applied on the FET's lightly doped conduction channel yields a larger conductivity in the channel, which verifies the n-type properties of the FET's channel, which corresponds with the results by electrical transport characterizations. Scale bar: 2 μm. b, Original data points from the conductivity linear scan showing the FET's conduction channel turns "ON" at the 1 V tip bias. The "threshold voltage" didn't appear in the water-gate characterization because we use a much smaller gate bias range for scanning the water-gate characterization. Additionally, we expect the FET device is "ON" at zero bias because the middle region is also n-type with lots of free electrons. The discrepancy between the two measurements is from their different characterization mechanisms, including the gate capacitance, method of applying the gate bias, and the information that can be read from the signals.

FIG. 8 show data for optimizing the FETs' electrical properties by tuning doping concentrations. a, Sheet resistances of (i) antimony doped SOI (N-type) and (ii) boron doped SOI (P-type) wafers, determined by high-temperature doping with phosphorus dopant (P509) at 950° C. for various doping times (Δt), which is defined as the period that the apex temperature was held during annealing. b, A typical temperature profile for driving the phosphorus dopants into the SOI wafer. The most effective doping period was at the highest temperature (950° C.), as indicated by Δt. A longer Δt generates a smaller sheet resistance of the SOI. We applied a two-step doping process: the first light doping was for the whole SOI that determined the FET's conduction channel's doping concentration; and the second heavy doping was for the whole SOI except the conduction channels. The resultant FET had an $N^+NN^+$ structure and worked under a depletion mode. c-e, Transfer characteristics of devices by various doping conditions, including (c) undoped, (d) selectively doped, and (c) heavily uniformly doped sensors. f, Transfer characteristics of (i) p-type and (ii) n-type depletion-mode FETs, showing that the n-type FETs demonstrate about six times larger transconductances (i.e., sensitivities) than those p-type FETs. Therefore, we chose n-type depletion-mode FETs in this work.

FIG. 9 illustrates the FETs' reliability tests under various conditions. i, An FET's conductance with different pH of the gate solution. The transfer characteristics show high similarities, proving high reliability of the FET under various pH. The common pH for cell culturing is 7.4. ii, Extracted data points at zero gate bias, showing the conductance decreases with increasing the pH, giving another evidence of the n-type conductivity of the FET. b, i, An FET's transfer characteristics under different temperatures of the gate solution, showing the FET has excellent thermal stability and reliability under various temperatures. The common temperature for cell culturing is 37° C. ii, Calculated transconductances showing the FET's transconductance decreases with increasing the temperature, which is due to the effectively reduced mobility of the charge carriers in the conduction channel. c, Parylene C was used as an additional gate dielectric material on top of the $SiO_2$ in the FET, considering $SiO_2$ might be soluble in biological fluids, such as extracellular solutions of cardiac muscle cells. The FETs' transconductance (i.e., sensitivity) barely changed after coating the Parylene C.

FIG. 10 shows recordings of HL-1 cells' action potentials by a 10-FET array under electrical stimulation. a, Changing the stimulation electrode orientation from northwest (nw) to northeast (ne), southwest (sw), and southeast (se) will shift the directions of intercellular signal conductions. The first signal appeared in the FET that is relatively closer to the stimulation electrode and propagated among the cells per their coupling states, as indicated by the black arrows. The intercellular signal conduction velocity under electrical stimulation is from 35.1 to 39.3 $\mu m \cdot ms^{-1}$. The variations in the velocity are caused by the fluctuations of temperature, pH value, and ion concentration in the cell culture medium. In all scenarios, the directions of intracellular signal conductions, as indicated by the arrows, are always the same, i.e., from (1,3) to (2,3). b, Schematics showing the latencies of intracellular signal conductions from (1,3) to (2,3).

FIG. 11 shows small-scale signal conduction within the cardiac tissue by the 128-FET array. The 128-FET array is classified into 40 units, where each arm has five units. Each unit is labelled by the combination of the located arm name (e.g., "A"), the loop number (e.g., "1"), and the relative location (e.g., "a"). In each unit, the FETs are labelled in i, ii, iii, and iv. Within each unit, intercellular signal conductions via gap junctions in neighboring cells are analyzed, and the latencies are denoted in the heatmaps. The signal conduction velocity inside each unit can be calculated. For instance, in E2b, the signal transmits 70 μm from E2iv to E2vi in 5 ms. By analyzing all signal conductions within each unit, we calculated the small-scale conduction velocity (Table 5), whose average and standard deviation are 18.8±7.5 $\mu m \cdot ms^1$, which are consistent with previously reported values. The triangle for each unit indicates the selected FET that has the earliest spike within that unit. We use the selected FET in each unit as the reference point to calculate the signal conduction velocities among different units. NaN: Not a number, meaning no cellular signal was recorded.

FIG. 12 shows the structural design of the arrayed FETs. a, Schematics showing the design principle of the 2D precursor of a 10-FET array. The applied prestrain on the dragon skin elastomer is defined by (L2−L1)/L1. b, The CAD designs of the FETs showing the unique features of every layer of the device. Each layer has four alignment markers at corners for photolithography. (i) The doping line is 0.8 μm wide by photolithography. ii, The sensors' tips are 1-2 μm wide, which can provide high sensitivity and spatial resolution while minimizing invasiveness to the cells and forming tight sealings during measurements. Two square pads highlighted by the dashed circles in the inset image serve to check the quality of metal connections with silicon after soaking in acid solution for several hours. iii, The holes shown in the inset image are designed to expose the metal connections for bonding with external connective wires (e.g., ACF cables). iv, In the inset image the black dashed circle on the top indicates a metal loop that is used for checking connections after compressive buckling. The black dashed circle at the bottom are the wires connecting to the square silicon pad in (ii). v, PMMA holds the ten FETs together during the fabrication and gets removed during compressive buckling. (vi) The second PI layer has the same layout as the first one. vii, In this design, the middle hinge ($h_2$) is 20 μm wide. viii, The shape of the bonding site can be circular, square, or rectangular. A circular shape in this case makes the compressive strain more evenly distributed on the bonding area and prevents delamination of the device from the elastomer substrate.

FIG. 13 shows an optical microscopical images illustrating the fabrication steps of the arrayed FETs. a, The FETs have been doped by spin-on diffusants on the SOI wafer. b, The sensors are transfer-printed to a temporary substrate coated with PI (first/upper layer). c-g, Multi-layered polymers and metal are formed in steps of spin coating, sputtering, and photolithography on the temporary substrate. h, Finally, the multi-layered 2D device is transferred to the PDMS stamp. The scale bars on each panel, left: 200 μm, right: 50 μm.

Figure 14A:
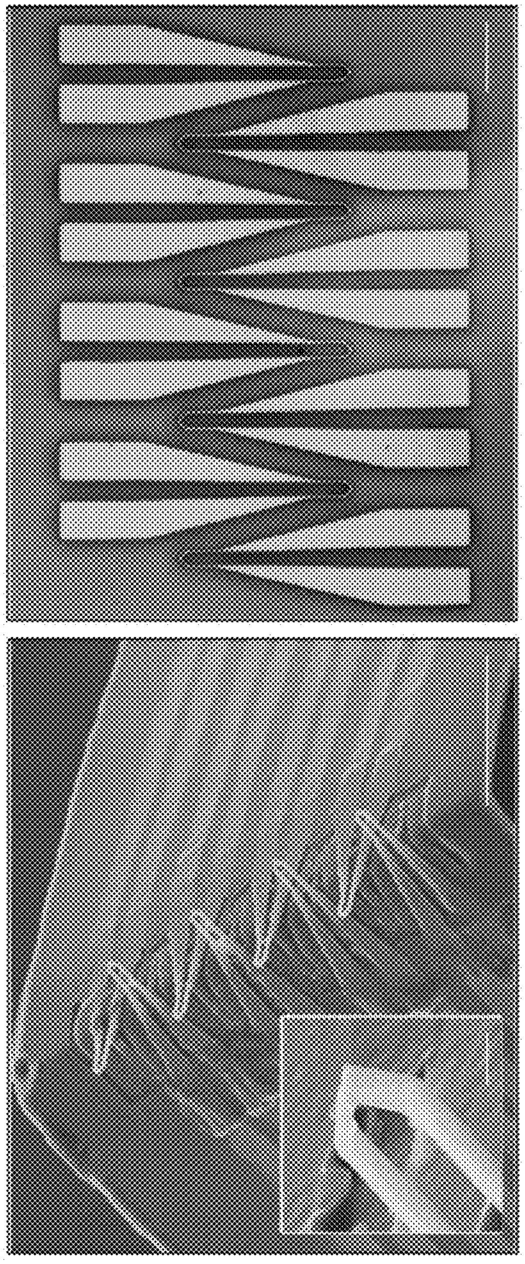
FIGS. 14A-14B show versatile designs of the FET shape.
Figure 14B:
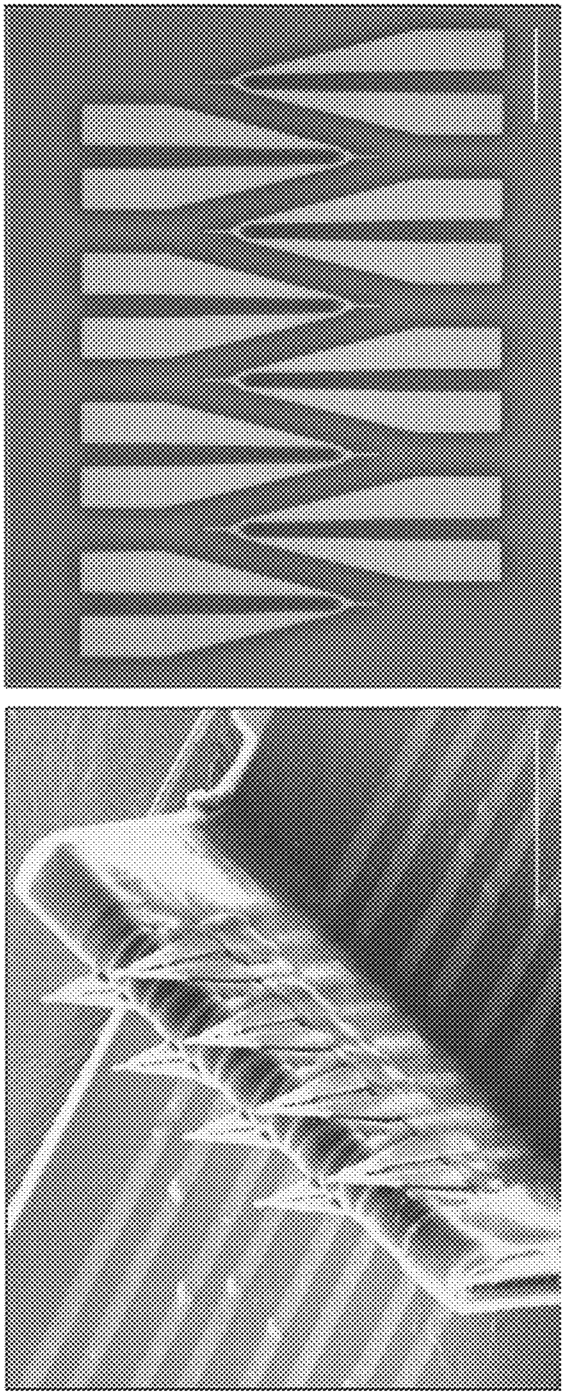

FIG. 14 shows versatile designs of the FET shape. Scanning electron and optical microscopical (SEM and OM) images of FETs of two representative structural designs. a, An SEM image of an eight-FET array after buckling (top) and an OM image of them in 2D (bottom). Each sensor has a kinked tip defined by e-beam lithography (inset). This structure is mimicking a reported nanowire probe with a similar kinked tip. The prestrain is only halfway released to enlarge the distance between the two rows of probes, thus covering a larger sensing area. b, An SEM image of an eight-FET array with sharp tips for minimal invasiveness to the cells (top) and an OM image of them in 2D (bottom). The FET's tip is 1 μm wide and 10 μm long. Scale bars: 50 μm in the top two SEM images; 2 μm in the inset image of (a); 20 μm in the bottom two OM images.

FIG. 15 shows experimental setup for recording cellular electrophysiology by the arrayed FETs. a, The setup includes a computer with an installed commercial program (Axon pCLAMP 10 Software Suite), which is used to control the other electronic equipment to acquire the analog signals and to display the converted digital data. The computer is connected with a DAQ that can convert digital to analog or analog to digital signals. One analog output (AO1) channel is connected to the source terminal of all arrayed FETs that share the same potential. Another analog output (AO2) channel is connected to the Ag/AgCl electrode. While performing the water-gate characterization, a potential sweep was applied on the Ag/AgCl electrode. In the cellular signal measurements, a zero potential was applied to that electrode to provide a reference potential of the extracellular medium. The DAQ has a total of 16 analog input (AI) channels. Each channel is connected to one output channel of the preamplifier. The preamplifier's inputs are connected to the drain terminals of the arrayed FETs. b, A schematic showing the experiment setup during the water-gate characterization of the FETs. On the Ag/AgCl electrode, a potential is swept from −100 mV to 100 mV. The solution used in this experiment is either PBS or Tyrode's solution. c, A schematic showing the experimental setup during cellular signal recording. A zero-gate potential is applied to the Ag/AgCl electrode during measurements. The solution is the extracellular medium of the specific cells being measured.

Figure 16B:
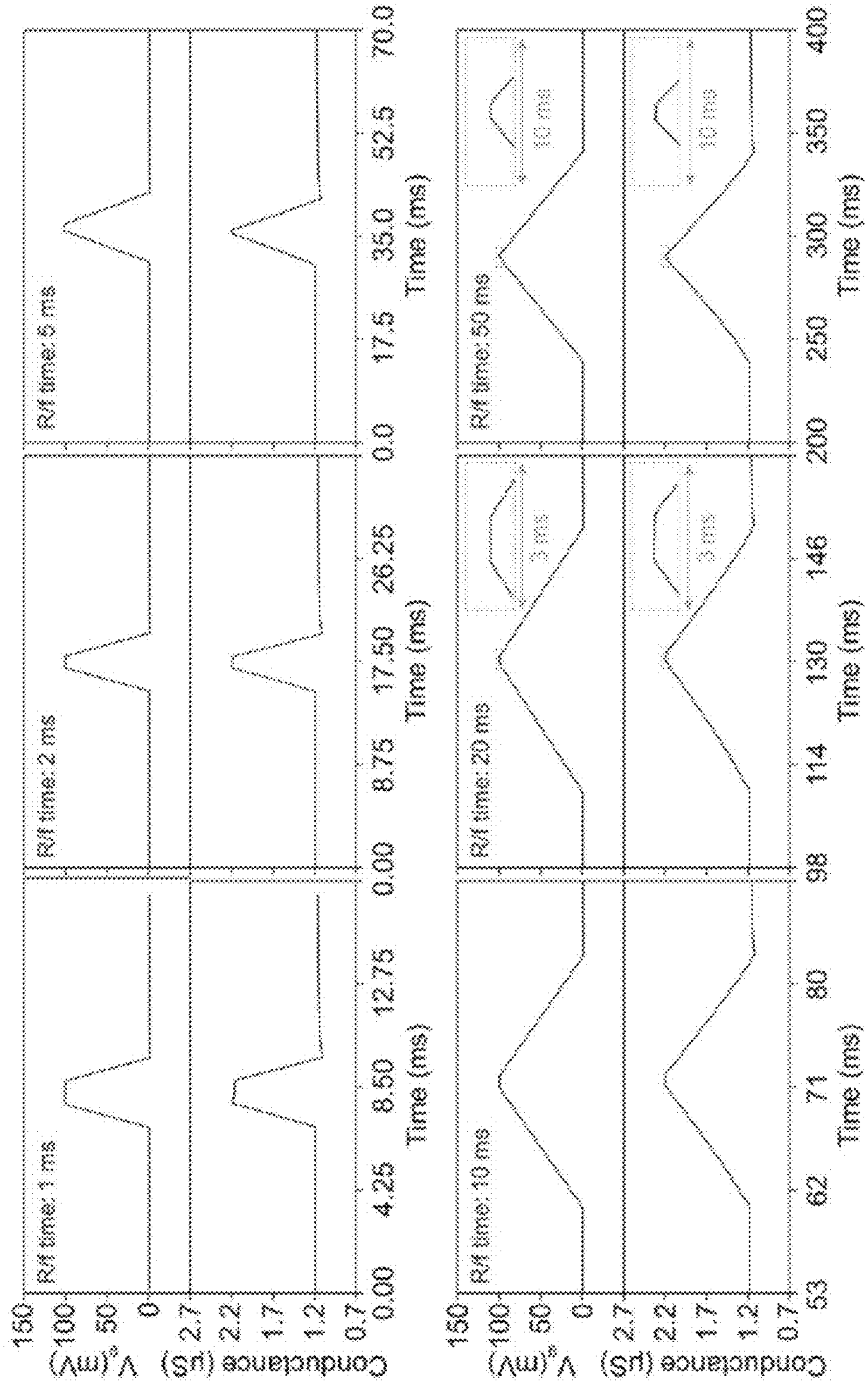

FIG. 16 shows the FET's response characteristics to rapid and slow signals. a, The FETs respond quickly to the rapid signal applied on its gate (rising/falling (R/f) time 5 ns, duration 0.1 ms, amplitude 100 mV, Model 3390, Keithley). The FETs' response time to the rapid signal is hundreds of nanoseconds (Rising: 712 ns; Falling: 618 ns), recorded at a 2 GHz sampling rate (PicoScope 6000) and analyzed in MATLAB. b, A 100 mV pulse (rising/falling time ranging from 1 ms to 50 ms, duration 1 ms) is applied on the gate by an Ag/AgCl electrode. The corresponding conductance of the FET remains the same trends to the input signals, which manifests its fast and stable response to various signals. The ionic solution-FET gate coupling is influenced by the ionic solution-metal electrode coupling in the water-gate measurement. The induced capacitance responds differently to various AC (fast and slow) inputs and slightly changes the FET's conductance. The induced capacitance can be safely ignored in cellular measurements due to the very localized membrane potentials to the FET gate. These results demonstrate the FET's fast response and large bandwidth for cellular measurements.

Figure 17A:
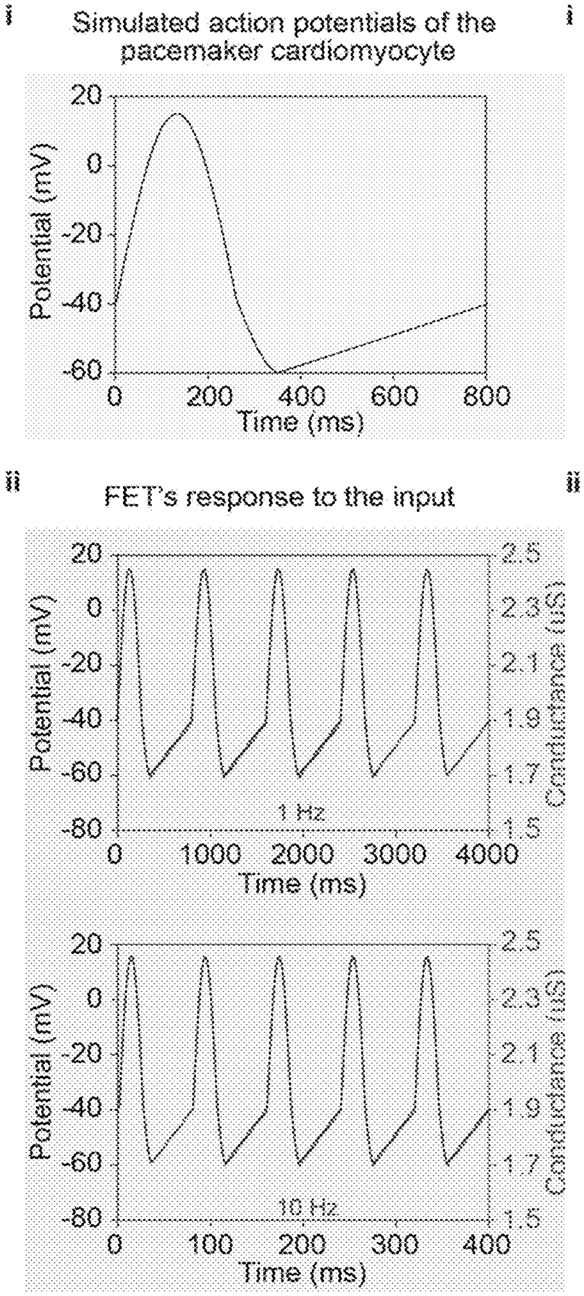
FIGS. 17A-17B show the FET's response to simulated cellular action potentials.
Figure 17B:
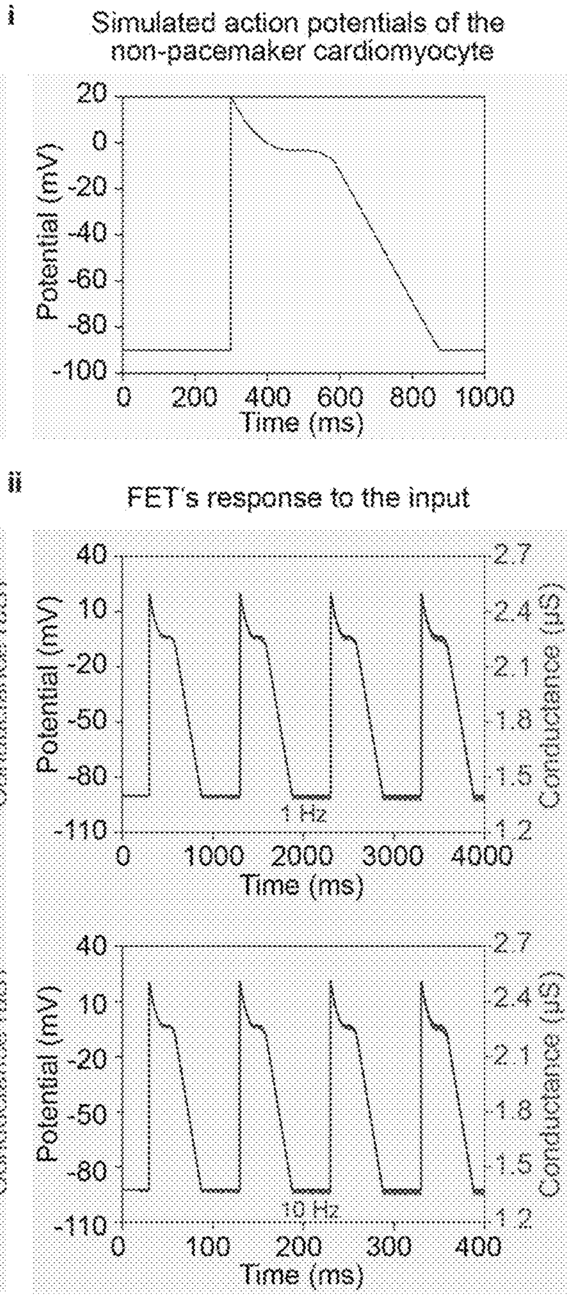

FIG. 17 shows the FET's response to simulated cellular action potentials. a,b, Simulated action potentials for (a) pacemaker and (b) non-pacemaker cardiomyocyte. Using the water-gate characterization setup and applying the simulated signals on the FET's gate at 1 Hz, and 10 Hz, corresponding to the action potential frequencies of various mammals' cardiomyocytes. Corresponding signals recorded by an FET are plotted in the same figures, with high fidelity to the original signals' morphologies at these frequencies.

FIG. 18 shows the schematic process of functionalizing the FET surface with phospholipids. To prepare the lipid solution, the phospholipids as received are dissolved in the chloroform solution. The chloroform needs to be removed entirely before the lipids get re-hydrated in DI water. The mixture in the aqueous solution then undergoes a freeze-and-thaw process for at least five times to break the multilamellar into unilamellar lipid vesicles. Later, sonication disperses the lipid vesicles in the solution and eliminates any aggregates of small lipid vesicles. The final step is to extrude the mixture solution through a PTFE syringe filter. Only the small unilamellar vesicles would be left in the solution. Then the lipid solution is applied on the FETs, which are put in an incubator at 37° C. for at least two hours. After that, removing excessive lipid solutions gently by DI water completes the functionalization. Note that the above processes only work for synthetic phospholipids. For natural cell membranes, they are naturally in a bilayer structure and vesicles. Therefore, only the extrusion step (f) is needed to produce small unilamellar vesicles.

FIG. 19 shows functionalization of the FET surface with phospholipids and equivalent circuit models of cellular measurements before and after FET internalization. a,b, Fluorescent images showing coatings of (a) natural phospholipids of red blood cell membranes and (b) synthetic phospholipid (DMPC) on the gate oxide of the FETs. These coatings promote the FETs' internalization into the cell body by spontaneous fusion of the phospholipids and the cell membrane. Scale bars: 100 μm. c,d, (c) A fluorescent image and (d) the corresponding transmitted optical image showing successful phospholipid coating on the 3D FETs. All FETs are coated by the phospholipids as shown by the intense fluorescence of the FET tips. Scale bars: 50 μm. e,f, Equivalent circuit models of a functionalized FET-cell interface for (e) extracellular and (f) intracellular interrogations of a cardiomyocyte. Before the phospholipids fuse, the FET sensor is extracellularly recording the membrane potential.

The circuit is composed of the FET resistance ($R_{FET}$), the FET gate oxide capacitance ($C_{ox}$), the spreading resistance due to the cleft between the cellular membrane and the FET surface ($R_s$), the cellular membrane capacitance ($C_m$), the cellular membrane resistance ($R_m$), the potential applied at the source terminal of the FET ($V_{source}$), the potential at the drain terminal ($V_{drain}$), the potential at the extracellular medium ($V_B$), and the potential in the middle of the conduction channel of the FET ($V_c$). $V_c$ doesn't represent the recorded potential of the cellular membrane. For an FET, the real cellular potential needs to be converted from the recorded conduction channel current and the transconductance of the FET calculated in the water-gate measurements. With closer proximity to the cell, the cell membrane spontaneously fuses with the phospholipid coating on the FET, realizing biological entrance of the FET and intracellular sensing of the transmembrane potential. These models were built based on widely adopted electrical models of cell membranes and FET. The extracellular signals are attenuated and distorted by the membrane impedance, showing a distinct shape to the intracellular signals.

FIG. 20 shows tests of cell viability. a,b, Confluent HL-1 cells (a) with and (b) without an FET device in the culture for two days. Fluorescent imaging results of live and dead cells show ~97% viability in these confluent cell cultures. c, Statistics of 8 cell cultures show that the FET has no cytotoxicity to the cells. d,e, Fluorescent imaging results of the same region of a confluent HL-1 cell culture (d) before and (c) after signal recording with 98.5% and 96.7% of cells alive, respectively. The FET shows little harm to the cells. f, Statistics of 3 cell cultures show that the recording process have negligible cytotoxicity to the cells. All scale bars: 200 μm.

Figure 21A:
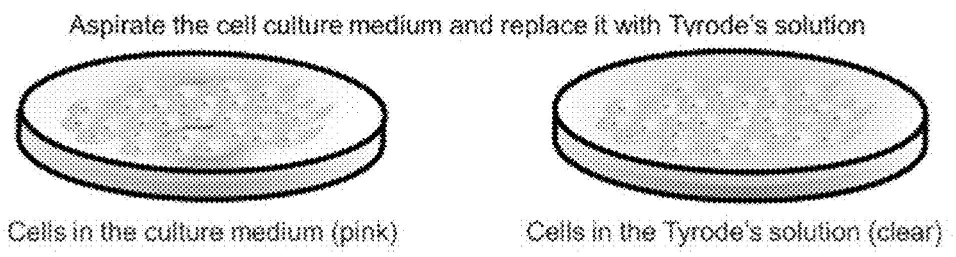
FIGS. 21A-21C show the schematic process of $Ca^{2+}$ sparks screening assay.
Figure 21B:
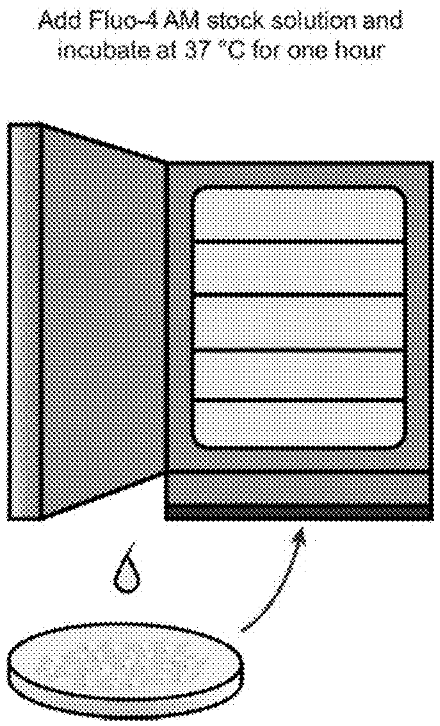
Figure 21C:
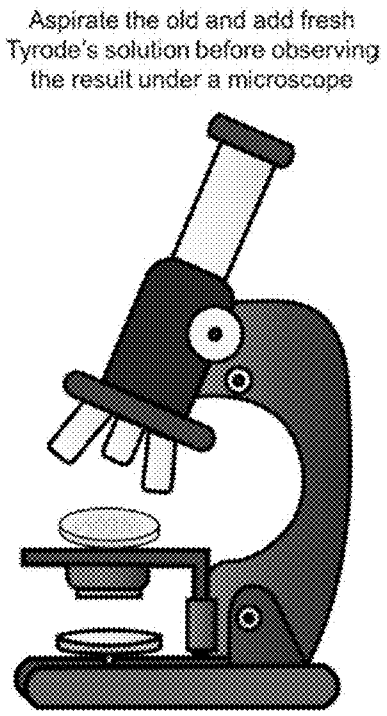
Figure 22B:
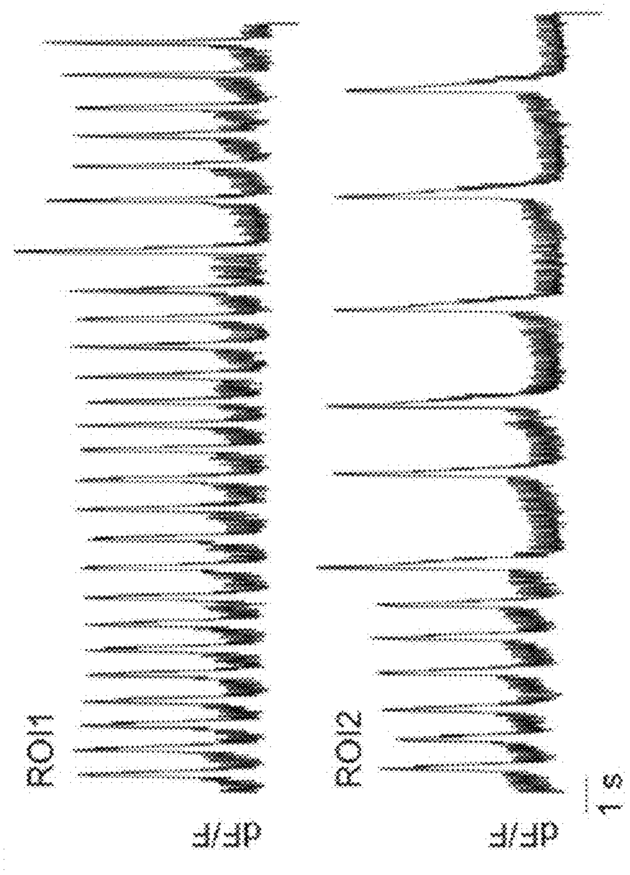
FIGS. 22A-22D show a $Ca^{2+}$ sparks assay illustrating HL-1 cells' action potentials and mapping field potentials in the whole cell culture.
Figure 22A:
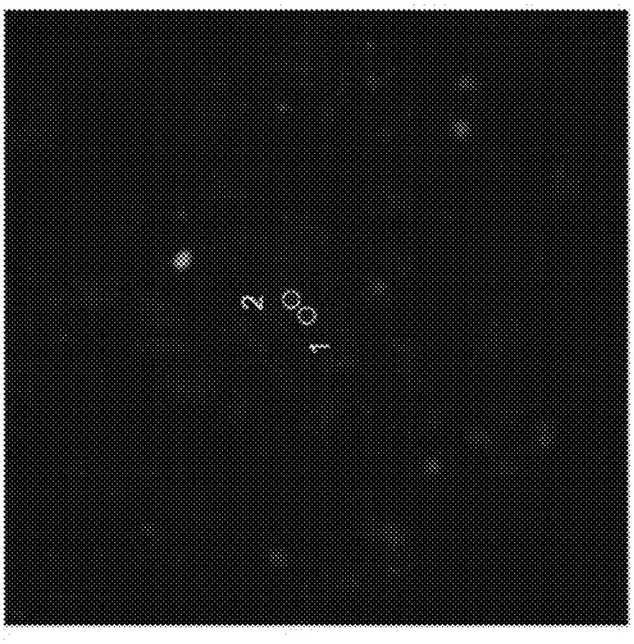
Figure 22C:
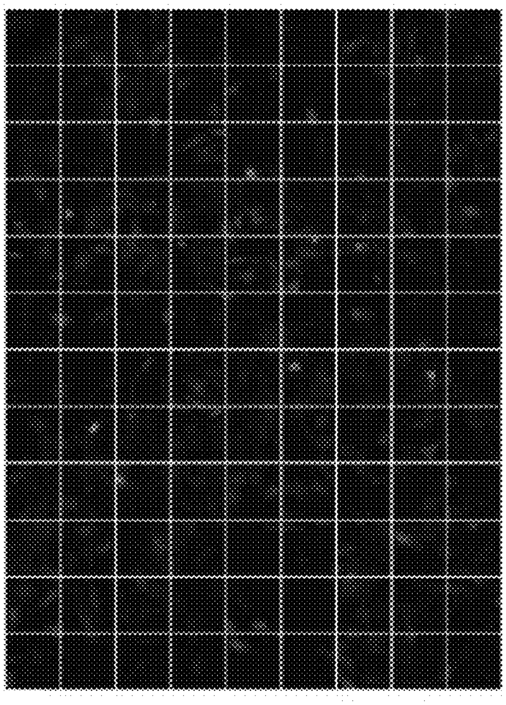
Figure 22D:
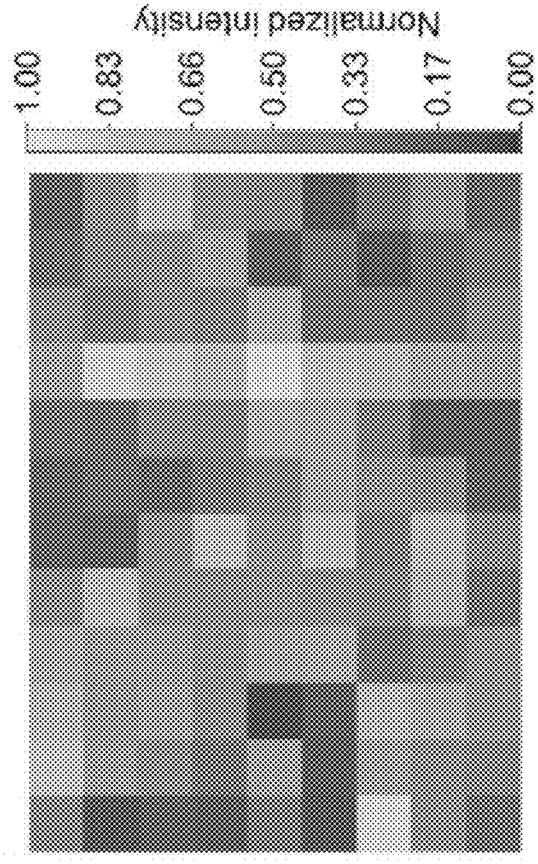

FIG. 21 shows the schematic process of $Ca^{2+}$ sparks screening assay. a, HL-1 cells are cultured in a petridish filled with the supplemented Claycomb medium. The medium is removed by aspiration and Tyrode's solution is added with $Ca^{2+}$ and glucose (pH: 7.35 at 37° C.). b, The Fluo-4 AM stock solution is added in the cells that are incubated for one hour. After that, the old solution is aspirated, and the fresh Tyrode's solution is added. c, Fluorescent $Ca^{2+}$ sparks can be immediately observed under a microscope.

FIG. 22 shows $Ca^{2+}$ sparks assay illustrating HL-1 cells' action potentials and mapping field potentials in the whole cell culture. a, A single snapshot from a video of an HL-1 cell culture stained with the Fluo-4 AM fluorescent dye. Two circles outline the two regions of interest (ROIs) to be analyzed, as marked by 1 and 2. b, Quantitative fluorescent intensity analysis of the ROI1 and ROI2 showing the transient $Ca^{2+}$ signals. Quantifications are performed on stacked snapshots extracted from the video, which would clearly illustrate the spiking rate and the signal conduction pathways in the whole 2D cell culture. Calculating the fluorescent intensities of ROI1 and ROI2 of every snapshot provides the digitized fluorescent intensity to render the plot. c, Mapping the fluorescent intensities of the whole observation region reveals the positions that are showing the $Ca^{2+}$ sparks at the corresponding time to that image. Quantification and replotting the fluorescent intensity amplify the intensity contrast for displaying the $Ca^{2+}$ distribution. Each snapshot is sectioned into 12 by 9 ROIs, and each ROI's average fluorescent intensity is digitized. d, A heatmap showing the quantified intensity results of the image in (c). The $Ca^{2+}$ sparks appear in yellow regions in color renditions of the heatmap (not shown).

FIG. 23 shows the schematic experimental setup of using the patch clamp to record intracellular signals of a single cell. The setup includes a computer that installs a commercial program (Axon pCLAMP 10 Software Suite), which is used to acquire, convert, and display the analog signals from the cells. The computer is connected with a DAQ that can realize digital to analog or analog to digital signals conversion. One of the DAQ's analog input channels is connected to a commercial preamplifier (Axopatch 200B). The preamplifier's input is linked to a headstage that can eliminate the system noise and stabilize the recorded signals from an Ag/AgCl electrode. The Ag/AgCl electrode is housed in a glass pipette of as small as a 1 μm in tip size. The pipette is filled with saline solution. The small pipette tip can clamp to a small patch of the cellular membrane. The whole-cell patch is performed when the cellular membrane at the patch gets ruptured and a giga-seal is formed between the pipette and cellular membrane.

Figure 24:
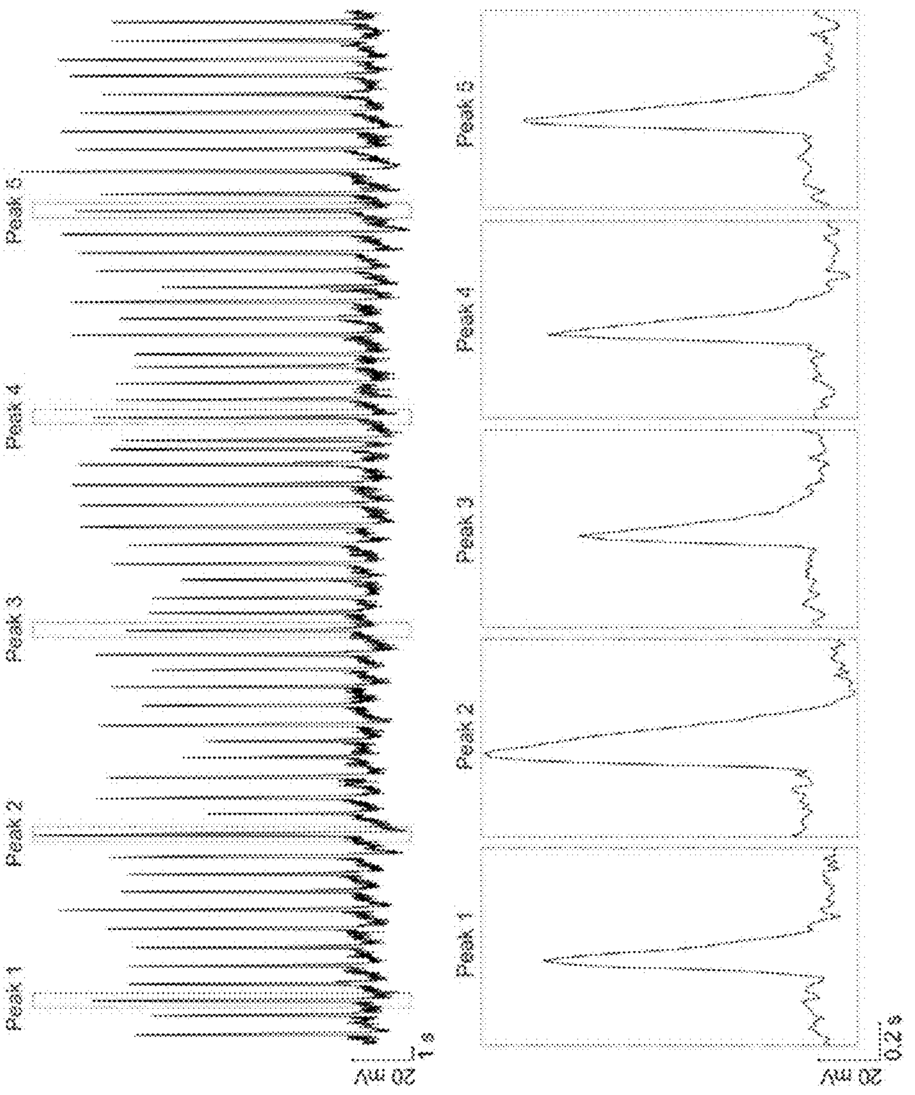
FIG. 24 shows extended intracellular recordings of an HL-1 cell.

FIG. 24 shows extended intracellular recordings of an HL-1 cell. Intracellular recordings of an HL-1 cell can maintain stable with periodic spikes for 71 seconds. The cells' activities are influenced by temperature, solution pH, and/or ion concentration disturbance during the measurement, which typically limit the possibility of long-time monitoring. What we demonstrate here is a considerably long duration among all reported active FETs for intracellular recordings.

Figure 25A:
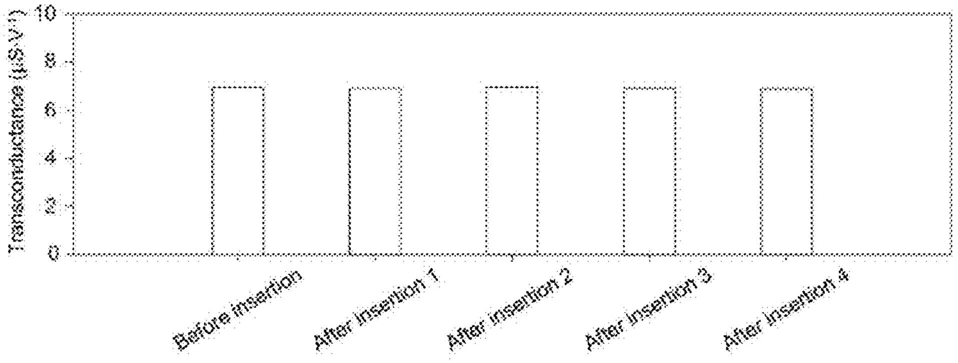
FIG. 25A-25B shows durability test of functionalized FETs for intracellular recording.
Figure 25B:
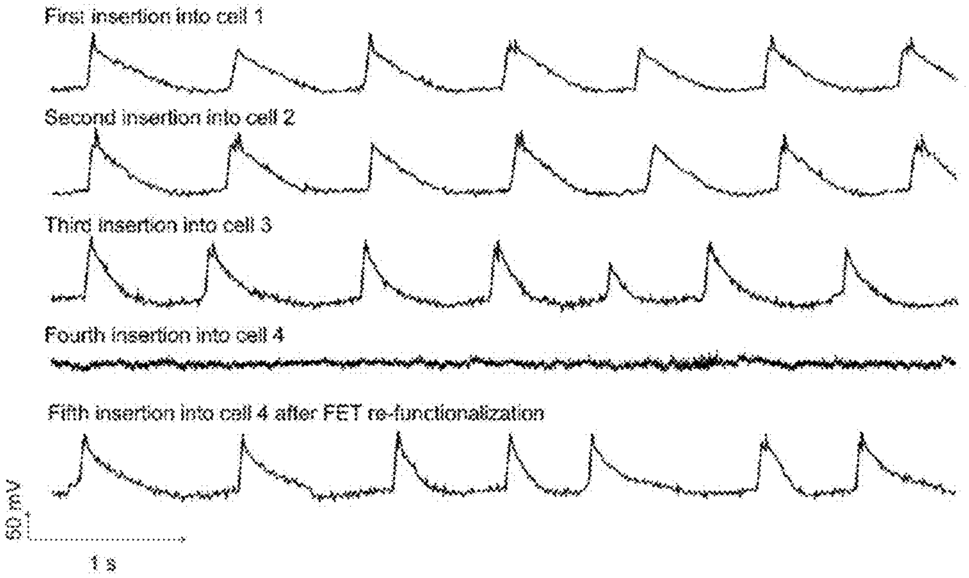

FIG. 25 shows durability test of functionalized FETs for intracellular recording. a, The FET's transconductance was measured before the first and after each cell insertion, showing its stability. b, Intracellular recordings of four different cells show that cell insertion becomes unsuccessful after three cell insertions. After re-functionalization of the same FET, intracellular action potentials were obtained from the fourth cell, which revealed that the failed intracellular recording in the fourth insertion was because of the damaged lipid bilayer on the FET surface.

Figure 26A:
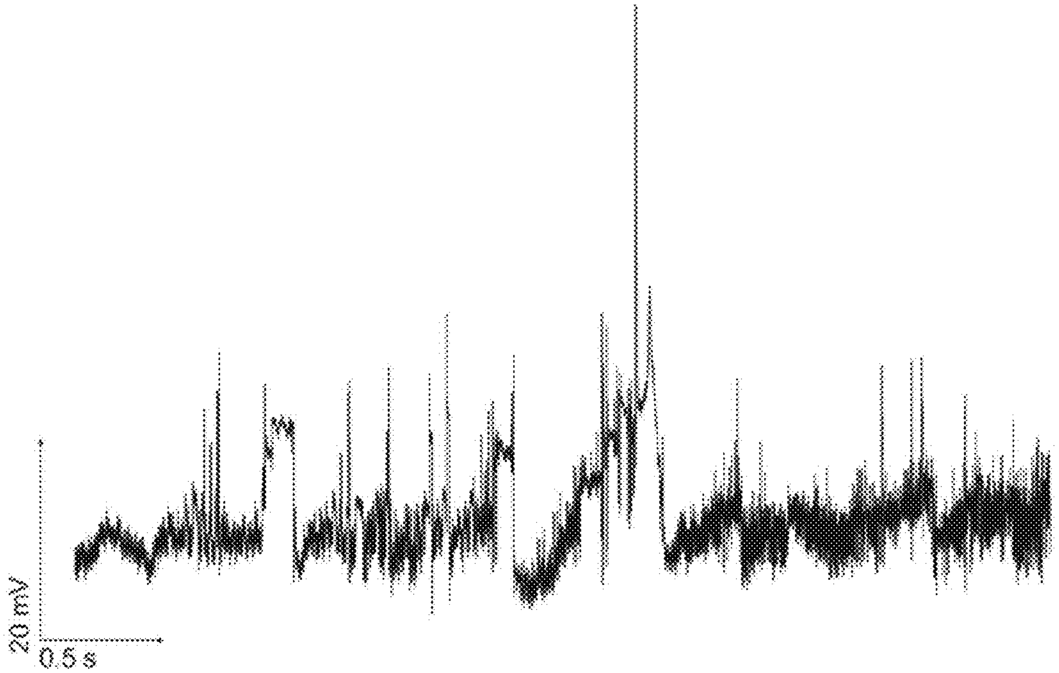
FIG. 26A-FIG. 26B shows recorded action potentials of adult mouse cardiomyocytes without phospholipids coatings.
Figure 26B:
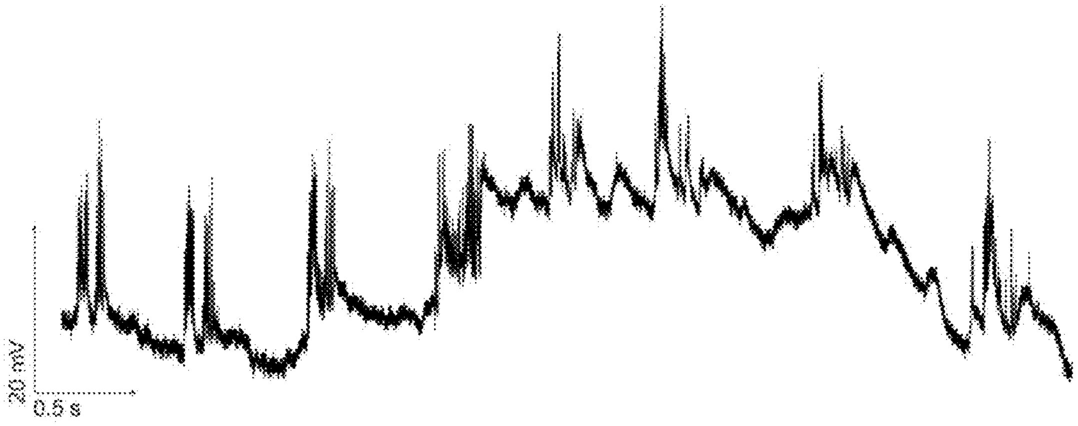

FIG. 26 shows recorded action potentials of adult mouse cardiomyocytes without phospholipids coatings. a,b, Two sweeps of intracellular signal recordings on adult mouse cardiomyocytes without lipid functionalization on the FET surface, with (a) considerable noise or (b) fluctuating baselines during the recordings due to the unstable FET-cell membrane interfaces.

Figure 27:
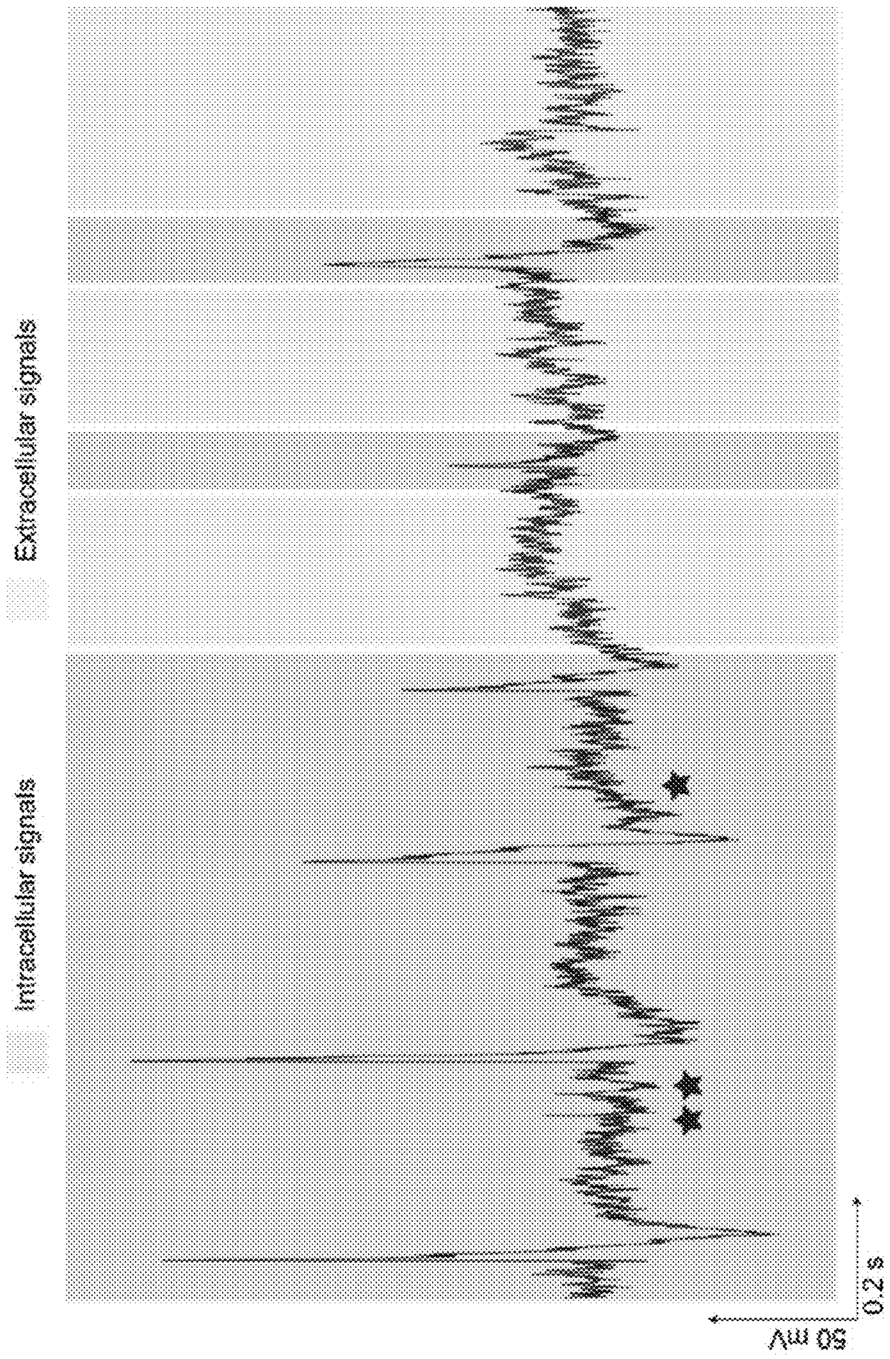
FIG. 27 show the process of transitioning from intracellular to extracellular recordings.

FIG. 27 shows the process of transitioning from intracellular to extracellular recordings. In this case, the intracellular recording of the HL-1 cell is achieved by mechanically rupturing the cell membrane. However, the sensor-cell interface is unstable. The cellular membrane will gradually fuse again and expel the FET. Thus, the signals sometimes show a transitioning process from intracellular (red shaded areas) to extracellular (light shaded areas) recordings. Intracellular subthreshold events are recorded as marked by the stars. These low-amplitude signals cannot stimulate the all-or-none action potentials but can reflect the membrane potential oscillations due to ionic activities across the cellular membrane. For instance, these subthreshold potentials can influence sodium ion channels (i.e., the h gate) to open or close, generating a refractory period when the action potentials cannot be triggered.

Figure 28A:
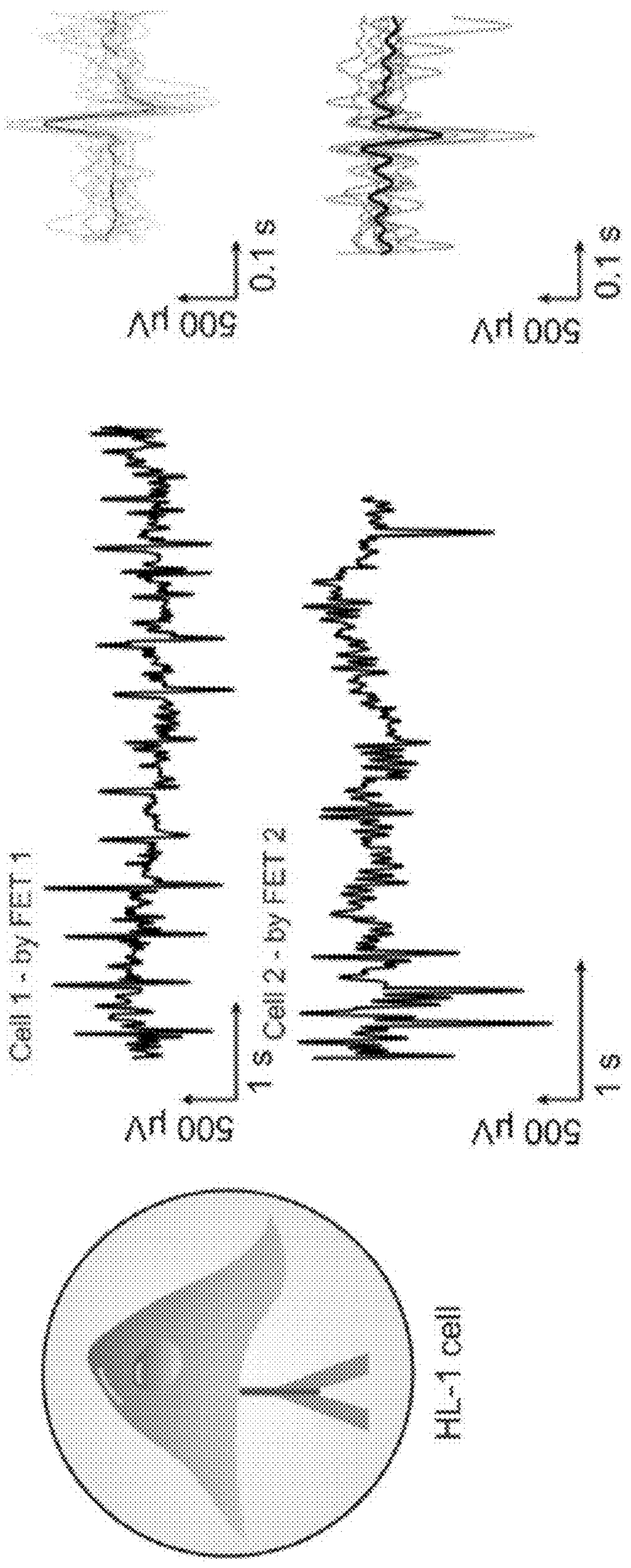
FIG. 28A-28C show extracellular field potentials of cardiomyocytes recorded by the FETs.
Figure 28B:
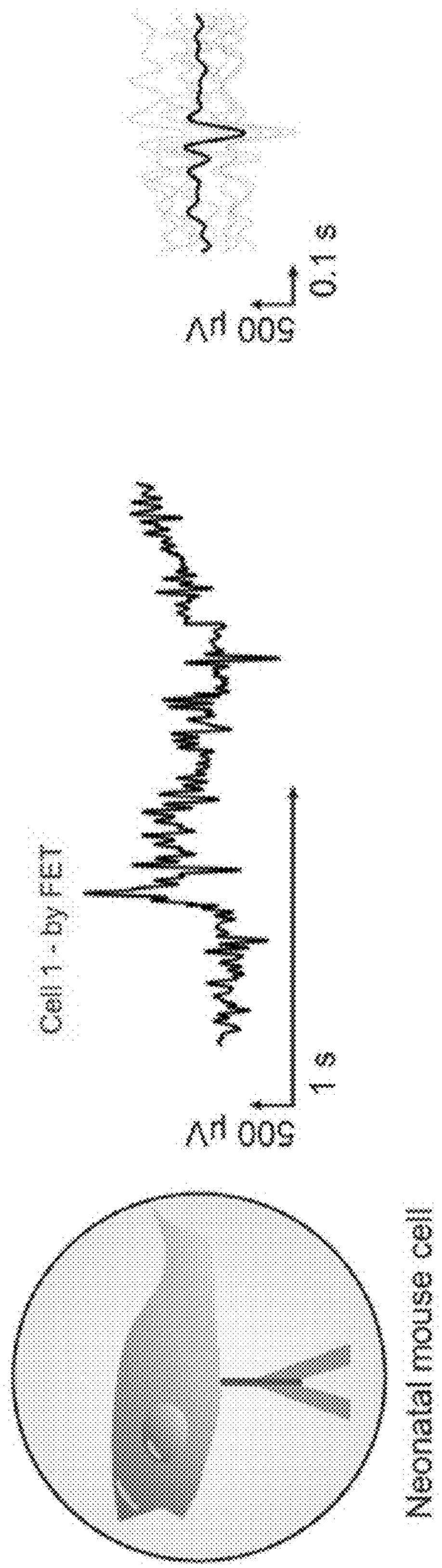
Figure 28C:
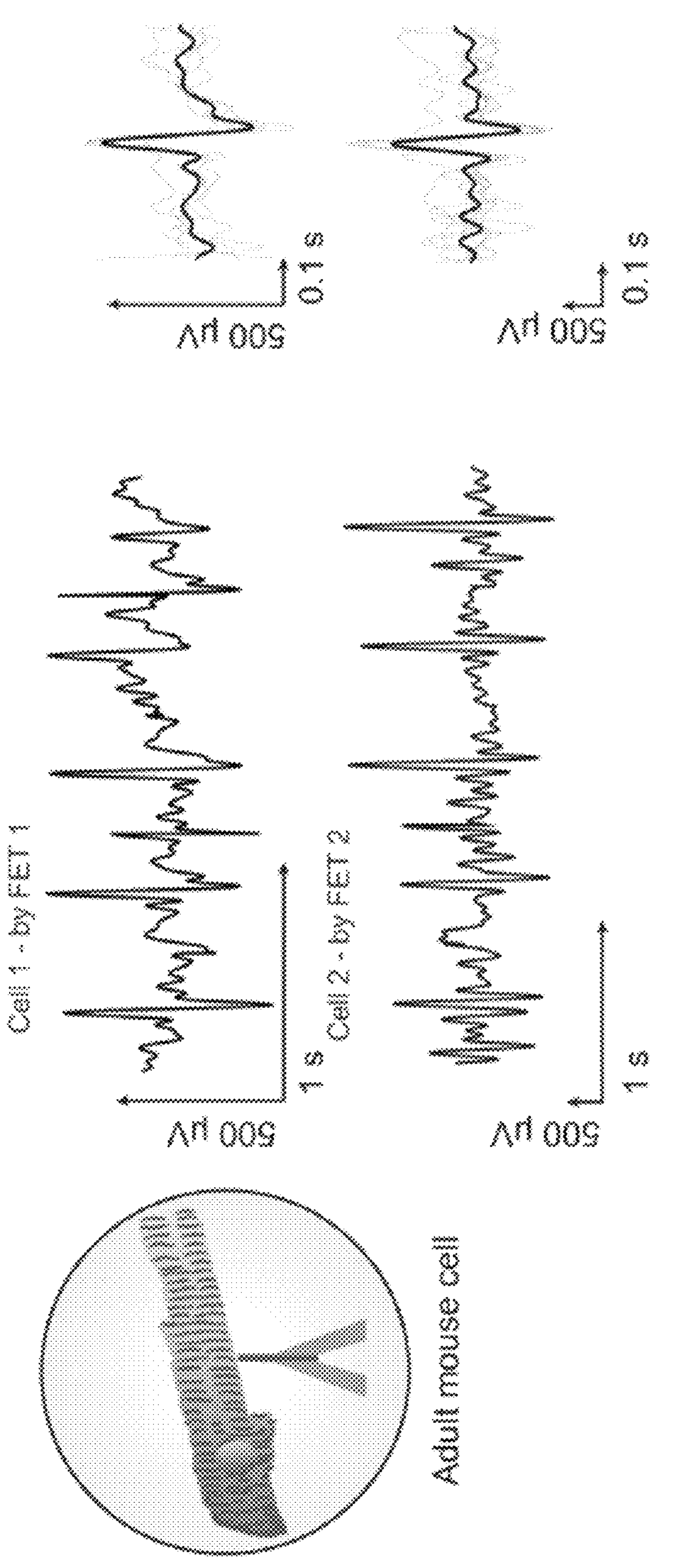

FIG. 28 shows extracellular field potentials of cardiomyocytes recorded by the FETs. a-c, Before penetrating the cell membranes, with close contact, the FETs can record periodic spikes from (a) the HL-1 cells and (b, c) primary cells. These low-amplitude extracellular signals are characteristic extracellular field potentials of the cardiomyocytes.

Figure 29B:
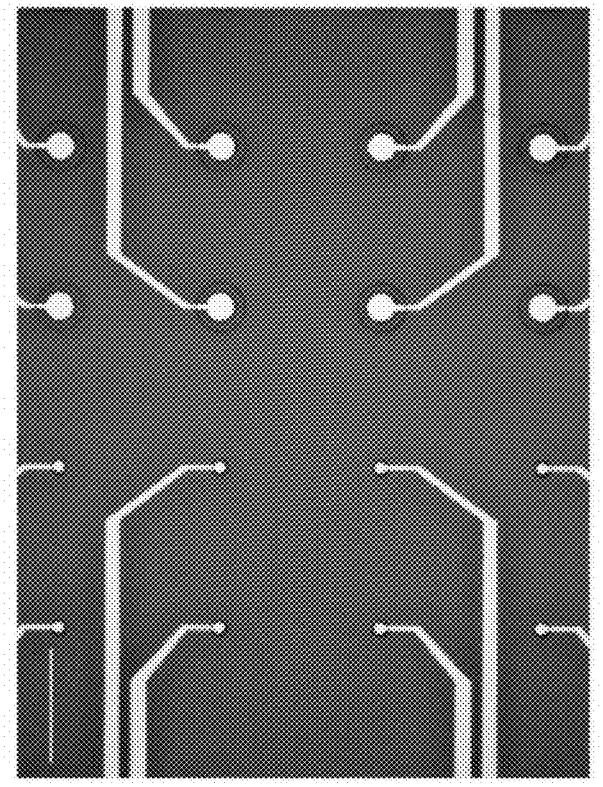
FIG. 29A-29C show extracellular field potentials of HL-1 cells recorded by the MEA.
Figure 29A:
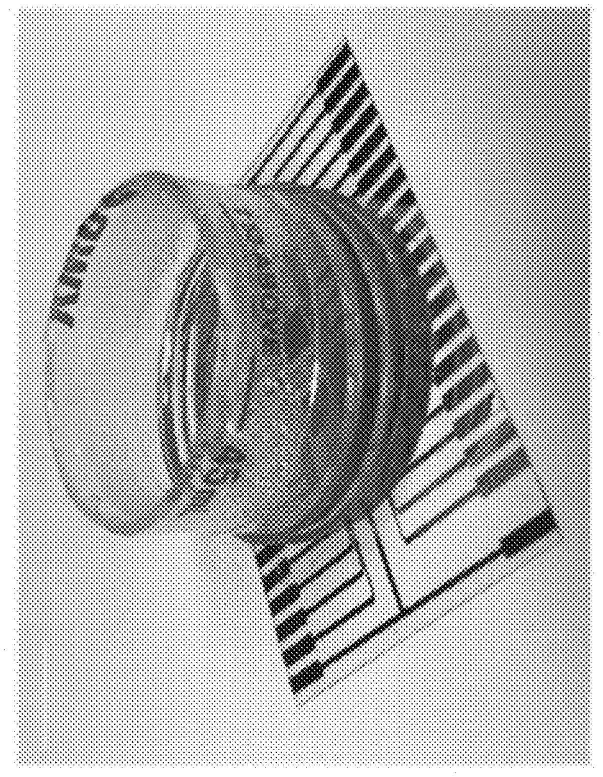
Figure 29C:
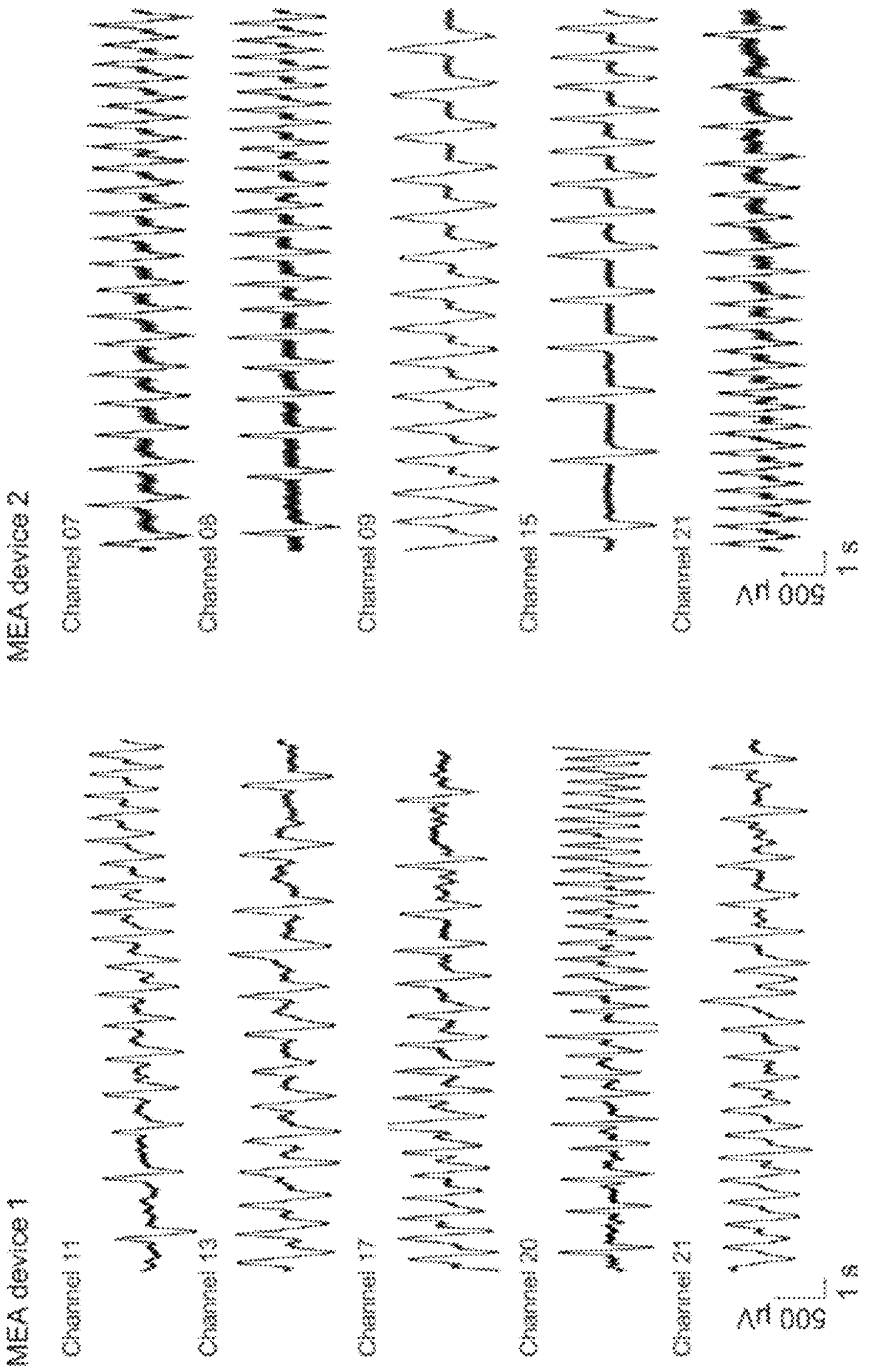

FIG. 29 shows extracellular field potentials of HL-1 cells recorded by the MEA. a, A picture of the MEA with a customized container filled with the Claycomb Medium for HL-1 cell growth. Cells are growing on the MEA surface inside the tube for 3-4 days in an incubator at 37° C., 5% $CO_2$ before they reach confluency. Scale bar: 10 mm. b, A closeup optical microscope image showing the metal pads and the covered connection wires by a layer of insulating SU-8. Only the circular areas of the metal pads are exposed to contact the cells. Scale bar: 200 μm. c, Representative extracellular field potentials of the HL-1 cells from two MEAs. The signals have been processed by a bandpass filter (0.5-30 Hz) in MATLAB.

FIG. 30 shows characterization of the electrical signal delay introduced by the measurement system. The same method as that used to characterize an FET's temporal response to dynamic signals is adopted to measure the delay between any two FETs in an array. A 100-mV pulse (rising/falling time of 0.01 ms, duration of 0.1 ms) is applied on a 10-FET array. The FETs' responses to the input pulse signal are simultaneously recorded at a 100 kHz sampling rate. a, Responses of the 10-FET array to the same input signal showing each FET is working independently. The dash lines mark the starting points of the rise and fall edges of the pulse. b, The cross-correlation method is used to calculate the latencies between any two channels showing that the system delay over the whole device is negligible. It proves that multiple FETs in an array exhibit the same characteristics to dynamic signals. Further, the system-induced electrical delay is negligible compared to those generated from cellular ionic dynamics.

Figure 31A:
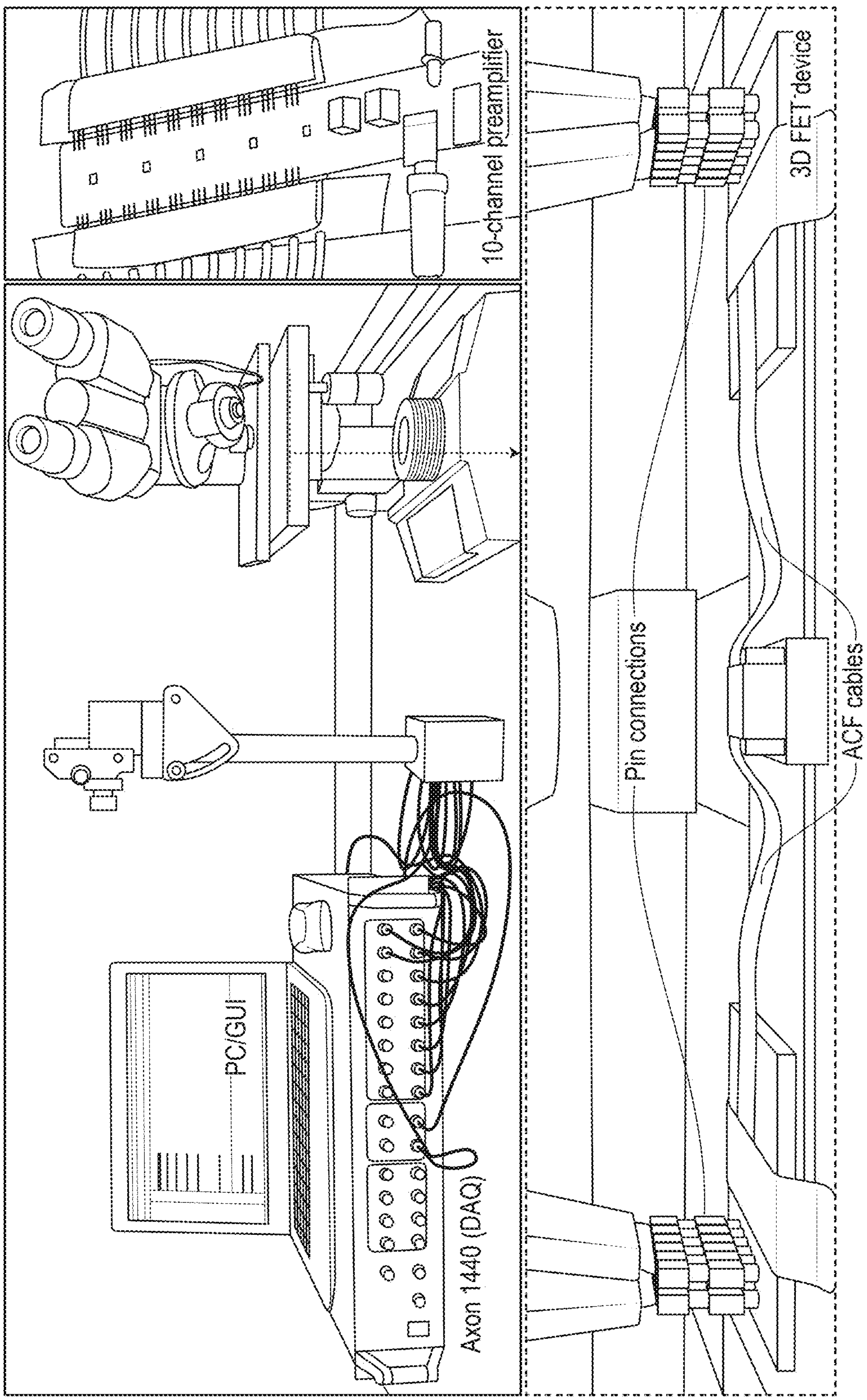
FIG. 31A-31B show pictures of the experimental setup for cellular electrophysiology recording using the arrayed FETs.
Figure 31B:
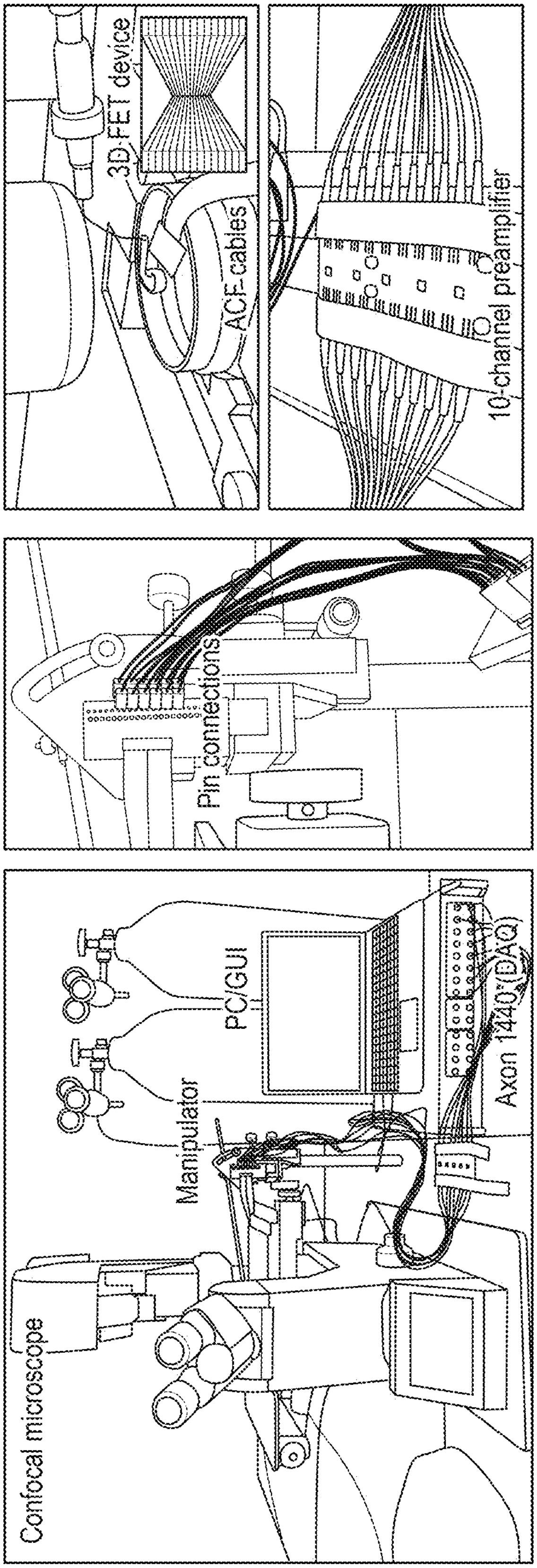

FIG. 31 shows pictures of the experimental setup for cellular electrophysiology recording using the arrayed FETs. a,b, Using an ACF cable, the FET array is connected to the amplifier, analog-to-digital converter (ADC), and PC sequentially, as shown in the schematics in FIG. 15*a*. During measurements, we can either place a sheet of PDMS (a) with cardiomyocytes on the FETs or fix the FET to a manipulator and approach to cell cultures in the dish (b). During signal recording, an Ag/AgCl electrode is inserted into the culturing solution to maintain the extracellular potential at zero bias.

Figure 32:
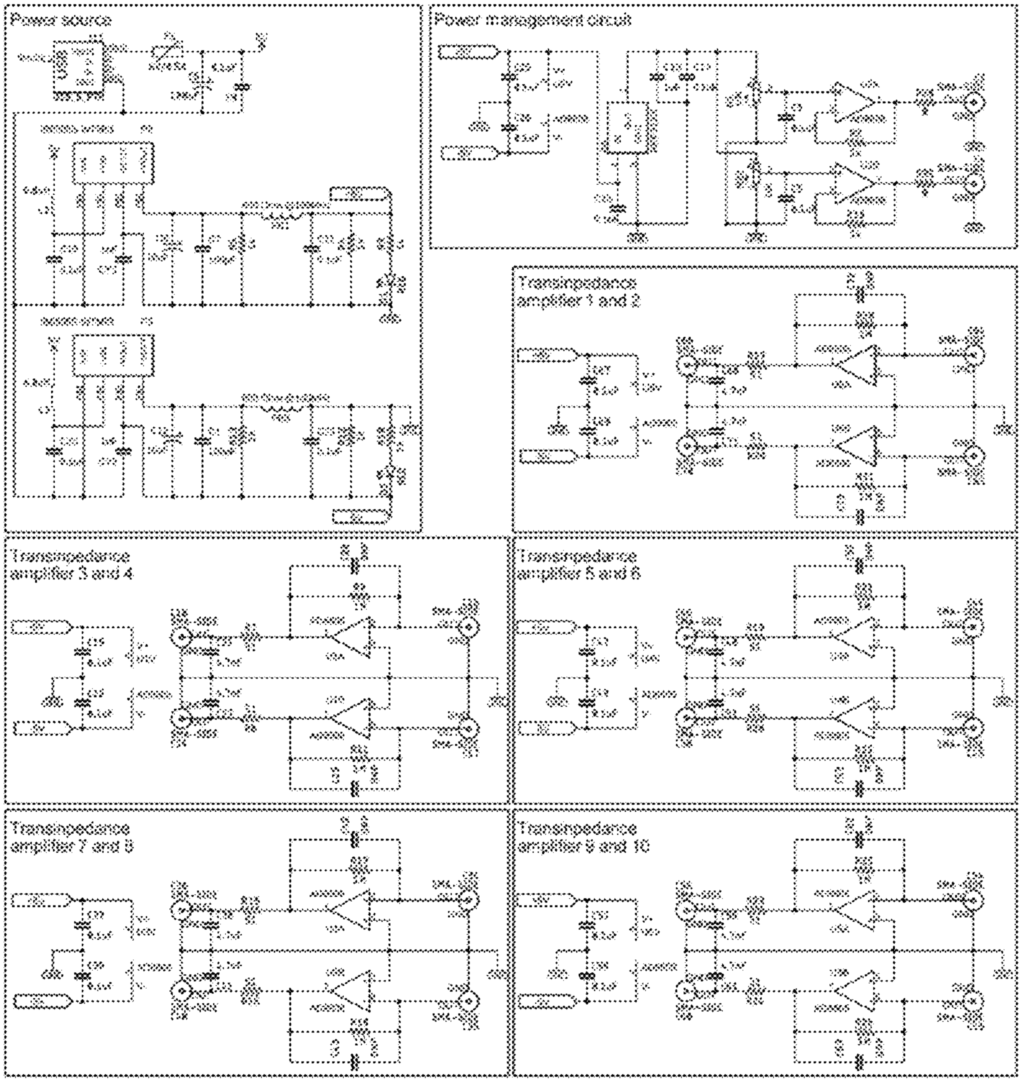
FIG. 32 shows the circuit design of the customized 10-channel current preamplifier.
Figure 33A:
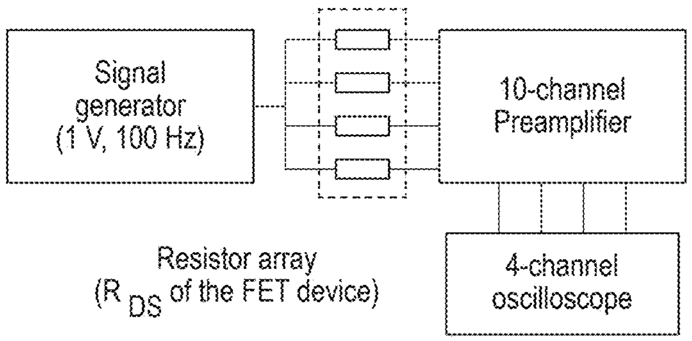
FIG. 33A-33D show electrical properties of the customized 10-channel current preamplifier.
Figure 33B:
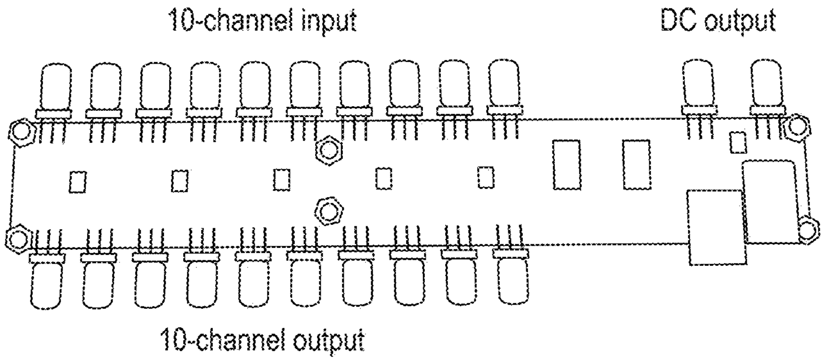
Figure 33C:
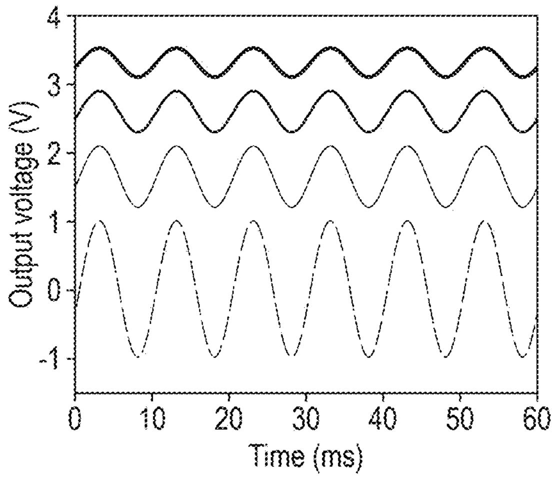
Figure 33D:
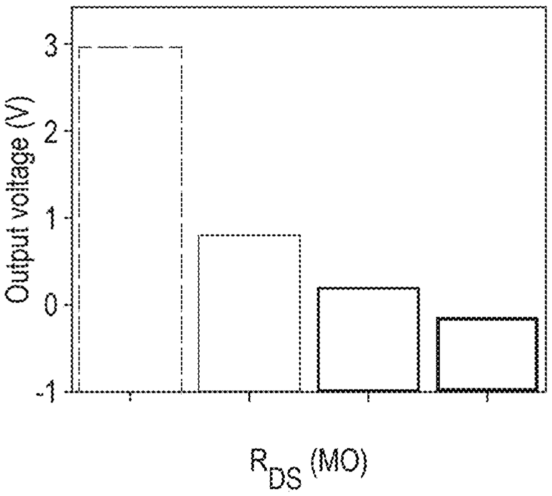

FIG. 32 shows the circuit design of the customized 10-channel current preamplifier. The current amplifier contains a USB power source and a power regulation circuit that can stably output +5 V and −5 V constant voltages to the entire circuit. A power management circuit is designed to stabilize the output voltage further to be +5 V or −5 V accurately. Also, it can regulate the output voltage to be in the range from 0 to 2 V. The amplifier circuit integrates ten independent transimpedance amplifier circuits that can function individually.

FIG. 33 shows electrical properties of the customized 10-channel current preamplifier. a, The electrical setup to characterize the multi-channel amplifier. A generated signal is exerted on four parallelly connected resistors. The other ends are input into four different channels of the preamplifier. An oscilloscope displays the amplified and digitalized signals. b, A picture of the customized 10-channel preamplifier, labeled with input and output terminals. Scale bar: 2 cm. c, The amplitude differences are from the different values of the four resistors. d, The amplitude of each output signal is different from each other, which demonstrates the four channels are functioning independently, with no crosstalk.

Figure 34A:
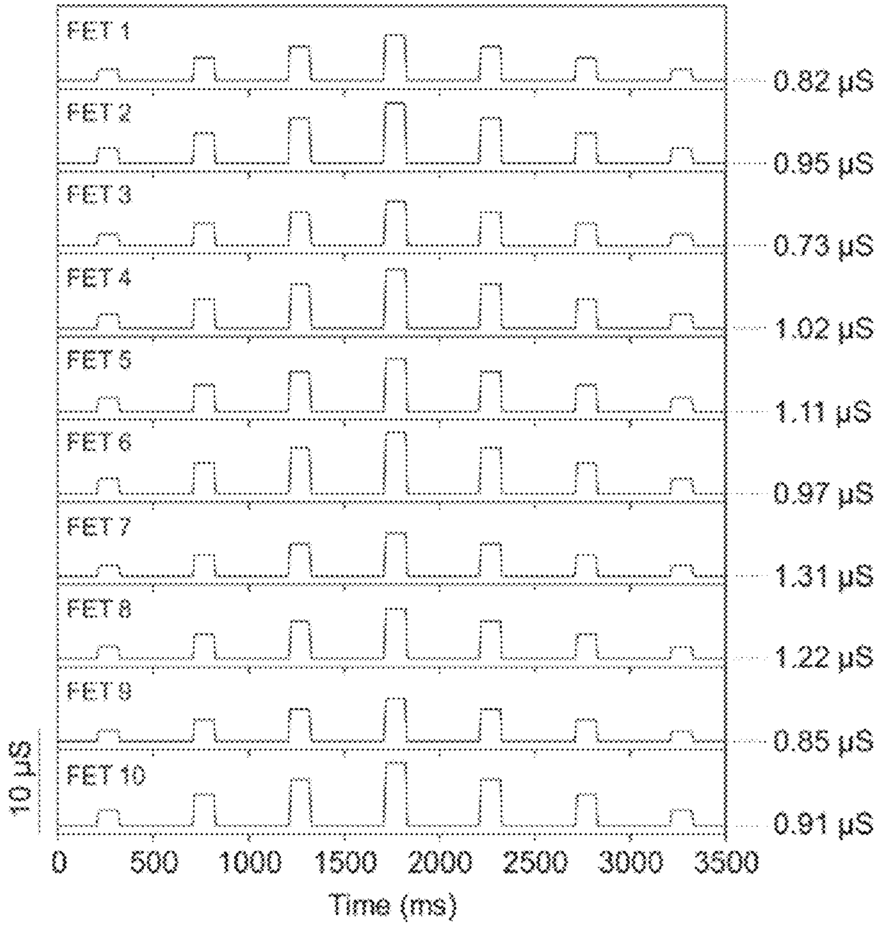
FIG. 34A-34B show data verifying the arrayed FET device's crosstalk.
Figure 34B:
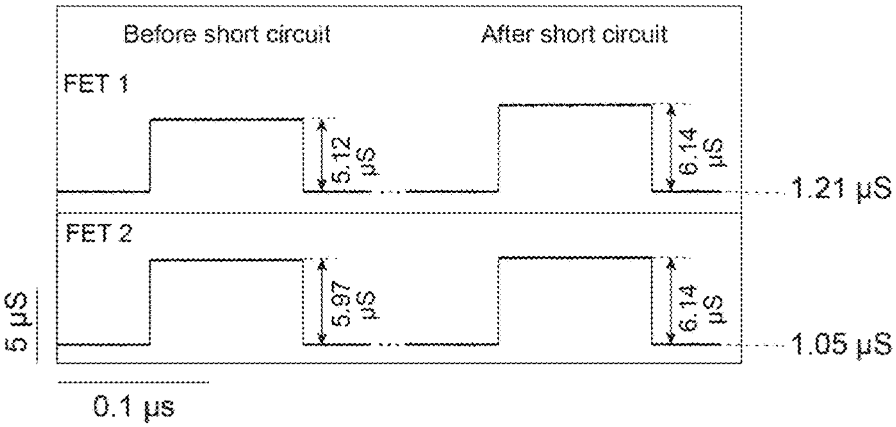

FIG. 34 shows data verifying the arrayed FET device's crosstalk. a, The same signal, containing seven pulses (from 100 mV to 400 mV and then back to 100 mV, with a step size of 100 mV, rising/falling time of 0.1 ms, duration of 100 ms), is applied to the gate solution of all 10 FETs. Each FET is separately connected to an individual channel of the preamplifier. The 10 responses recorded by the 10 FETs show different signal amplitudes, illustrating the variance of their sensitivities. The conductance of each FET under zero gate potential is shown in the far-right column. Each FET is recording signals independently, with no crosstalk during operation. b, When two FETs are shorted, their recordings become identical, which further proves that those small signal latencies are resulted from the cellular activities.

FIG. 35 shows recordings of spontaneous firing HL-1 cells by a 10-FET array. Cells communicate on the basis of intercellular electrical coupling by gap junctions, particularly ion channels. Ions (e.g., $K^+$) can travel from one cell to its neighboring cells via these gap junctions, triggering the donor cells' action potentials. Without pacing the cells (e.g., by a platinum stimulation electrode), the FETs can also form stable FET-cell interfaces and record action potentials from different cells. However, the action potentials show arrhythmic firing patterns, which mean the period of action potentials is varying. Also, the action potential's propagating behaviors become irregular because the locations and firing patterns of those spontaneously firing cells (i.e., pacemaker cells) in the culture are stochastic and inconsistent. Therefore, the signal conduction direction among these cells will alter according to the signals of the pacemaker cells.

Figure 10A:
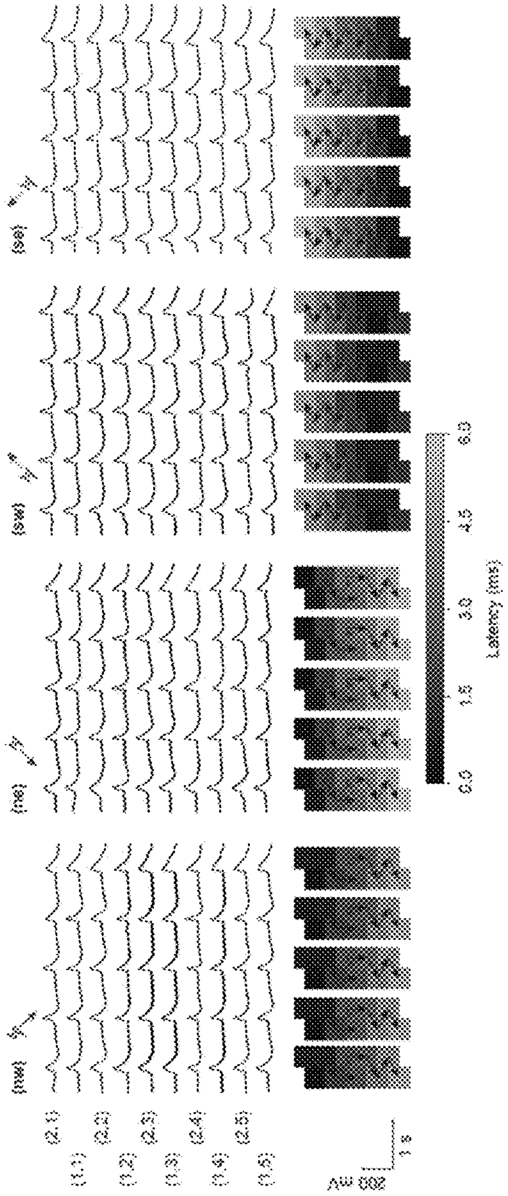
FIG. 10A-10B shows recordings of HL-1 cells' action potentials by a 10-FET array under electrical stimulation.
Figure 10B:
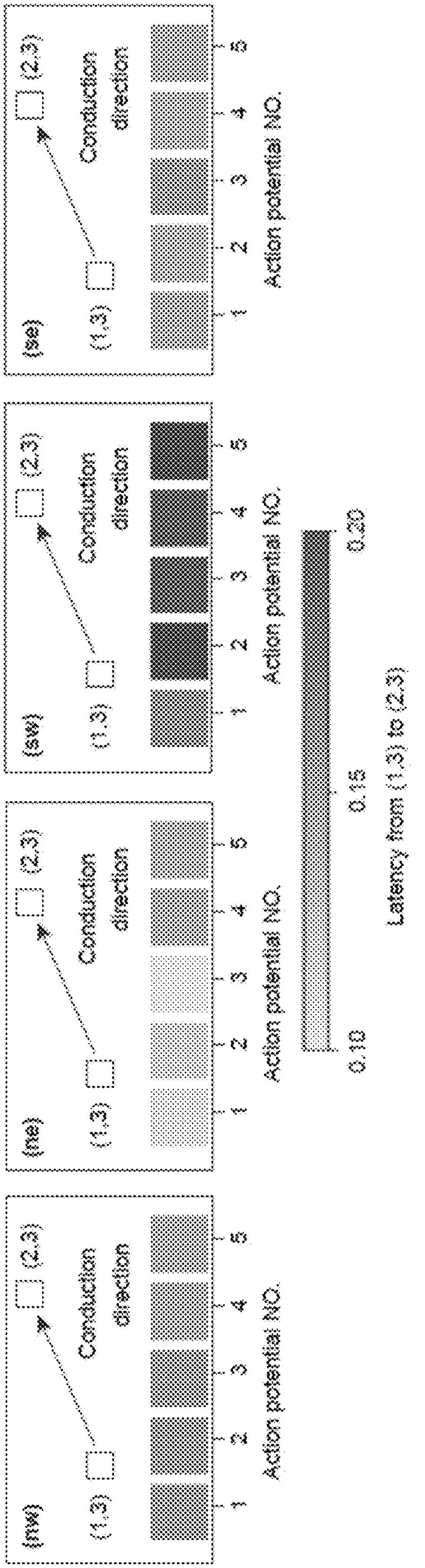

FIG. 36 shows the cross-correlation method. a, An example data set that is the same as those in FIG. 10*a*. b, We select the signals of (2,1) and (1,1) and section the data into five windows. Each window is one-second-long and includes one action potential spike. We choose the fifth pair of windows to conduct the cross-correlation and use the action potential spike as the reference point. Cross-correlation calculated in MATLAB in the right plot shows a −0.70 ms latency (t) from (1,1) to (2,1). By calculating the other four pairs of windows, we find the average latency from (1,1) to (2,1) is −0.68 ms. Similarly, latencies between any other two FETs can be accurately calculated, and the action potentials' propagating characteristics are faithfully revealed.

Figure 37:
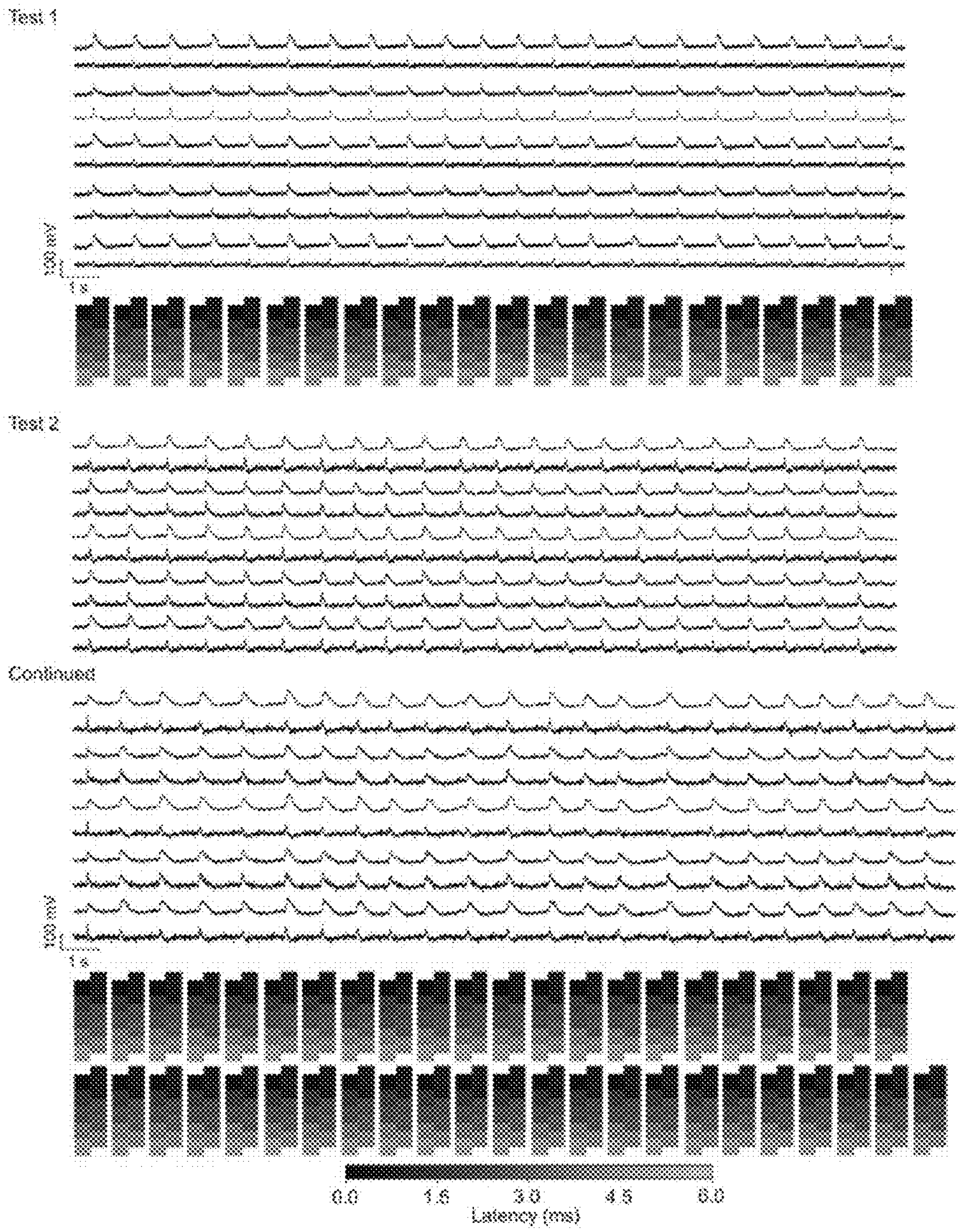
FIG. 37 shows long-period recordings of intracellular signals of paced HL-1 cells by the 10-FET array.

FIG. 37 shows long-period recordings of intracellular signals of paced HL-1 cells by the 10-FET array. The stimulation electrode is ~10 mm to the northwest corner of the FET array. Heatmaps elucidate the action potentials' latencies and the occurrence sequence among the cells. Signals of tests 1 and 2 show continuous recordings for 25 and 50 seconds, respectively, which is the longest among all arrayed FET-based intracellular probes in the literature. The extended intracellular recordings prove the stable performance of each one of the FETs in the array.

FIG. 38 shows justification of the intracellular signal conduction inside a HL-1 cell. a,b, Comparable conductance and transconductances of the 10-FET array measured before and after intracellular recordings, showing that the FETs maintain their intact electrical properties and are free from any crosstalk or short circuits between the FETs. The same FET array is used for the recordings in FIG. 4*d* and FIG. 10. c,d, With the same electrical stimulation (nw) as that in FIG. 10, another recording by the same FET array on a different HL-1 cell culture showing a ~0.18 ms latency between FETs (1,1) and (1,2), which are 35 μm apart. The intracellular signal conduction velocity is ~194 $\mu m \cdot ms^{-1}$ that is close to the measurements (~182 $\mu m \cdot ms^{-1}$) in FIG. 10. Such reproducible and reliable results provide additional evidence for the intracellular signal conductions. e,f, Studying the relationship between intracellular and intercellular signal conduction directions on another recording on HL-1 cell culture. In this case, the intracellular conduction direction from (2,4) to (1,4) varies with the intercellular direction when the stimulation orientation is changed from the north to the south of the FETs. The intracellular signal conduction velocity is ~191 $\mu m \cdot ms^{-1}$, which is on par with the results in other measurements.

FIG. 39 shows fluorescent images and simultaneous action electrical recordings of an FET array and HL-1 cells. The cells and FETs are prepared according to the staining protocol introduced in a, Fluorescent images of nuclei (NucBlue), cell membranes (CellBrite), and FETs (Rhodamine 6G), as well as a bright field optical image, illustrating features of the cells and FETs. Scale bars: 100 μm. b, A 3D view image corresponding to the images in FIG. 4*f*, showing the FETs structures and relative spatial locations. Scale bar: 50 μm. c, Cross-sectional images of each FET in the x-z and y-z planes, showing well-defined interfaces between the cells and FETs. d,e, Simultaneous electrical recordings performed with the fluorescent confocal imaging. The intracellular conduction direction is from (1,5) to (2,5). The intracellular signal conduction velocity is ~184 $\mu m \cdot ms^{-1}$.

Figure 40:
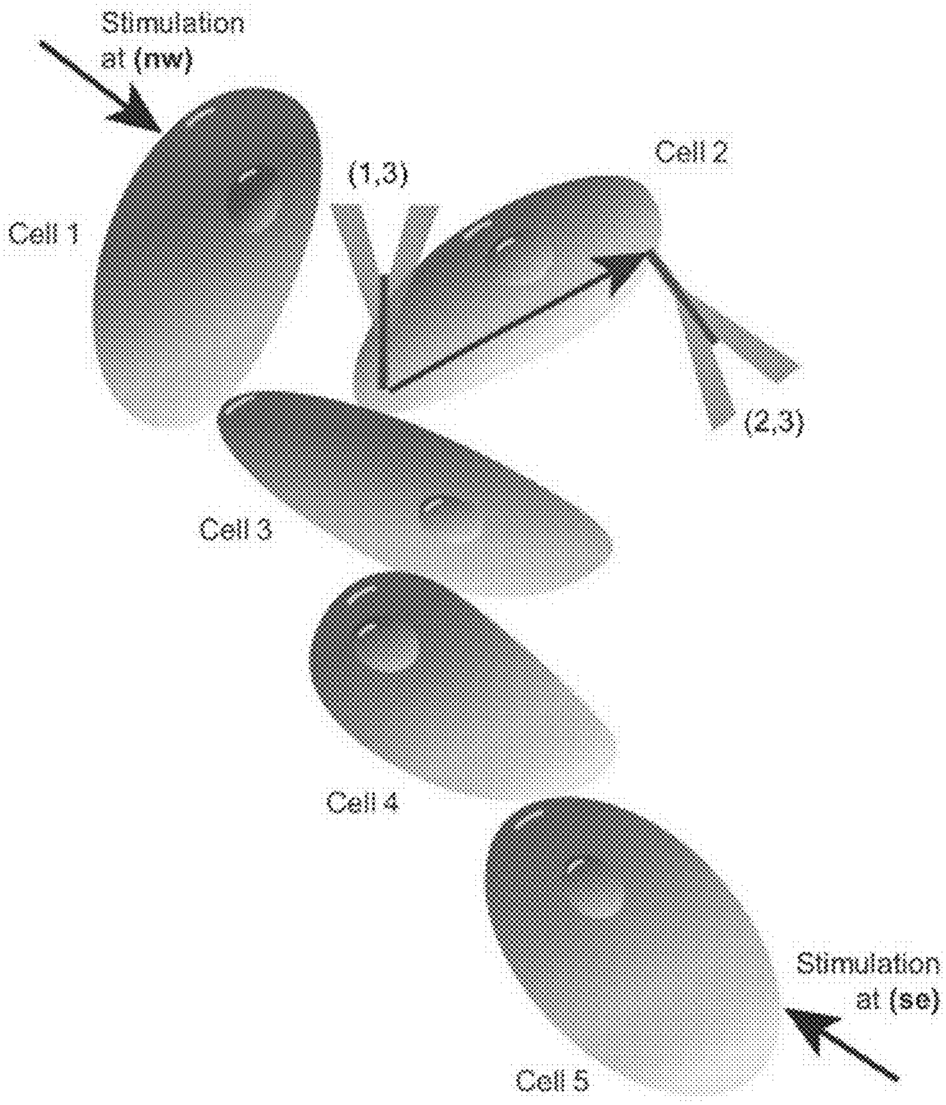
FIG. 40 shows a simplified model illustrating the independence of inter- and intra-cellular signal conduction directions.

FIG. 40 shows a simplified model illustrating the independence of inter- and intra-cellular signal conduction directions. Five cells are electrically coupled with each other at the contacted areas. Two FETs record intracellular signals simultaneously from Cell 2. Particularly, Cell 2 is only electrically coupled with Cell 3. When the stimulation is placed at the northwest (nw) orientation to the FETs, the intercellular signal propagates from Cell 1 and travels to Cell 3 and Cell 2. The intracellular conduction direction is from (1,3) to (2,3), because (1,3) is closer than (2,3) to the electrical coupling position between Cell 2 and Cell 3. When the stimulation is placed at the southeast (se) corner, the intercellular signal propagates from Cell 5 to Cell 4, Cell 3, and then Cell 2. Similarly, the intracellular signal conduction is still from (1,3) to (2,3) due to the same reason. In other words, the incoming signal from the upstream cell always first arrives at a location closer to (1,3) than (2,3), leading to an invariant intracellular signal conduction direction regardless of the intercellular signal conduction directions. In this case, the intracellular signal conduction direction is dependent on cells' coupling positions and FETs' sensing locations on the cell membranes.

FIG. 41 shows organization of the 128-FET array and display of data. a, Schematic distribution of the 128-FET array in eight arms of different directions, labeled counterclockwise from A to H. In each arm, the FETs have different heights distributed in three loops, labeled as 1, 2, and 3. b, A raster plot with coordinates of each FET in the array, whose data are in FIG. 5*b*. c, Heatmaps with the raster layout in (b) showing the normalized amplitude of each FET at specific time points, e.g., $t_1$, $t_2$, etc. The transient information of each FET's recordings could be animated by stacking many heatmaps of sequential time points.

FIG. 42 shows pictures of the experimental setup of recording electrophysiology of the 3D cardiac tissue by the 128-FET array. a, The measurement setup includes a 128-FET array connected to a flexible print circuit (FPC, uxcell) with flexible ACF cables, a customized DAQ board (Texas Instruments DDC264), and a GUI (provided by Texas Instruments). b, A closeup of the 128-FET array interfacing a 3D cardiac tissue. Signals transmit from the front-end sensors to the DAQ board via jumper wires. c, The 128-FET array fans out to the external circuits via flexible ACF cables. d, The DDC264 evaluation software is the interface used to command the DAQ board for data acquisition and storage.

Figure 43B:
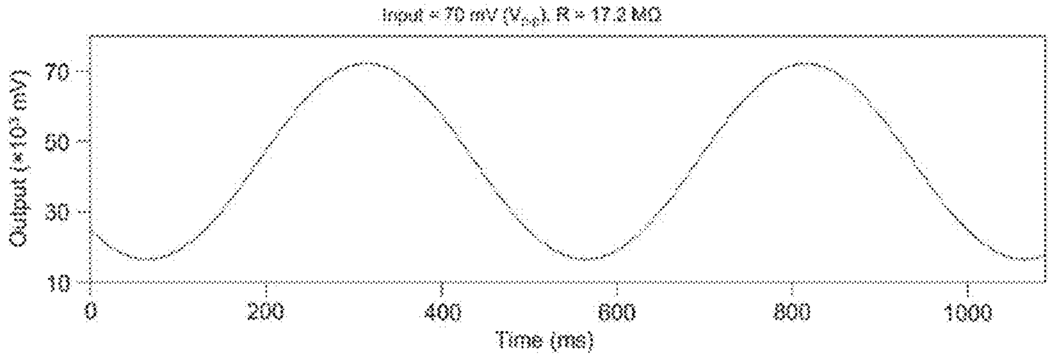
Figure 43C:
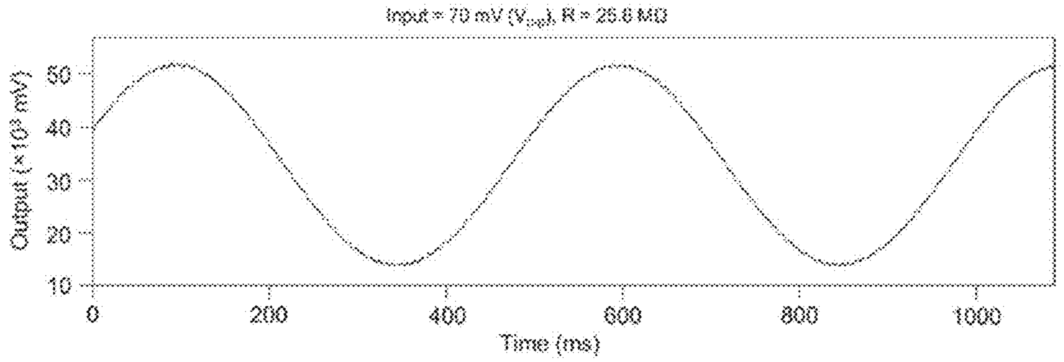
Figure 44B:
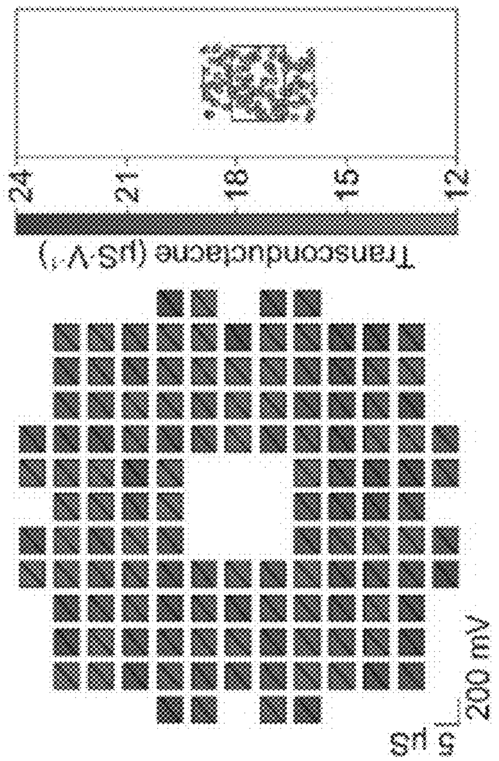
FIG. 44A-44D show electrical characterizations of the 128-FET array.
Figure 44A:
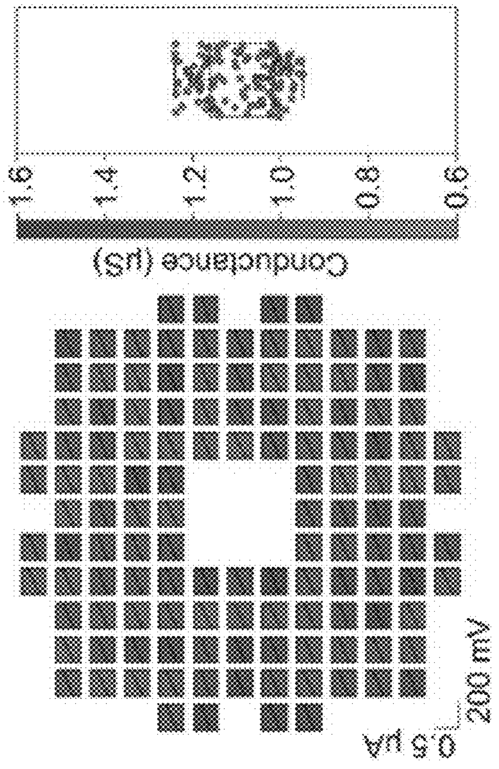
Figure 44C:
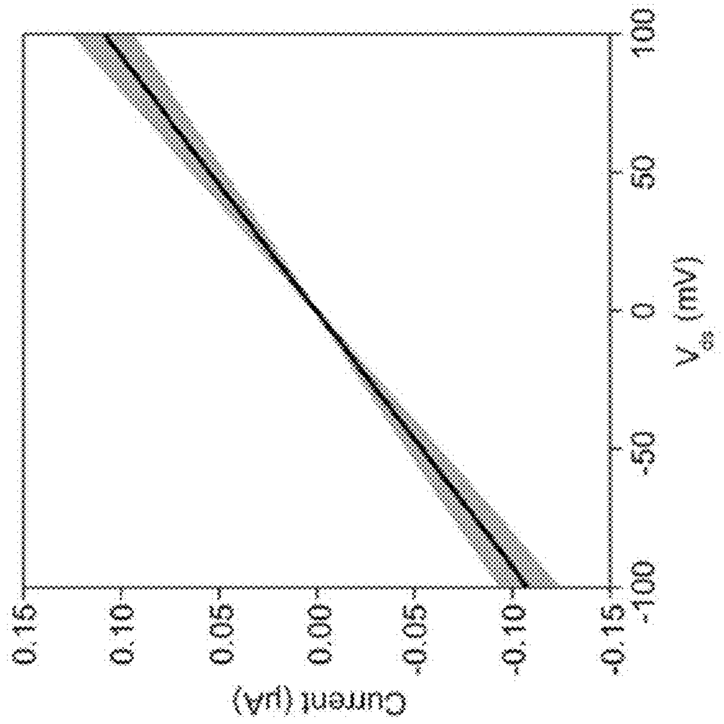
Figure 44D:
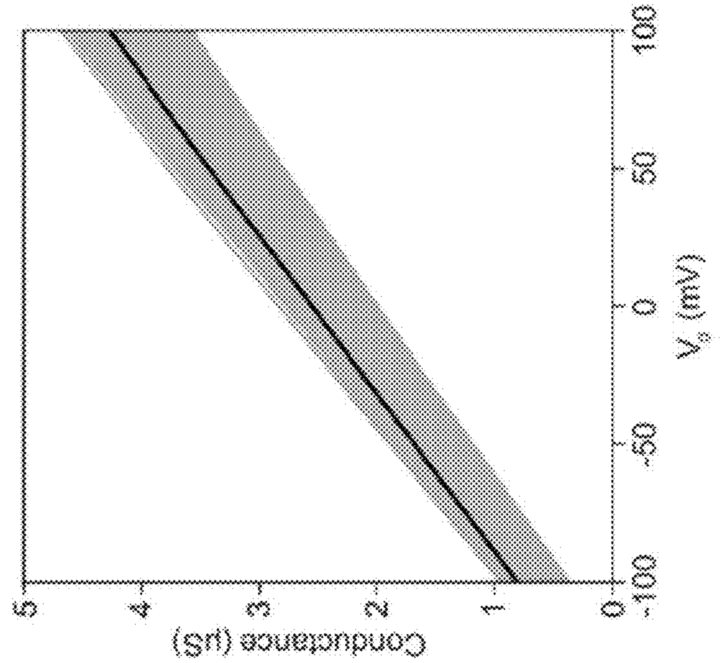

FIG. 43 shows amplification tests of the DDC264. a-c, The DDC264 is a current input analog-to-digital converter. To calculate its amplification, a signal (sine wave, $V_{p-p}$=70 mV) is input into a channel on the DDC264 board and goes through various resistances. The output signal is recorded accordingly, when the resistance is (a) 8.6 MΩ, (b) 17.2 MΩ, and (c) 25.8 MΩ, respectively. The input current is the division of $V_{p-p}$ by the resistance, which is 8.14, 4.07, and 2.71 nA in (a), (b), and (c), and the output voltage reading is correspondingly 111,941, 563,12, and 37,495 mV, respectively. Thus, the amplification of the DDC264 is 13.81 $V \cdot nA^{-1}$, which is used to calculate the FET's current in the conduction channel, and further to derive the membrane potentials during cellular recordings.

FIG. 44 shows electrical characterizations of the 128-FET array. a, Output characteristics of each FET in the array. The measurement is performed with PBS solution (pH: 7.4 at 37° C.) covering the gate regions of all FETs and under a fixed 0 mV potential in the solution by an Ag/AgCl electrode. The background shade of each pixel of the raster plot represents the conductance, in accordance with the shade bar on the right. A box and whisker plot on the right summarizing each sensor's conductance. The 128 FETs have an average conductance of 1.1 μS. b, Transfer characteristics of each FET in the array. The measurement is performed in the same configuration as the water-gate characterization (see FIG. 15). A 100 mV potential is applied to the source, and the signal is collected at the drain of each FET. The background shade of each pixel of the raster plot represents the transconductance, in accordance with the shade bar on the right. A box and whisker plot on the right summarizing each sensor's transconductance. The 128 FETs have an average transconductance of 17 $\mu S \cdot V^{-1}$. c,d, Summary of all 128 FETs' output and transfer characteristics in gray lines, and the average is shown by the dark lines. Both the conductance and transconductance have great consistency among all of the 128 FETs, because of the high reliability of the fabrication process. Each FET has high sensitivity for 3D tissue mapping.

FIG. 45 shows fabrication processes of the PDMS platform for cultivating cardiac microtissues. a, Schematics of the master mold. b, The top view of the well and micro-posts. Unit: mm. c, The PMMA master mold made by laser ablation. d, The PDMS well and two micro-posts made by the PMMA master mold. e, A cardiac microtissue around micro-posts and inside the well. All scale bars are 1 mm.

Figure 46:
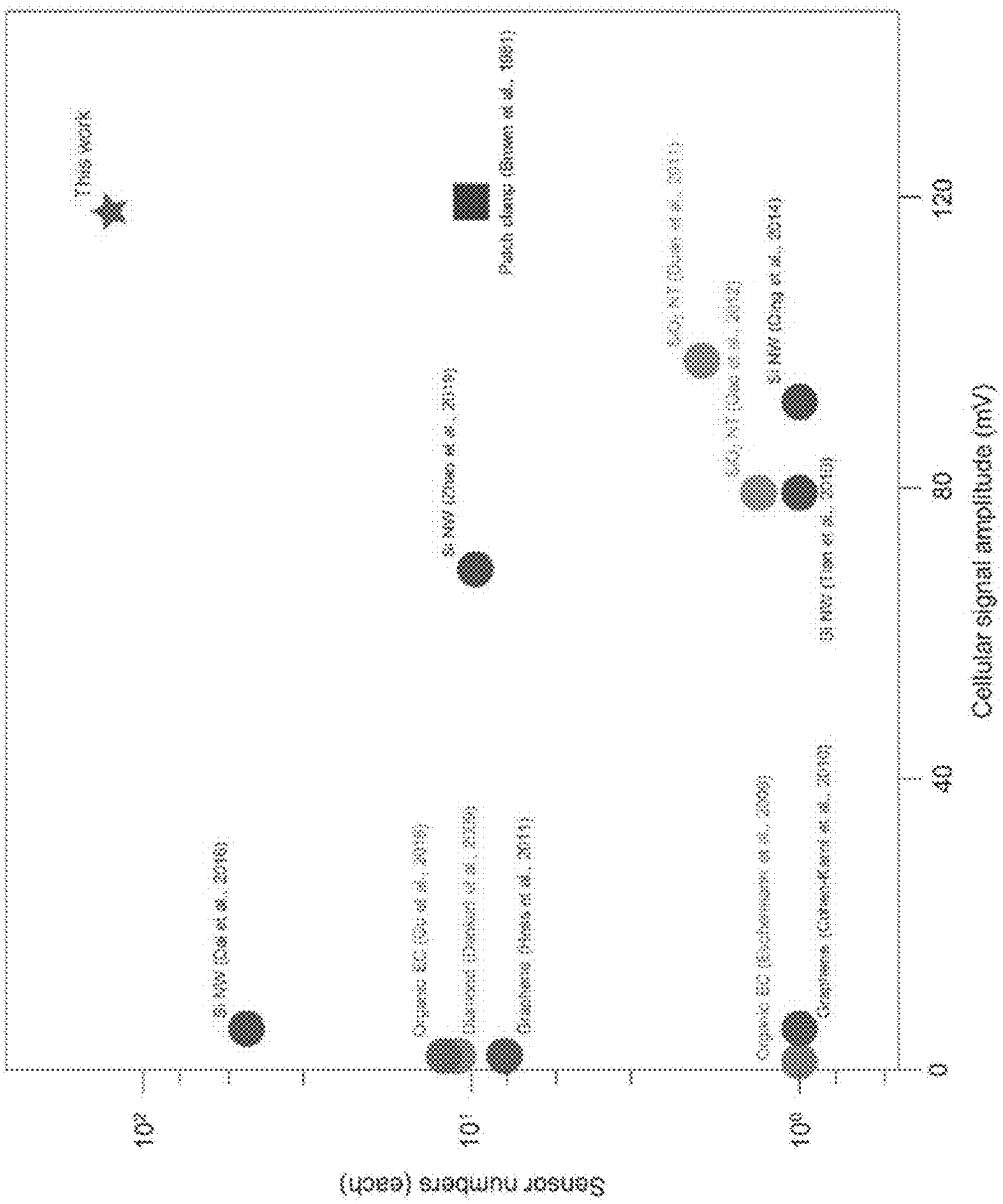
FIG. 46 shows a summary of the 3D FETs for electrophysiology recording.

FIG. 46 shows a summary of the 3D FETs for electrophysiology recording. In comparison with the state of the art, the arrayed FETs demonstrated in this work have the greatest number of sensors and can record full-amplitude cardiomyocytic action potentials comparable to those by the patch-clamp.

TABLE 1

Action potential durations and amplitudes before and after altering ion concentrations or administrating ion blockers. Abnormally high potassium ion or low sodium ion concentration in the extracellular environment would affect cell's membrane resting potential and change its action potential shape. Nifedipine and TTX can interfere with HL-1 cells by diminishing their membrane depolarization upstroke and thus decreasing the action potential duration (APD). The APD50 and APD90 in the table correspond to the action potentials shown in FIG. 3f and g.

| Solutions | APD50 (ms) | APD90 (ms) | Amplitude (mV) | Refractory Period (ms) |
|---|---|---|---|---|
| Normal | 121.2 | 222.4 | 119.4 | 925.4 |
| Hyperkalemia | 95.1 | 166.0 | 75.9 | 1154.6 |
| Hyperkalemia washout | 120.3 | 187.5 | 97.4 | 840.6 |
| Hyponatremia | 179.9 | 270.1 | 63.8 | 893.7 |
| Hyponatremia washout | 140.3 | 238.9 | 98.6 | 975.8 |
| Nifedipine 60 s | 106.0 | 172.9 | 102.9 | 964.8 |
| Nifedipine 120 s | 59.1 | 90.1 | 88.9 | 1022.3 |
| TTX 60 s | 81.2 | 166.6 | 113.4 | 948.4 |
| TTX 120 s | 65.5 | 141.8 | 91.9 | 958.6 |

TABLE 2

Action potential (AP) latencies of the recordings in Extended Data FIG. 5a. The stimulation electrode is placed ~10 mm to the four orientations of the FET array. Recordings of each FET contain five APs. We use the cross-correlation method to calculate the AP latencies between every two recordings. These values are listed below.

| FET | AP1 (ms) | AP2 (ms) | AP3 (ms) | AP4 (ms) | AP5 (ms) |
|---|---|---|---|---|---|
| (nw) | | | | | |
| (2, 1) | 0.68 | 0.68 | 0.67 | 0.68 | 0.68 |
| (1, 1) | 0.00 | 0.00 | 0.00 | 0.00 | 0.00 |
| (2, 2) | 0.65 | 0.66 | 0.65 | 0.65 | 0.65 |
| (1, 2) | 1.46 | 1.46 | 1.44 | 1.44 | 1.47 |
| (2, 3) | 2.24 | 2.26 | 2.23 | 2.24 | 2.22 |
| (1, 3) | 2.09 | 2.11 | 2.08 | 2.10 | 2.08 |
| (2, 4) | 2.75 | 2.80 | 2.71 | 2.74 | 2.72 |
| (1, 4) | 3.42 | 3.42 | 3.40 | 3.40 | 3.41 |
| (2, 5) | 4.08 | 4.08 | 4.07 | 4.07 | 4.08 |
| (1, 5) | 4.75 | 4.76 | 4.74 | 4.74 | 4.75 |
| (ne) | | | | | |
| (2, 1) | 0.00 | 0.00 | 0.00 | 0.00 | 0.00 |
| (1, 1) | 0.66 | 0.65 | 0.66 | 0.68 | 0.67 |
| (2, 2) | 1.50 | 1.52 | 1.50 | 1.52 | 1.50 |
| (1, 2) | 2.21 | 2.16 | 2.18 | 2.24 | 2.24 |
| (2, 3) | 3.06 | 3.09 | 3.05 | 3.07 | 3.09 |
| (1, 3) | 2.95 | 2.97 | 2.95 | 2.93 | 2.96 |
| (2, 4) | 3.65 | 3.65 | 3.68 | 3.62 | 3.71 |
| (1, 4) | 4.30 | 4.31 | 4.29 | 4.31 | 4.29 |
| (2, 5) | 4.95 | 4.94 | 4.95 | 4.94 | 4.95 |
| (1, 5) | 5.71 | 5.71 | 5.76 | 5.73 | 5.68 |
| (sw) | | | | | |
| (2, 1) | 4.36 | 4.35 | 4.35 | 4.35 | 4.36 |
| (1, 1) | 3.62 | 3.64 | 3.59 | 3.64 | 3.62 |
| (2, 2) | 2.98 | 2.98 | 3.01 | 2.94 | 3.02 |
| (1, 2) | 2.19 | 2.19 | 2.16 | 2.16 | 2.20 |
| (2, 3) | 1.51 | 1.55 | 1.51 | 1.51 | 1.54 |
| (1, 3) | 1.35 | 1.36 | 1.33 | 1.33 | 1.35 |
| (2, 4) | 0.67 | 0.68 | 0.72 | 0.70 | 0.66 |
| (1, 4) | 0.00 | 0.00 | 0.00 | 0.00 | 0.00 |
| (2, 5) | 0.65 | 0.69 | 0.65 | 0.68 | 0.60 |
| (1, 5) | 1.40 | 1.40 | 1.40 | 1.40 | 1.40 |
| (se) | | | | | |
| (2, 1) | 5.80 | 5.79 | 5.80 | 5.81 | 5.80 |
| (1, 1) | 5.19 | 5.19 | 5.19 | 5.19 | 5.19 |
| (2, 2) | 4.51 | 4.53 | 4.48 | 4.48 | 4.52 |
| (1, 2) | 3.82 | 3.85 | 3.87 | 3.84 | 3.82 |
| (2, 3) | 3.01 | 2.99 | 3.00 | 3.00 | 3.02 |
| (1, 3) | 2.87 | 2.86 | 2.85 | 2.87 | 2.88 |
| (2, 4) | 2.11 | 2.11 | 2.09 | 2.12 | 2.06 |
| (1, 4) | 1.32 | 1.31 | 1.30 | 1.36 | 1.29 |
| (2, 5) | 0.65 | 0.65 | 0.65 | 0.65 | 0.66 |
| (1, 5) | 0.00 | 0.00 | 0.00 | 0.00 | 0.00 |

TABLE 3

Action potential (AP) latencies of the long-period recordings in FIG. 37. The stimulation electrode is placed ~10 mm to the northwest corner of the FET array. Recordings of each FET contain five APs. We use the cross-correlation method to calculate the AP latencies between each two recordings. These values are listed below.

| Test 1 | | | | | | | | | | | | | | | |
|---|---|---|---|---|---|---|---|---|---|---|---|---|---|---|---|
| FET | AP1 (ms) | AP2 (ms) | AP3 (ms) | AP4 (ms) | AP5 (ms) | AP6 (ms) | AP7 (ms) | AP8 (ms) | AP9 (ms) | AP10 (ms) | AP11 (ms) | AP12 (ms) | AP13 (ms) | AP14 (ms) | AP15 (ms) |
| (2, 1) | 0.68 | 0.68 | 0.69 | 0.68 | 0.67 | 0.67 | 0.69 | 0.68 | 0.67 | 0.68 | 0.69 | 0.67 | 0.69 | 0.69 | 0.68 |
| (1, 1) | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| (2, 2) | 0.65 | 0.64 | 0.67 | 0.63 | 0.63 | 0.66 | 0.63 | 0.66 | 0.67 | 0.64 | 0.66 | 0.63 | 0.66 | 0.64 | 0.67 |
| (1, 2) | 1.46 | 1.47 | 1.46 | 1.47 | 1.47 | 1.48 | 1.44 | 1.49 | 1.45 | 1.46 | 1.49 | 1.46 | 1.47 | 1.43 | 1.45 |
| (2, 3) | 2.23 | 2.19 | 2.18 | 2.20 | 2.20 | 2.20 | 2.19 | 2.24 | 2.20 | 2.18 | 2.20 | 2.20 | 2.21 | 2.21 | 2.20 |
| (1, 3) | 2.08 | 2.11 | 2.08 | 2.07 | 2.10 | 2.08 | 2.11 | 2.12 | 2.09 | 2.08 | 2.09 | 2.08 | 2.08 | 2.07 | 2.07 |
| (2, 4) | 2.75 | 2.77 | 2.80 | 2.75 | 2.78 | 2.76 | 2.76 | 2.79 | 2.75 | 2.77 | 2.75 | 2.71 | 2.76 | 2.81 | 2.72 |
| (1, 4) | 3.44 | 3.43 | 3.42 | 3.40 | 3.42 | 3.43 | 3.39 | 3.42 | 3.43 | 3.41 | 3.44 | 3.44 | 3.41 | 3.40 | 3.39 |

TABLE 3-continued

Action potential (AP) latencies of the long-period recordings in FIG. 37. The stimulation electrode is placed ~10 mm to the northwest corner of the FET array. Recordings of each FET contain five APs. We use the cross-correlation method to calculate the AP latencies between each two recordings. These values are listed below.

| | | | | | | | | | | | | | | | |
|---|---|---|---|---|---|---|---|---|---|---|---|---|---|---|---|
| (2, 5) | 4.08 | 4.10 | 4.09 | 4.06 | 4.08 | 4.08 | 4.10 | 4.07 | 4.06 | 4.10 | 4.09 | 4.09 | 4.07 | 4.06 | 4.08 |
| (1, 5) | 4.78 | 4.79 | 4.73 | 4.73 | 4.75 | 4.73 | 4.77 | 4.74 | 4.78 | 4.72 | 4.72 | 4.75 | 4.73 | 4.73 | 4.77 |

| FET | AP16 (ms) | AP17 (ms) | AP18 (ms) | AP19 (ms) | AP20 (ms) | AP21 (ms) | AP22 (ms) |
|---|---|---|---|---|---|---|---|
| (2, 1) | 0.68 | 0.68 | 0.68 | 0.68 | 0.68 | 0.68 | 0.69 |
| (1, 1) | 0.00 | 0.00 | 0.00 | 0.00 | 0.00 | 0.00 | 0.00 |
| (2, 2) | 0.63 | 0.63 | 0.65 | 0.67 | 0.66 | 0.66 | 0.64 |
| (1, 2) | 1.48 | 1.47 | 1.43 | 1.48 | 1.44 | 1.49 | 1.44 |
| (2, 3) | 2.23 | 2.22 | 2.23 | 2.22 | 2.19 | 2.23 | 2.23 |
| (1, 3) | 2.10 | 2.10 | 2.09 | 2.07 | 2.11 | 2.08 | 2.08 |
| (2, 4) | 2.70 | 2.78 | 2.77 | 2.69 | 2.73 | 2.73 | 2.73 |
| (1, 4) | 3.44 | 3.43 | 3.43 | 3.40 | 3.43 | 3.41 | 3.42 |
| (2, 5) | 4.07 | 4.09 | 4.06 | 4.09 | 4.09 | 4.09 | 4.07 |
| (1, 5) | 4.73 | 4.73 | 4.72 | 4.79 | 4.76 | 4.76 | 4.76 |

Test 2

| FET | AP1 (ms) | AP2 (ms) | AP3 (ms) | AP4 (ms) | AP5 (ms) | AP6 (ms) | AP7 (ms) | AP8 (ms) | AP9 (ms) | AP10 (ms) | AP11 (ms) | AP12 (ms) | AP13 (ms) | AP14 (ms) | AP15 (ms) |
|---|---|---|---|---|---|---|---|---|---|---|---|---|---|---|---|
| (2, 1) | 0.68 | 0.67 | 0.67 | 0.68 | 0.67 | 0.67 | 0.68 | 0.69 | 0.67 | 0.68 | 0.67 | 0.69 | 0.67 | 0.69 | 0.67 |
| (1, 1) | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| (2, 2) | 0.66 | 0.64 | 0.64 | 0.65 | 0.65 | 0.64 | 0.64 | 0.64 | 0.64 | 0.64 | 0.64 | 0.66 | 0.67 | 0.63 | 0.66 |
| (1, 2) | 1.44 | 1.47 | 1.45 | 1.47 | 1.47 | 1.44 | 1.43 | 1.45 | 1.48 | 1.46 | 1.45 | 1.44 | 1.46 | 1.46 | 1.49 |
| (2, 3) | 2.20 | 2.24 | 2.23 | 2.18 | 2.22 | 2.20 | 2.23 | 2.18 | 2.23 | 2.21 | 2.22 | 2.22 | 2.22 | 2.20 | 2.19 |
| (1, 3) | 2.08 | 2.10 | 2.10 | 2.09 | 2.10 | 2.09 | 2.11 | 2.11 | 2.09 | 2.09 | 2.13 | 2.10 | 2.08 | 2.10 | 2.13 |
| (2, 4) | 2.75 | 2.78 | 2.79 | 2.79 | 2.70 | 2.71 | 2.76 | 2.74 | 2.78 | 2.76 | 2.81 | 2.71 | 2.81 | 2.74 | 2.79 |
| (1, 4) | 3.40 | 3.44 | 3.41 | 3.43 | 3.43 | 3.41 | 3.41 | 3.45 | 3.41 | 3.43 | 3.42 | 3.40 | 3.42 | 3.41 | 3.42 |
| (2, 5) | 4.08 | 4.08 | 4.07 | 4.07 | 4.07 | 4.10 | 4.07 | 4.08 | 4.08 | 4.08 | 4.07 | 4.09 | 4.09 | 4.07 | 4.08 |
| (1, 5) | 4.72 | 4.76 | 4.71 | 4.72 | 4.72 | 4.77 | 4.76 | 4.76 | 4.78 | 4.74 | 4.77 | 4.72 | 4.71 | 4.73 | 4.73 |

| FET | AP16 (ms) | AP17 (ms) | AP18 (ms) | AP19 (ms) | AP20 (ms) | AP21 (ms) | AP22 (ms) | AP23 (ms) | AP24 (ms) | AP25 (ms) | AP26 (ms) | AP27 (ms) | AP28 (ms) | AP29 (ms) | AP30 (ms) |
|---|---|---|---|---|---|---|---|---|---|---|---|---|---|---|---|
| (2, 1) | 0.69 | 0.68 | 0.68 | 0.67 | 0.67 | 0.68 | 0.68 | 0.69 | 0.67 | 0.69 | 0.68 | 0.68 | 0.69 | 0.67 | 0.67 |
| (1, 1) | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| (2, 2) | 0.63 | 0.66 | 0.67 | 0.64 | 0.63 | 0.67 | 0.65 | 0.67 | 0.64 | 0.67 | 0.66 | 0.64 | 0.63 | 0.66 | 0.63 |
| (1, 2) | 1.48 | 1.48 | 1.44 | 1.48 | 1.47 | 1.48 | 1.44 | 1.43 | 1.43 | 1.48 | 1.47 | 1.48 | 1.48 | 1.46 | 1.46 |
| (2, 3) | 2.22 | 2.21 | 2.22 | 2.22 | 2.19 | 2.22 | 2.23 | 2.22 | 2.19 | 2.20 | 2.21 | 2.21 | 2.24 | 2.22 | 2.19 |
| (1, 3) | 2.11 | 2.11 | 2.11 | 2.10 | 2.07 | 2.12 | 2.13 | 2.12 | 2.11 | 2.11 | 2.11 | 2.09 | 2.12 | 2.08 | 2.12 |

TABLE 3-continued

Action potential (AP) latencies of the long-period recordings in FIG. 37. The stimulation electrode is placed ~10 mm to the northwest corner of the FET array. Recordings of each FET contain five APs. We use the cross-correlation method to calculate the AP latencies between each two recordings. These values are listed below.

| | | | | | | | | | | | | | | | |
|---|---|---|---|---|---|---|---|---|---|---|---|---|---|---|---|
| (2, 4) | 2.77 | 2.81 | 2.73 | 2.70 | 2.78 | 2.73 | 2.68 | 2.75 | 2.81 | 2.71 | 2.75 | 2.71 | 2.69 | 2.70 | 2.69 |
| (1, 4) | 3.42 | 3.42 | 3.40 | 3.45 | 3.41 | 3.43 | 3.42 | 3.44 | 3.41 | 3.41 | 3.39 | 3.40 | 3.41 | 3.44 | 3.39 |
| (2, 5) | 4.08 | 4.06 | 4.06 | 4.07 | 4.09 | 4.08 | 4.06 | 4.10 | 4.08 | 4.09 | 4.09 | 4.07 | 4.09 | 4.09 | 4.08 |
| (1, 5) | 4.78 | 4.78 | 4.74 | 4.78 | 4.74 | 4.75 | 4.77 | 4.76 | 4.79 | 4.75 | 4.79 | 4.77 | 4.77 | 4.78 | 4.77 |

| FET | AP31 (ms) | AP32 (ms) | AP33 (ms) | AP34 (ms) | AP35 (ms) | AP36 (ms) | AP37 (ms) | AP38 (ms) | AP39 (ms) | AP40 (ms) | AP41 (ms) | AP42 (ms) | AP43 (ms) | AP4 (ms) | 4AP45 (ms) |
|---|---|---|---|---|---|---|---|---|---|---|---|---|---|---|---|
| (2, 1) | 0.68 | 0.68 | 0.68 | 0.69 | 0.68 | 0.68 | 0.68 | 0.68 | 0.68 | 0.68 | 0.69 | 0.68 | 0.68 | 0.68 | 0.67 |
| (1, 1) | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| (2, 2) | 0.64 | 0.67 | 0.64 | 0.65 | 0.67 | 0.66 | 0.64 | 0.67 | 0.64 | 0.64 | 0.63 | 0.64 | 0.67 | 0.64 | 0.64 |
| (1, 2) | 1.44 | 1.48 | 1.49 | 1.49 | 1.45 | 1.47 | 1.47 | 1.45 | 1.47 | 1.45 | 1.45 | 1.47 | 1.47 | 1.44 | 1.49 |
| (2, 3) | 2.21 | 2.21 | 2.19 | 2.21 | 2.23 | 2.22 | 2.19 | 2.21 | 2.23 | 2.20 | 2.22 | 2.22 | 2.23 | 2.21 | 2.24 |
| (1, 3) | 2.12 | 2.12 | 2.11 | 2.09 | 2.11 | 2.11 | 2.12 | 2.13 | 2.07 | 2.08 | 2.12 | 2.12 | 2.10 | 2.09 | 2.09 |
| (2, 4) | 2.77 | 2.70 | 2.77 | 2.77 | 2.81 | 2.69 | 2.70 | 2.69 | 2.69 | 2.73 | 2.76 | 2.76 | 2.75 | 2.79 | 2.79 |
| (1, 4) | 3.40 | 3.41 | 3.44 | 3.41 | 3.39 | 3.41 | 3.43 | 3.45 | 3.45 | 3.40 | 3.43 | 3.39 | 3.42 | 3.44 | 3.44 |
| (2, 5) | 4.08 | 4.10 | 4.08 | 4.09 | 4.07 | 4.08 | 4.07 | 4.07 | 4.09 | 4.10 | 4.10 | 4.10 | 4.07 | 4.09 | 4.08 |
| (1, 5) | 4.71 | 4.78 | 4.77 | 4.74 | 4.76 | 4.73 | 4.77 | 4.76 | 4.73 | 4.72 | 4.71 | 4.77 | 4.77 | 4.72 | 4.78 |

TABLE 4

Signal occurrence times of each FET in the 128-FET array from the 3 D cardiac tissue. The recording duration is 2,048 ms at a sampling rate of 1 kHz. The first recorded signal of the entire array appears at H2i after 43 ms from the start of recording.

| FET label | | | Signal occurrence time (ms) | | | | | | | |
|---|---|---|---|---|---|---|---|---|---|---|
| | | | A | B | C | D | E | F | G | H |
| Loop 1 | a | i | 1480 | — | 864 | 792 | 673 | 547 | — | 166 |
| | | ii | — | 1294 | 865 | 794 | 674 | 549 | 253 | 167 |
| | | iii | — | 1295 | 866 | 795 | 675 | — | 255 | 170 |
| | b | iv | — | — | — | — | 549 | — | 288 | 171 |
| | | v | 1533 | 1329 | 885 | 830 | 552 | 617 | 290 | 173 |
| | | vi | 1534 | — | — | 834 | — | 620 | 293 | 175 |
| Loop 2 | a | i | 1856 | 1030 | — | 717 | — | — | 193 | 43 |
| | | ii | 1857 | 1032 | 894 | 719 | 633 | 487 | 194 | 45 |
| | | iii | 1860 | 1034 | 896 | — | 635 | 491 | 198 | 48 |
| | b | iv | 1880 | 1026 | 907 | — | 644 | 507 | — | — |
| | | v | 1882 | — | 908 | 730 | 645 | 509 | 211 | 73 |
| | | vi | 1886 | 1030 | 909 | 732 | 649 | 511 | 213 | 75 |
| Loop 3 | a | i | — | — | — | — | 591 | 400 | — | 141 |
| | | ii | 1606 | — | 946 | 786 | 593 | 402 | 271 | 143 |
| | | iii | 1608 | 1195 | 948 | 788 | 594 | 404 | 273 | 144 |
| | | iv | 1610 | — | 954 | 791 | 596 | 405 | 113 | 146 |

TABLE 5

Intercellular signal conduction velocity calculation within each unit. The average velocity in the small scale is 18.8 ± 7.5 μm · ms$^{-1}$, which is larger than those velocities of signal conduction between different units in FIG. 5f. Because the distance of the conduction pathway between different units is regarded as a straight line instead of a rugged one, the calculation shortens the resulted conduction distance and thus reduces the velocities.

| FET label | | Signal conduction velocities within each unit (μm · ms$^{-1}$) | | | | | | | |
|---|---|---|---|---|---|---|---|---|---|
| | | A | B | C | D | E | F | G | H |
| Loop 1 | a | — | 35.0 | 35.0 | 23.3 | 35.0 | 17.5 | 17.5 | 17.5 |
| | b | 35.0 | — | — | 8.8 | 11.7 | 11.7 | 14.0 | 17.5 |
| Loop 2 | a | 17.5 | 17.5 | 17.5 | 17.5 | 17.5 | 8.8 | 14.0 | 14.0 |
| | b | 11.7 | 17.5 | 35.0 | 17.5 | 14.0 | 17.5 | 17.5 | 17.5 |
| Loop 3 | a | 17.5 | — | 8.8 | 17.5 | 21.0 | 21.0 | 17.5 | 21.0 |

Additional Embodiments

The particular scalable 3D FET arrays and associated methods described herein for intracellular sensing, as well as for measuring intercellular signal conduction in both two-dimensional (2D) cultures and 3D tissue constructs have been presented for illustrative purposes only and not as a limitation on the systems, devices and method described herein.

More generally, in one aspect, a three-dimensional (3D) FET sensor array and a method for fabricating a three-dimensional (3D) FET sensor array is provided. In accordance with the method, a two-dimensional (2D) precursor field-effect transistor (FET) sensor array having a plurality of nanoscale or microscale FETs is fabricated using any suitable microfabrication techniques. Each of the nanoscale or microscale FETs have a kink at which a FET channel is located. The 2D nanoscale or microscale precursor FET sensor array is caused to buckle or fold into a third dimension using any suitable technique.

In general, nanoscale FETs have a maximum dimension between 1 nm and 100 nm and microscale FETs have a maximum dimension between 100 nm and 1000 micrometers.

In another particular embodiment, fabricating the 2D precursor FET sensor array includes: fabricating a 2D FET structure on a first substrate; transferring the 2D FET structure from the first substrate to a second substrate; depositing, patterning or etching materials on the second substrate after transferring the 2D FET structure to the second substrate; and forming a plurality of additional functional layers on the second substrate to define the 2D precursor FET sensor array.

In another particular embodiment, the additional functional layers include at least one metallization layer in which electrical interconnects are defined and at least one mechanical supporting layer in which a plurality of hinge locations are defined at which the 2D precursor FET sensor array is able to buckle or fold.

In another particular embodiment, the second substrate is a prestrained stretchable and flexible substrate and further comprising causing the 2D precursor sensor array to buckle or fold by releasing strain in the prestrained stretchable and flexible substrate, which compresses the 2D precursor FET sensor array to buckle or fold and thereby extend into a third dimension.

In another particular embodiment, fabricating the 2D FET structure includes patterning and doping a semiconductor material on a first substrate to define a source, drain and gate of each of the nanoscale or microscale FETs.

In another particular embodiment, the prestrained flexible and stretchable substrate is a prestrained elastomer substrate.

In another particular embodiment, defining the hinge locations includes removing the mechanical supporting layer at the hinge locations.

In another particular embodiment, transferring the 2D precursor FET sensor array includes laminating the 2D precursor FET sensor array onto the prestrained stretchable and flexible substrate so that the 2D precursor FET sensor array is bonded to the prestrained stretchable and flexible substrate at bonding sites defined by one or more exposed portions of the mechanical supporting layer.

In another particular embodiment, the nanoscale or microscale FETs each have a maximum dimension that is less than 1 mm in size.

In another particular embodiment, the nanoscale or microscale FETs each have a maximum dimension that is less than 1 μm in size.

In another particular embodiment, the nanoscale FETs each have a maximum dimension that is less than 100 nm in size.

In another particular embodiment, at least two of the nanoscale or microscale FETs in the 3D FET sensor array have one or more different characteristics.

In another particular embodiment, the one or more different characteristics includes different geometries, materials, and/or doping profiles.

In another particular embodiment, a method is provided for determining an electrical property of a cell. In accordance with the method, a channel portion of one or more nanoscale or microscale FETs of a 3D FET sensor array is inserted into an interior of the cell. A direction and velocity of intracellular signal conduction is determined within the cell using the 3D FET sensor array.

In another particular embodiment, the cell is an electrogenic cell.

In another particular embodiment, the cell is cardiomyocyte.

In another particular embodiment, the cell is located in a 2D cell culture.

In another particular embodiment, a method is provided for determining an electrical property of a cell of a cultured tissue. In accordance with the method, a channel portion of a plurality of nanoscale or microscale FETs of a 3D FET sensor array is inserted into the interior of a plurality of cells. A direction and velocity of intercellular signal conduction is determined between the cells in the cultured tissue using the 3D FET sensor array.

In general, any suitable materials and material systems can be used in the various embodiments described above For instance, as previously mentioned, the semiconductor material from which the FETs are formed can be, by way of illustration, Si, Ge, III-V materials, perovskites, two-dimensional materials, and/or carbon nanotubes. The electrodes in the sensor array can be formed from materials such as metals, conductive polymers, oxides, and composites. Likewise, the dielectric materials that are used can be polymers, ceramics, and/or composites.

Certain aspects of the systems and devices described herein for determining the electrical properties of cells and the like are presented in the foregoing description and illustrated in the accompanying drawing using electronic hardware, computer software, or any combination thereof. Whether such elements are implemented as hardware or software depends upon the particular application and design constraints imposed on the overall system. By way of example, such elements, or any portion of such elements, or any combination of such elements may be implemented with one or more processors or controllers. Examples of processors or controllers include microprocessors, microcontrollers, digital signal processors (DSPs), field programmable gate arrays (FPGAs), programmable logic devices (PLDs), state machines, gated logic, discrete hardware circuits, and any other suitable hardware configured to perform the various functionalities described throughout this disclosure. Examples of processors or controllers may also include general-purpose computers or computing platforms selectively activated or reconfigured by code to provide the necessary functionality.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and the invention is not to be limited to the details given herein, but may be modified within the scope and equivalent of the appended claims.

The invention claimed is:

1. A method of fabricating a cell-penetrating three-dimensional (3D) FET sensor array, comprising:
- fabricating a two-dimensional (2D) precursor field-effect transistor (FET) sensor array having a plurality of nanoscale or microscale FETs using microfabrication techniques, each of the nanoscale or microscale FETs having a kink at which a FET channel is located; and
- causing the 2D nanoscale or microscale precursor FET sensor array to reversibly buckle or fold into a third dimension to produce the cell-penetrating three-dimensional (3D) FET sensor array; and
- coating a surface of the cell-penetrating three-dimensional (3D) FET sensor array with a bilayer of parylene and a hydrophobic surface layer of $SiO_2$.

2. The method of claim 1 wherein fabricating the 2D precursor FET sensor array includes:
- fabricating a 2D FET structure on a first substrate;
- transferring the 2D FET structure from the first substrate to a second substrate; depositing, patterning or etching materials on the second substrate after transferring the 2D FET structure to the second substrate; and
- forming a plurality of additional functional layers on the second substrate to define the 2D precursor FET sensor array.

3. The method of claim 2 wherein the additional functional layers include at least one metallization layer in which electrical interconnects are defined and at least one mechanical supporting layer in which a plurality of hinge locations are defined at which the 2D precursor FET sensor array is able to buckle or fold.

4. The method of claim 2 wherein the second substrate is a prestrained stretchable and flexible substrate and further comprising causing the 2D precursor sensor array to buckle or fold by releasing strain in the prestrained stretchable and flexible substrate, which compresses the 2D precursor FET sensor array to buckle or fold and thereby extend into a third dimension.

5. The method of claim 1 wherein fabricating the 2D FET structure includes patterning and doping a semiconductor material on a first substrate to define a source, drain and gate of each of the nanoscale or microscale FETs.

6. The method of claim 4 wherein the prestrained flexible and stretchable substrate is a prestrained elastomer substrate.

7. The method of claim 3 wherein defining the hinge locations includes removing the mechanical supporting layer at the hinge locations.

8. The method of claim 4 wherein transferring the 2D precursor FET sensor array includes laminating the 2D precursor FET sensor array onto the prestrained stretchable and flexible substrate so that the 2D precursor FET sensor array is bonded to the prestrained stretchable and flexible substrate at bonding sites defined by one or more exposed portions of the mechanical supporting layer.

9. The method of claim 1 wherein the nanoscale or microscale FETs each have a maximum dimension that is less than 1 mm in size.

10. The method of claim 1 wherein the nanoscale or microscale FETs each have a maximum dimension that is less than 1 μm in size.

11. The method of claim 1 wherein the nanoscale FETs each have a maximum dimension that is less than 100 nm in size.

12. The method of claim 1 wherein at least two of the nanoscale or microscale FETs in the 3D FET sensor array have one or more different characteristics.

13. The method of claim 12 wherein the one or more different characteristics includes different geometries, materials, and/or doping profiles.

14. A 3D FET sensor array fabricated in accordance with the method of claim 1.

* * * * *